United States Patent [19]
Der et al.

[11] Patent Number: 6,077,686
[45] Date of Patent: Jun. 20, 2000

[54] SHC PROTEINS

[75] Inventors: Channing Der; John O'Bryan, both of Chapel Hill, N.C.; Anthony Pawson, Toronto, Canada

[73] Assignees: Mount Sinai Hospital Corporation, Toronto, Canada; University of North Carolina at Chapel Hill, N.C.

[21] Appl. No.: 08/807,342

[22] Filed: Feb. 28, 1997

Related U.S. Application Data

[60] Provisional application No. 60/012,516, Feb. 29, 1996.

[51] Int. Cl.$^7$ .............................. C12P 21/06; C12N 1/12; C12N 15/00; C12N 5/00
[52] U.S. Cl. .................. 435/69.1; 435/325; 435/320.1; 435/252.1
[58] Field of Search ............................... 435/69.1, 252.3, 435/320.1, 325, 252.1; 530/350; 536/23.5

[56] References Cited

FOREIGN PATENT DOCUMENTS

| 2054602 | 5/1993 | Canada . |
| 0 773 291 A2 | 5/1997 | European Pat. Off. . |
| WO 96/17866 | 6/1996 | WIPO . |

OTHER PUBLICATIONS

Blaikie, P. et al. "A region in Shc distinct from the SH2 domain can bind tyrosine–phosphorylated growth factor receptors." The Journal of Biological Chemistry (Dec., 1994), vol. 269, No. 51, pp. 32031–32034.
O'Bryan et al., "A Mammalian Adaptor Protein with Conserved Src Homology 2 and Phosphotyrosine–Binding Domains is Related to Shc and is Specifically Expressed in the Brain", Proc. Natl. Acad. Sci., 93(7):2729–2734 (Apr. 2, 1996).
O'Bryan et al., "Binding Specifically and Mutational Analysis of the Phosphotyrosine Binding Domain of the Brain–Specific Adaptor Protein ShcC", J. Biol. Chem., 271(20):11787–11791 (May 17, 1996).
W.M. Kavanaugh et al., "An Alternative to SH2 Domains for Binding Tyrosine–Phosphorylated Proteins", Science, 266:1862–1865 (Dec. 16, 1994).
W.M. Kavanaugh et al., "PTB Domain Binding to Signaling Proteins Through a Sequence Motif Containing Phosphotyrosine", Science, 268:1177–1179 (May 26, 1995).
T. Nakamura et al., "N–Shc: A Neural–Specific Adaptor Molecule that Mediates Signaling from Neurotrophin/Trk to Ras.MAPK Pathway", Oncogene, 13:1111–1121 (Sep. 1996).
Z. Songyang et al., "SH2 Domains Recognize Specific Phosphopeptide Sequences", Cell, 72:767–778 (Mar. 12, 1993).
G. Pelicci et al., "A Family of Shc Related Proteins with Conserved PTB, CH1 and SH2 Regions", Oncogene, 13:663–641 (Aug. 1, 1996).
Cribbs, D.H. et al (1996) Neuroscience 75:173–85.
Di Fiore, P.P. et al (1987) Cell 51:1063–1070.
Di Guglielmo et al (1994) Embo J 13:4269–77.
Giorgetti, S.P. et al (1994) Eur J Biochem 223:195–202.
Hauser, C.A. et al (1995) Meth Enzymol 255:412–26.
Henkemeyer, M.L. et al (1994) Oncogene 9:1001–14.
Marais, R. et al (1993) Cell 73:381–93.
Maru, Y. et al (1990) Oncogene 5:445–447.
Merlino, G.T. et al (1985) Mol. Cell. Biol. 5:1722–1734.
O'Bryan, J.P., et al (1995) J Biol Chem 270:551–7.
O'Bryan, J.P. et al (1991) Mol. Cell. Biol. 11:5016–5031.
Pike, C.J. et al (1994) Neuroscience 63:517–31.
Rameh, L.E. et al (1995) Cell 83:821–830.
Serunian, L.A. et al (1991) Meth Enzymol 198:78–87.
Tanaka, M. and W. Herr (1990) Cell 60:375–86.
Ullrich, A.L. et al (1984) Nature 309:418–425.
van der Geer et al (1996) Proc. Natl. Acad. Sci. USA 93:963–968.
Velu, T.J. et al (1987) Science 238:1408–1410.
Yajnik, V. et al (1996) J. Biol. Chem. 271:1813–1816.
Zhou, M.–M. et al (1995) Nature 378:584–592.
Batzer, A. et al (1994) Mol. Cell. Biol. 14, 5192–5201.
Yokote, K. et al (1994) J Biol Chem 269, 15337–43.
Kavanaugh, W.M. et al (1995) Science 268, 1177–1179.
van der geer, P. et al (1995) Curr Biol 5, 404–412.
Pawson, T. (1995) Nature 373, 573–579.
Burns, L.A. et al (1993) J Biol Chem 268, 17659–61.
Cutler, R.L. et al (1993) J Biol Chem 268, 21463–5.
Damen, J.E. et al (1993) Blood 82, 2296–303.
Lanfrancone, L. et al (1995) Oncogene 10, 907–17.
Ravichandran, K.S. et al (1993) Science 262, 902–905.
Crowe, A.J. et al (1994) Oncogene 9, 537–44.
McGlade, J. et al (1992) Proc. Natl. Acad. Sci. USA 89, 8869–8873.
Salcini, A.E. et al (1994) Oncogene 9, 2827–36.
Rozakis, A.M. et al (1992) Nature 360, 689–92.
Obermeier, A. et al (1993) J. Biol. Chem. 268, 22963–22966.
Stephens, R.M. et al (1994) Neuron 12, 691–705.
Lai, K.–M. et al (1995) Mol Cell Biol. 15:4810–4818.
O'Bryan, J.P. et al (1991) Mol. Cell. Biol. 11, 5016–5031.
Songyang, Z. et al (1993) Cell 72, 767–778.
Marengere, L.E. & Pawson, T. (1992) J Biol Chem 267, 22779–86.
Waksman, G. et al (1993) Cell 72, 779–790.
Biscardi, J.S. et al (1996) J Biol Chem 271:29049–59.

(List continued on next page.)

Primary Examiner—Robert A. Wax
Assistant Examiner—Maryam Monshipouri
Attorney, Agent, or Firm—Howson & Howson

[57] ABSTRACT

A Shc protein which is characterized as follows: (a) containing a C-terminal Src homology 2 (SH2) domain, a central proline-rich region (CH1), and an N-terminal phosphotyrosine binding (PTB) domain; (b) it is predominantly expressed in the adult brain; (c) it binds through its SH2 domain to proteins containing the consensus sequence pTyr-(hydrophobic/Glu)-(hydrophobic/Met/Tyr/Ile)-(Ile/Leu/Met/Phe/Tyr); and (d) it associates through its PTB domain with proteins containing the consensus sequence Asn-Pro-X-pTyr where X is any amino acid; nucleic acids encoding the protein; and uses of the protein. The Shc proteins mediate signaling from tyrosine kinases in the nervous system.

10 Claims, 32 Drawing Sheets

OTHER PUBLICATIONS

Bottenstein, J.E., and G.H. Sato (1979) Proc Natl Acad Sci USA 76:514–7.

Brewer, G. and C.W. Cotman (1989) Brain Res 494:65–74.

Pelicci, G. et al (1992) Cell 70, 93–104.

Blaikie, P. et al (1994) J Biol Chem 269, 32031–4.

Kavanaugh, W.M. & Williams, L.T. (1994) Science 266, 1862–5.

Songyang, Z et al (1994) Mol. Cell Biol. 14, 2777–2785.

```
   1  GTGATGAGTG CCACCAGGAA GAGCCGGGCC GGCGACGAGC CACTGCCCAG
  51  GCCCCCTCGG GGCGCGCCGC ACACCAGCGA TCAGGTGCTG GGGCCGGGAG
 101  TCACCTATGT GGTCAAGTAC TTGGGCTGCA TCGAAGTTCT GCGCTCAATG
 151  AGGTCTCTTG ACTTCAGTAC AAGAACTCAG GTTACCAGGG AAGCCATCAG
 201  CCGTGTCTGC GAACGTGTGC CAGGTGCCAA AGGAGCCCTC AAGAAGAGAA
 251  AGCCGCCGAG TAAGATGCTG TCCAGCATCC TGGGGAAGAG CAACCTCCAG
 301  TTCGCAGGGA TGAGCATCTC CCTGACCATC TCCACCGCCA GCCTGAATCT
 351  GCGCACTCCT GACTCCAAAC AGATCATAGC GAACCATCAT ATGCGGTCTA
 401  TCTCTTTTGC CTCAGGGGGA GACCCGGACA CAACGGACTA TGTTGCCTAT
 451  GTCGCTAAGG ACCCTGTCAA TCGCAGAGCT TGCCACATTC TGGAATGCTG
 501  TGACGGGCTA GCCCAAGATG TCATTGGCTC CATCGGACAA GCCTTTGAAC
 551  TCCGGTTCAA ACAGTATTTG CAGTGCCCTT CCAAGGTTCC TGCCCTCCAG
 601  GACCGAATGC AGAGTCTGGA TGAGCCATGG ACTGAAGAAG AGGGAGATGG
 651  CCCTGATCAC CCATACTACA ACAGCGTTCC CACCAAGATG CCTCCCCCAG
 701  GGGGGTTTCT GGATGCTCGA TTGAAAGGCA GACCCCACGC TCCTGAGGCA
 751  GCCCAGTTTG CAGGAAAAGA GCAAACTTAT TACCAGGGAA GACACTTAGG
 801  AGATACATTT GGTGAAGACT GGCAGCGAGC ACCCACCAGG CAAGGCTCCT
 851  TGGACATCTA TAGCACAGCA GAAGGGAAAA CTCACATGGT TCCTGTAGGA
 901  GAAACACCAA CCTATGTCAA CACCCAGCCA GTCCCACCAC AGGTGTGGCC
 951  AGCAGCAACC AGCAGCACTG AGAGCAGCCC ACGGAAGGAC CTCTTTGACA
1001  TGAAGCCCTT TGAAGATGCC CTGAGAAACC AGCCCCTGGG CCCCATGTTG
1051  AGCAAAGCCG CGTCTGTGGA GTGCATCAGC CCGGTCACAC CCAGAGCCCC
1101  GGATGCCAGG ATGCTGGAGG AGCTTAACGC TGAGCCCTGG TACCAAGGAG
1151  AGATGAGCAG GAAGGAGGCA GAGGCCCTGC TACGGGAAGA TGGAGACTTC
1201  CTAGTGAGGA AGAGTACCAC CAACCCCGGC TCCTTTGTCC TCACAGGCAT
1251  GCACAATGGG CAGGCCAAGC ACCTGCTGCT GGTGGACCCG GAAGGCACGA
1301  TCCGGACGAA GGACAGGGTC TTTGACAGCA TCAGCCACCT CATCAATTAC
1351  CACCTCGAGA GCAGCCTGCC CATTGTCTCT GCCGGGAGTG AGCTTTGTCT
1401  CCAGCAACCA GTGGAGAGGA AACCCTGAGC TTGCCCAGCG CCCCAGCCCC
1451  CATACCTTAT GCCAGGTCAG GAAGACTGGC TCTGCGGCTC TCAGCCTATG
1501  GAAATGGGGC ACTGTCTGTG GCCATCACAT TAAAG
```

FIGURE 7

```
  1  MSATRKSRAG  DEPLPRPPRG  APHTSDQVLG  PGVTYVVKYL  GCIEVLRSMR
 51  SLDFSTRTQV  TREAISRVCE  RVPGAKGALK  KRKPPSKMLS  SILGKSNLQF
101  AGMSISLTIS  TASLNLRTPD  SKQIIANHHM  RSISFASGGD  PDTTDYVAYV
151  AKDPVNRRAC  HILECCDGLA  QDVIGSIGQA  FELRFKQYLQ  CPSKVPALQD
201  RMQSLDEPWT  EEEGDGPDHP  YYNSVPTKMP  PPGGFLDARL  KGRPHAPEAA
251  QFAGKEQTYY  QGRHLGDTFG  EDWQRAPTRQ  GSLDIYSTAE  GKTHMVPVGE
301  TPTYVNTQPV  PPQVWPAATS  STESSPRKDL  FDMKPFEDAL  RNQPLGPMLS
351  KAASVECISP  VTPRAPDARM  LEELNAEPWY  QGEMSRKEAE  ALLREDGDFL
401  VRKSTTNPGS  FVLTGMHNGQ  AKHLLLVDPE  GTIRTKDRVF  DSISHLINYH
451  LESSLPIVSA  GSELCLQQPV  ERKP*
```

FIGURE 19A

```
    CGCTGCCGGGGCTCGGGGACGCGGGGCGCGCGGGTGACTCCGGATGTCGCTGACGAGTGG
  1 ------------+---------+---------+---------+---------+---------+   60
    GCGACGGCCCCGAGCCCCTGCGCCCCGCGCGCCCACTGAGGCCTACAGCGACTGCTCACC
     R  C  R  G  S  G  T  R  G  A  R  V  T  P  D  V  A  D  E  W

GTGCGCAAGGGCGGCTTCATTCACAAGCCGGCGCACGGCTGGTTGCATCCCGATGCCAGG
 61 ------------+---------+---------+---------+---------+---------+  120
    CACGCGTTCCCGCCGAAGTAAGTGTTCGGCCGCGTGCCGACCAACGTAGGGCTACGGTCC
     V  R  K  G  G  F  I  H  K  P  A  H  G  W  L  H  P  D  A  R

GTCCTGGGGCCCGGGGTCTCTTACATCGTTCGGTACATGGGCTGCATTGAGGTGCTTCGA
121 ------------+---------+---------+---------+---------+---------+  180
    CAGGACCCCGGGCCCCAGAGAATGTAGCAAGCCATGTACCCGACGTAACTCCACGAAGCT
     V  L  G  P  G  V  S  Y  I  V  R  Y  M  G  C  I  E  V  L  R

TCCATGCGCTCCCTGGATTTCAACACCCGAACACAGGTGACGAGGGAAGCCATCAATCGG
181 ------------+---------+---------+---------+---------+---------+  240
    AGGTACGCGAGGGACCTAAAGTTGTGGGCTTGTGTCCACTGCTCCCTTCGGTAGTTAGCC
     S  M  R  S  L  D  F  N  T  R  T  Q  V  T  R  E  A  I  N  R

CTCCATGAGGCTGTGCCCGGTGTCCGGGGCTCCTGGAAGAAGAAGGCCCCCAACAAGGCT
241 ------------+---------+---------+---------+---------+---------+  300
    GAGGTACTCCGACACGGGCCACAGGCCCCGAGGACCTTCTTCTTCCGGGGGTTGTTCCGA
     L  H  E  A  V  P  G  V  R  G  S  W  K  K  K  A  P  N  K  A

CTGGCCTCCATCTTGGGGAAAAGCAACCTGCGCTTCGCCGGCATGAGCATCTCAGTCAAC
301 ------------+---------+---------+---------+---------+---------+  360
    GACCGGAGGTAGAACCCCTTTTCGTTGGACGCGAAGCGGCCGTACTCGTAGAGTCAGTTG
     L  A  S  I  L  G  K  S  N  L  R  F  A  G  M  S  I  S  V  N

ATCTCCGTGGACGGCCTTAACTTGTCTGTTCCCGCCACCCGCCAGATCATCGCCAACCAT
361 ------------+---------+---------+---------+---------+---------+  420
    TAGAGGCACCTGCCGGAATTGAACAGACAAGGGCGGTGGGCGGTCTAGTAGCGGTTGGTA
     I  S  V  D  G  L  N  L  S  V  P  A  T  R  Q  I  I  A  N  H

CATATGCAGTCTATTTCCTTCGCCTCGGGTGGTGACACGGACATGACTGATTACGTGGCC
421 ------------+---------+---------+---------+---------+---------+  480
    GTATACGTCAGATAAAGGAAGCGGAGCCCACCACTGTGCCTGTACTGACTAATGCACCGG
     H  M  Q  S  I  S  F  A  S  G  G  D  T  D  M  T  D  Y  V  A

TATGTGGCCAAGGACCCCATCAACCAGAGAGCCTGCCACATCTTGGAATGCTGTGAAGGT
481 ------------+---------+---------+---------+---------+---------+  540
    ATACACCGGTTCCTGGGGTAGTTGGTCTCTCGGACGGTGTAGAACCTTACGACACTTCCA
     Y  V  A  K  D  P  I  N  Q  R  A  C  H  I  L  E  C  C  E  G

CTTGCCCAGAGCGTCATCAGCACCGTAGGGCAAGCCTTTGAGCTGCGCTTCAAGCAATAC
541 ------------+---------+---------+---------+---------+---------+  600
    GAACGGGTCTCGCAGTAGTCGTGGCATCCCGTTCGGAAACTCGACGCGAAGTTCGTTATG
     L  A  Q  S  V  I  S  T  V  G  Q  A  F  E  L  R  F  K  Q  Y

CTGCACAGTCCGCCCAAGGCGGTAGTGCCCCCTGAAAGGCTGACTGGGCTGGAGGAGTTG
601 ------------+---------+---------+---------+---------+---------+  660
    GACGTGTCAGGCGGGTTCCGCCATCACGGGGACTTTCCGACTGACCCGACCTCCTCAAC
     L  H  S  P  P  K  A  V  V  P  P  E  R  L  T  G  L  E  E  L

GCCTGGGGAGATGATGACGCTGCTGCAGACCACAATTACTACAACAGCATTCCGGGAAAG
661 ------------+---------+---------+---------+---------+---------+  720
    CGGACCCCTCTACTACTGCGACGACGTCTGGTGTTAATGATGTTGTCGTAAGGCCCTTTC
```

FIGURE 19B

```
           A  W  G  D  D  D  A  A  A  D  H  N  Y  Y  N  S  I  P  G  K
      GAGCCACCCCTGGGCGGGCTGGTGGACTCCAGACTGGCTGTCACACAGCCCTGTGCGCTG
721   ---------+---------+---------+---------+---------+---------+   780
      CTCGGTGGGGACCCGCCCGACCACCTGAGGTCTGACCGACAGTGTGTCGGGACACGCGAC
       E  P  P  L  G  G  L  V  D  S  R  L  A  V  T  Q  P  C  A  L

GCGACACTCGGGGGCCTTGGACAGGGAATGACACCAGTATGGAGAGATGCCCGTGGCTTG
781   ---------+---------+---------+---------+---------+---------+   840
      CGCTGTGAGCCCCCGGAACCTGTCCCTTACTGTGGTCATACCTCTCTACGGGCACCGAAC
       A  T  L  G  G  L  G  Q  G  M  T  P  V  W  R  D  A  R  G  L

CCTTGGGACATGGGCCCCTCTGGAGCAGCCCCACCGGGGGATGGCTACGTGCAGGCAGAT
841   ---------+---------+---------+---------+---------+---------+   900
      GGAACCCTGTACCCGGGGAGACCTCGTCGGGGTGGCCCCCTACCGATGCACGTCCGTCTA
       P  W  D  M  G  P  S  G  A  A  P  P  G  D  G  Y  V  Q  A  D

GCCCGAGGGCCACATGACTACGAGGAGCACCTGTATGTCAATACCCAGGGCCTGGATGCT
901   ---------+---------+---------+---------+---------+---------+   960
      CGGGCTCCCGGTGTACTGATGCTCCTCGTGGACATACAGTTATGGGTCCCGGACCTACGA
       A  R  G  P  H  D  Y  E  E  H  L  Y  V  N  T  Q  G  L  D  A

GTGGAGCTTGAGGACACCGCCGAGGCACCTCTGCAGTTTGAGGACAGCCCCAAGAAGGAC
961   ---------+---------+---------+---------+---------+---------+   1020
      CACCTCGAACTCCTGTGGCGGCTCCGTGGAGACGTCAAACTCCTGTCGGGGTTCTTCCTG
       V  E  L  E  D  T  A  E  A  P  L  Q  F  E  D  S  P  K  D

CTGTTTGACATGCGACCCTTTGAAGATGCCCTGAAGTTGCACGCGTGCTCAGTGGCAGCC
1021  ---------+---------+---------+---------+---------+---------+   1080
      GACAAACTGTACGCTGGGAAACTTCTACGGGACTTCAACGTGCGCACGAGTCACCGTCGG
       L  F  D  M  R  P  F  E  D  A  L  K  L  H  A  C  S  V  A  A

GGCATCACTGCAGCCTCACCCCCTCTGGAAGACCAGTGGCCCAGTCCCCCTACCCGCAGG
1081  ---------+---------+---------+---------+---------+---------+   1140
      CCGTAGTGACGTCGGAGTGGGGGAGACCTTCTGGTCACCGGGTCAGGGGGATGGGCGTCC
       G  I  T  A  A  S  P  P  L  E  D  Q  W  P  S  P  P  T  R  R

GCCCCCATTGCACCCACAGAGGAGCAATTGAGGCAGGAGCCCTGGTACCACGGACGAATG
1141  ---------+---------+---------+---------+---------+---------+   1200
      CGGGGGTAACGTGGGTGTCTCCTCGTTAACTCCGTCCTCGGGACCATGGTGCCTGCTTAC
       A  P  I  A  P  T  E  E  Q  L  R  Q  E  P  W  Y  H  G  R  M

AGCCGTCGGGCTGCAGAGAAGCTGCTTCGGGCCGATGGGGACTTCCTTGTGAGAGACAGC
1201  ---------+---------+---------+---------+---------+---------+   1260
      TCGGCAGCCCGACGTCTCTTCGACGAAGCCCGGCTACCCCTGAAGGAACACTCTCTGTCG
       S  R  R  A  A  E  K  L  L  R  A  D  G  D  F  L  V  R  D  S

GTCACCAACCCGGGGCAGTATGTCCTCACGGGCATGCATGCGGGGCAGCCCAAGCACCTG
1261  ---------+---------+---------+---------+---------+---------+   1320
      CAGTGGTTGGGCCCCGTCATACAGGAGTGCCCGTACGTACGCCCCGTCGGGTTCGTGGAC
       V  T  N  P  G  Q  Y  V  L  T  G  M  H  A  G  Q  P  K  H  L

CTGCTGGTGGACCCCGAGGGTGTGGTGCGGACGAAAGATGTGTTGTTTGAGAGCATCAGC
1321  ---------+---------+---------+---------+---------+---------+   1380
      GACGACCACCTGGGGCTCCCACACCACGCCTGCTTTCTACACAACAAACTCTCGTAGTCG
       L  L  V  D  P  E  G  V  V  R  T  K  D  V  L  F  E  S  I  S

CACCTCATAGACTATCACCTGAAGAATGGGCTGCCTATCGTGGCTGCTGAGAGCGAGCTG
1381  ---------+---------+---------+---------+---------+---------+   1440
      GTGGAGTATCTGATAGTGGACTTCTTACCCGACGGATAGCACCGACGACTCTCGCTCGAC
```

FIGURE 19C

```
        H  L  I  D  Y  H  L  K  N  G  L  P  I  V  A  A  E  S  E  L
     CATCTGCGGGGAGTGGTCTCTCGGGAGCCATGAGCCAGGTGACAGTCCTCACCCCAACTT
1441 ---------+---------+---------+---------+---------+---------+ 1500
     GTAGACGCCCCTCACCAGAGAGCCCTCGGTACTCGGTCCACTGTCAGGAGTGGGGTTGAA
        H  L  R  G  V  V  S  R  E  P  *  A  R  *  Q  S  S  P  Q  L

CTACCCCTAGATGCCCTTGCTGAGGCCTTTCTCTCAGATCCTGAAGCCACGAGAACCAGA
1501 ---------+---------+---------+---------+---------+---------+ 1560
     GATGGGGATCTACGGGAACGACTCCGGAAAGAGAGTCTAGGACTTCGGTGCTCTTGGTCT
        L  P  L  D  A  L  A  E  A  F  L  S  D  P  E  A  T  R  T  R

ATGGTTACCACCTCTCCTTCCACACGAGCCCTCGGGAAGCCGCCTTTCCCAGCTGTGCTC
1561 ---------+---------+---------+---------+---------+---------+ 1620
     TACCAATGGTGGAGAGGAAGGTGTGCTCGGGAGCCCTTCGGCGGAAAGGGTCGACACGAG
        M  V  T  T  S  P  S  T  R  A  L  G  K  P  P  F  P  A  V  L

GCTCAGCTGGGGGGGCCCGGTACCCAATTCGCCCTATAGTGA
1621 ---------+---------+---------+---------+-- 1662
     CGAGTCGACCCCCCCGGGCCATGGGTTAAGCGGGATATCACT
        A  Q  L  G  G  P  G  T  Q  F  A  L  *  *
```

SHC PROTEINS

This application claims benefit of Provisional Application Ser. No.60/012,516 filed Feb. 29, 1996.

FIELD OF THE INVENTION

The invention relates to novel ShcC proteins, truncations, analogs, homologs, and isoforms thereof; nucleic acid molecules encoding these proteins; and, uses of the proteins and nucleic acid molecules.

BACKGROUND OF THE INVENTION

The mammalian shcA gene encodes three overlapping proteins of 46, 52 and 66 kDa, that differ only in the extent of their N-terminal sequences (1). These shcA gene products share a C-terminal Src homology 2 (SH2) domain, a central proline-rich region (CH1), and a more N-terminal phosphotyrosine-binding (PTB) domain (2, 3). The ShcA SH2 domain binds preferentially to phosphotyrosine sites with the sequence pTyr-(hydrophobic/Glu)-X-(Ile/Leu/Met) [SEQ ID NO:9], and recognizes specific autophosphorylation sites in the activated epidermal growth factor (EGF) and platelet-derived growth factor (PDGF)-receptors (4, 5, 6). In contrast, the ShcA PTB domain has recently been shown to bind with high affinity to phosphotyrosine sites with the consensus sequence Leu/Ile-X-Asn-Pro-X-pTyr [SEQ ID NO:10]. Such sites are found in a number of growth factor receptors, notably the nerve growth factor receptor (Trk), and in polyoma middle T antigen (7, 8). The ShcA PTB domain, therefore, recognizes phosphotyrosine in the context of amino-terminal residues, as distinct from SH2 domains, which recognize amino acids C-terminal to phosphotyrosine (9). The p66 ShcA isoform, which is generated by alternative splicing, has an additional proline-rich N-terminal sequence (CH2) (Migliaccio, et. al).

These results have indicated that ShcA proteins have two modules that bind phosphotyrosine sites with entirely different specificities. Potentially for this reason, ShcA is a prominent substrate for tyrosine phosphorylation in cells stimulated with a wide variety of growth factors and cytokines, and in lymphoid cells stimulated with antigen (10, 11, 12, 13, 14). In addition, ShcA proteins are phosphorylated by oncogenic receptor and cytoplasmic tyrosine kinases (15, 16).

The principal phosphorylation site of human ShcA phosphorylation is at Tyr 317, located in the central CH1 region within the motif Tyr-Val-Asn-Val (aa 317–320 of SEQ ID NO:7, 17). A very similar element is found in mouse ShcA (Tyr313-Val-Asn-Ile; aa 313–316 of SEQ ID NO:6). Phosphorylation of this residue creates a high affinity binding site for the SH2 domain of a second adaptor protein, Grb2, which binds preferentially to phosphotyrosine sites with Asn at the +2 position (4). Grb2 is, in turn, associated through its SH3 domains with proline-rich motifs in the C-terminal tail of mSos1, a Ras guanine nucleotide exchange factor. ShcA phosphorylation, therefore, induces the formation of a ternary complex containing ShcA, Grb2 and mSos1, which may activate the Ras pathway (9). Consistent with this possibility, ShcA overexpression induces transformation of rodent fibroblasts in a fashion that is dependent on Tyr 317 (17). ShcA overexpression also elicits Ras-dependent neurite outgrowth in PC12 neuronal cells (18). This latter observation suggests that the binding of autophosphorylated Trk to the ShcA PTB domain, and ensuing ShcA phosphorylation and association with Grb2, is one mechanism by which the Trk tyrosine kinase might activate the Ras pathway (19, 20).

The significance of ShcA in signal transduction has been underscored by the identification of a Drosophila Shc protein that interacts through its PTB domain with the activated Drosophila EGF-receptor (21). Analysis of Drosophila Shc has also raised the possibility that Shc proteins have functions in addition to Ras activation.

SUMMARY OF THE INVENTION

The present inventors have identified a gene designated shcC, and they have characterized the shcC gene product. The shcC gene product has a C-terminal SH2 domain, a CH1 region with a Grb2-binding site, and an N-terminal PTB domain. The ShcC SH2 domain binds phosphotyrosine-containing peptides and receptors with a specificity related to, but distinct from that of the ShcA SH2 domain. ShcC was also shown to have a functional PTB domain. In particular, the ShcC PTB domain was shown to specifically associate in vitro with autophosphorylated receptors for nerve growth factor (NGF) and epidermal growth factor (EGF). In contrast to shcA, which is widely expressed, shcC RNA and proteins are predominantly expressed in the adult brain. These results indicate that ShcC mediates signalling from tyrosine kinases in the nervous system, such as receptors for neurotrophins.

Isolated domains of ShcC were also shown to inhibit or revert the transformed phenotype of some tumors indicating that the domains have efficacy as therapeutic agents. In particular, studies confirmed that the SH2 domain of ShcC can both inhibit and revert some of the transformed properties resulting from overexpression of EGFR. The PTB domain of ShcC also showed inhibitory effects on EGFR transformation.

The present inventors also identified a gene designated shcB which represents the mouse homolog of the human shcA-like gene sck. The ShcB SH2 domain also binds to phosphotyrosine-containing peptides and receptors with a specificity related to, but distinct from that of the ShcA and ShcC SH2 domains. In contrast to ShcC, SchB is expressed at low levels in tissues other than the brain, such as salivary gland, uterus, ovary, and testis.

Broadly stated the present invention relates to an isolated nucleic acid molecule comprising a sequence encoding a Shc protein which Shc protein is characterized as follows: (a) containing a C-terminal Src homology 2 (SH2) domain, a central proline-rich region (CH1), and an N-terminal phosphotyrosine binding (PTB) domain; (b) it is predominantly expressed in the adult brain; (c) it binds through its SI12 domain to proteins containing the consensus sequence pTyr-(hydrophobic/Glu)-(hydrophobic/Met/Tyr or hydrophobic/Met/Ile)-(Ile/Leu/Met or Phe/Tyr) [SEQ ID NO:11]; and (d) it associates through its PTB domain with proteins containing the consensus sequence Asn-Pro-X-pTyr [SEQ ID NO:12] where X is any amino acid. The Shc proteins encoded by the nucleic acid molecule are also characterized by a motif comprising Tyr-Val-Asn-Thr [SEQ ID NO:13] which associates with Grb2.

In accordance with an embodiment of the invention, the purified and isolated nucleic acid molecule comprises:
  (i) a nucleic acid sequence encoding a protein having the amino acid sequence shown in SEQ ID NO:4 or FIG. 19;
  (ii) nucleic acid sequences complementary to (i); or
  (iii) a nucleic acid capable of hybridizing under stringent conditions to a nucleic acid of (i).

Preferably, the purified and isolated nucleic acid molecule comprises:
  (i) a nucleic acid sequence as shown in SEQ ID NO:3 or FIG. 19, wherein T can also be U;

(ii) nucleic acid sequences complementary to (i), preferably complementary to the full length nucleic acid sequence shown in SEQ ID NO:3 or FIG. 19;

(iii) a nucleic acid capable of hybridizing under stringent conditions to a nucleic acid of (i); or (iv) a nucleic acid molecule differing from any of the nucleic acids of (i) to (iii) in codon sequences due to the degeneracy of the genetic code.

In accordance with another embodiment of the invention, an isolated nucleic acid molecule is provided comprising a sequence encoding ShcC with Shc protein is characterized as follows: (a) containing a C-terminal Src homology 2 (SH2) domain, a central proline-rich region (CH1), and an N-terminal phosphotyrosine binding (PTB) domain; (b) it is predominantly expressed in the adult brain; (c) it binds through its SH2 domain to proteins containing the consensus sequence pTyr-(hydrophobic/Glu)-(hydrophobic/Met/Tyr)-(Ile/Leu/Met) [SEQ ID NO:14]; and (d) it associates through its PTB domain with proteins containing the consensus sequence Asn-Pro-X-pTyr [SEQ ID NO:12] where X is any amino acid. The ShcC protein encoded by the nucleic acid is also characterized by a motif comprising Tyr-Val-Asn-Thr [SEQ ID NO:13] which associates with Grb2.

The purified and isolated nucleic acid molecule preferably comprises:

(i) a nucleic acid sequence encoding a protein having the amino acid sequence shown in SEQ ID NO:2 or FIG. 7;

(ii) nucleic acid sequences complementary to (i); or (iii) a nucleic acid capable of hybridizing under stringent conditions to a nucleic acid of (i).

Most preferably, the purified and isolated nucleic acid molecule comprises:

(i) a nucleic acid sequence as shown in SEQ ID NO:1 or FIG. 6, wherein T can also be U;

(ii) nucleic acid sequences complementary to (i), preferably complementary to the full length nucleic acid sequence shown in SEQ ID NO:1 or FIG. 6;

(iii) a nucleic acid capable of hybridizing under stringent conditions to a nucleic acid of (i); or (iv) a nucleic acid molecule differing from any of the nucleic acids of (i) to (iii) in codon sequences due to the degeneracy of the genetic code.

The invention also contemplates a nucleic acid molecule comprising a sequence encoding a truncation of ShcC, an analog, or a homolog of ShcC or a truncation thereof. (ShcC and truncations, analogs and homologs of ShcC are also collectively referred to herein as "ShcC protein" or "ShcC proteins").

The nucleic acid molecules of the invention may be inserted into an appropriate expression vector, i.e. a vector which contains the necessary elements for the transcription and translation of the inserted coding sequence. Accordingly, recombinant expression vectors adapted for transformation of a host cell may be constructed which comprise a nucleic acid molecule of the invention and one or more transcription and translation elements linked to the nucleic acid molecule.

The recombinant expression vector can be used to prepare transformed host cells expressing a ShcC or ShcB protein. Therefore, the invention further provides host cells containing a recombinant molecule of the invention. The invention also contemplates transgenic non-human mammals whose germ cells and somatic cells contain a recombinant molecule comprising a nucleic acid molecule of the invention in particular one which encodes an analog of ShcC, or a truncation of ShcC.

The invention further provides a method for preparing a novel ShcC or ShcB protein utilizing the purified and isolated nucleic acid molecules of the invention. In an embodiment a method for preparing a ShcC or ShcB protein is provided comprising (a) transferring a recombinant expression vector of the invention into a host cell; (b) selecting transformed host cells from untransformed host cells; (c) culturing a selected transformed host cell under conditions which allow expression of the ShcC protein or ShcB protein; and (d) isolating the ShcC protein or ShcB protein.

The invention further broadly contemplates an isolated ShcC protein which is characterized as follows: (a) containing a C-terminal Src homology 2 (SH2) domain, a central proline-rich region (CH1), and an N-terminal phosphotyrosine binding (PTB) domain; (b) it is predominantly expressed in the adult brain; (c) it binds through its SH2 domain to proteins containing the consensus sequence pTyr-(hydrophobic/Glu)-(hydrophobic/Met/Tyr)-(Ile/Leu/Met) [SEQ ID NO:14]; and (d) it associates through its PTB domain with proteins containing the consensus sequence Asn-Pro-X-pTyr [SEQ ID NO:12] where X is any amino acid. The ShcC protein is also characterized by a motif comprising Tyr-Val-Asn-Thr [SEQ ID NO:13] which associates with Grb2. In particular, the ShcC protein is characterized by its ability to bind to phosphotyrosine-containing peptides and receptors, and associate through its PTB domain in vitro with autophosphorylated receptors for nerve growth factor (NGF) and epidermal growth factor (EGF). In an embodiment of the invention, a purified ShcC protein is provided which has the amino acid sequence as shown in SEQ ID NO:2 or FIG. 7. The purified and isolated ShcC protein of the invention may be activated i.e. phosphorylated. The invention also includes truncations of the protein and analogs, homologs, and isoforms of the protein and truncations thereof.

The invention also includes a ShcB protein having the amino acid sequence as shown in SEQ ID NO:4 or FIG. 19.

The Shc proteins of the invention may be conjugated with other molecules, such as proteins, to prepare fusion proteins. This may be accomplished, for example, by the synthesis of N-terminal or C-terminal fusion proteins.

The invention further contemplates antibodies having specificity against an epitope of a ShcB or ShcC protein of the invention. Antibodies may be labelled with a detectable substance and used to detect ShcC or ShcB proteins in tissues and cells.

The invention also permits the construction of nucleotide probes which are unique to the nucleic acid molecules of the invention and accordingly to ShcC or ShcB proteins. Therefore, the invention also relates to a probe comprising a sequence encoding a ShcC or ShcB protein. The probe may be labelled, for example, with a detectable substance and it may be used to select from a mixture of nucleotide sequences a nucleotide sequence coding for a protein which displays one or more of the properties of ShcC or ShcB.

The invention still further provides a method for identifying a substance which is capable of binding to a ShcC or ShcB protein, or an activated form thereof, comprising reacting a ShcC or ShcB protein or activated form thereof, with at least one substance which potentially can bind with the ShcC or ShcB protein, or activated form thereof, under conditions which permit the formation of complexes between the substance and ShcC or ShcB protein or activated form thereof, and assaying for complexes, for free substance, for non-complexed Shc protein, or an activated form thereof, or for activation of ShcC or ShcB.

Still further the invention provides a method for assaying a medium for the presence of an agonist or antagonist of the interaction of a ShcC or ShcB protein or activated form thereof, and a substance which binds to ShcC or ShcB protein or activated form thereof. In an embodiment, the method comprises providing a known concentration of ShcC or ShcB protein, with a substance which is capable of binding to ShcC or ShcB protein and a suspected agonist or antagonist substance under conditions which permit the formation of complexes between the substance and ShcC or ShcB protein, and assaying for complexes, for free substance, for non-complexed ShcC or ShcB protein, or for activation of ShcC or ShcB protein.

In an embodiment, the invention provides a method for assaying a medium for the presence of an agonist or antagonist of the interaction of a ShcC or ShcB protein or activated form thereof, and a substance which binds to ShcC or ShcB protein or activated form thereof comprising (a) reacting a ShcC or ShcB protein, or activated form thereof, a substance which binds to the ShcC or ShcB protein, or activated form thereof, and a test substance under conditions which permit the formation of complexes between the substance and ShcC or ShcB protein or activated form thereof; (b) assaying for complexes, for free substance, for non-complexed ShcC or ShcB protein, or for activation of ShcC or ShcB protein; and (c) comparing to a control in the absence of the test substance to determine if the test substance is an agonist or antagonist of the interaction of a ShcC or ShcB protein or activated form thereof, and the substance.

Substances which affect a ShcC or ShcB protein may also be identified using the methods of the invention by comparing the pattern and level of expression of ShcC or ShcB protein of the invention in tissues and cells of the brain, in the presence, and in the absence of the substance.

The invention still further provides a synthetic substance which inhibits the interaction between a ShcC or ShcB protein or activated form thereof, and a substance which binds to ShcC or ShcB protein or activated form thereof which is first identifed by: (a) reacting a ShcC or ShcB protein, or activated form thereof, a substance which binds to the ShcC or ShcB protein, or activated form thereof, and a test substance under conditions which permit the formation of complexes between the substance and ShcC or ShcB protein or activated form thereof; (b) assaying for complexes, for free substance, for non-complexed ShcC or ShcB protein, or for activation of ShcC or ShcB protein; and (c) identifying the synthetic substance based on its ability to inhibit the interaction of a ShcC or ShcB protein or activated form thereof, and the substance when compared to a control.

The substances identified using the methods of the invention may be used in the treatment of conditions involving the perturbation of signalling pathways, and in particular in conditions involving perturbation of signalling pathways affecting the nervous system. Accordingly, the substances may be formulated into compositions for adminstration to individuals suffering from one of these conditions. Therefore, the present invention also relates to a composition comprising one or more of an SH2 domain, PTB domain, and Grb2 binding site of a ShcC or ShcB protein, or a substance identified using the methods of the invention, and a pharmaceutically acceptable carrier, excipient or diluent. A method for treating or preventing a condition involving a ShcC or ShcB regulatory system is also provided comprising administering to a patient in need thereof, a composition of the invention.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 1 shows the amino acid sequence alignment of the Shc family of proteins [SEQ ID NO:2, 5–9];

FIG. 6 shows the nucleic acid sequence of the ShcC cDNA;

FIG. 7 shows the amino acid sequence of ShcC;

FIGS. 19A–C shows the nucleic acid and amino acid sequence of ShcB.

DETAILED DESCRIPTION OF THE INVENTION

Figure 2A:
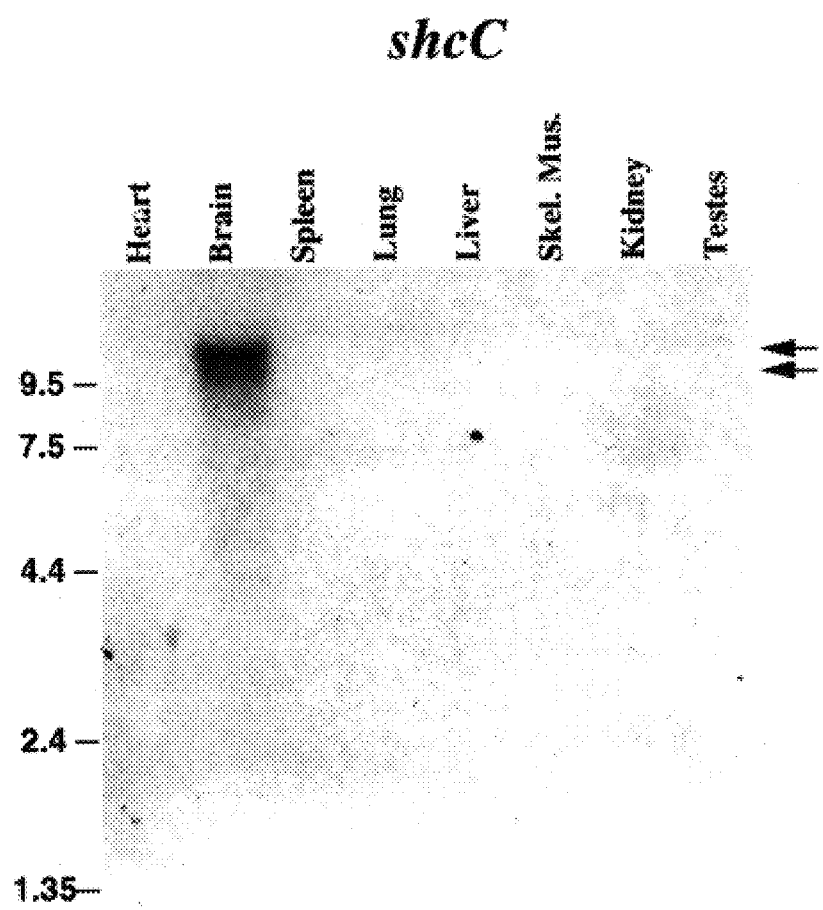
FIG. 2A shows immunoblots of a Northern analysis showing ShcC RNA is specifically expressed in brain tissues.

I. Nucleic Acid Molecules of the Invention

As hereinbefore mentioned, the invention provides an isolated nucleic acid molecule having a sequence encoding ShcC. The term "isolated" refers to a nucleic acid substantially free of cellular material or culture medium when produced by recombinant DNA techniques, or chemical reactants, or other chemicals when chemically synthesized. An "isolated" nucleic acid is also free of sequences which naturally flank the nucleic acid (i.e., sequences located at the 5' and 3' ends of the nucleic acid molecule) from which the nucleic acid is derived. The term "nucleic acid" is intended to include DNA and RNA and can be either double stranded or single stranded. In a preferred embodiment, the nucleic acid molecule encodes ShcC having the amino acid sequence as shown in SEQ ID NO:2 and FIG. 7. In another embodiment, the nucleic acid molecule is a DNA comprising the coding region (bp 4 to 1428) of the nucleotide sequence as shown in SEQ ID NO:1 and FIG. 6.

The invention includes nucleic acid sequences complementary to the nucleic acid encoding ShcC having the amino acid sequence as shown in SEQ ID NO:2 and FIG. 7, and the nucleotide sequence as shown in SEQ ID NO:1 and FIG. 6, preferably the nucleic acid sequences complementary to the full length nucleic acid sequence shown in SEQ ID NO:1 and FIG. 6.

Figure 1:
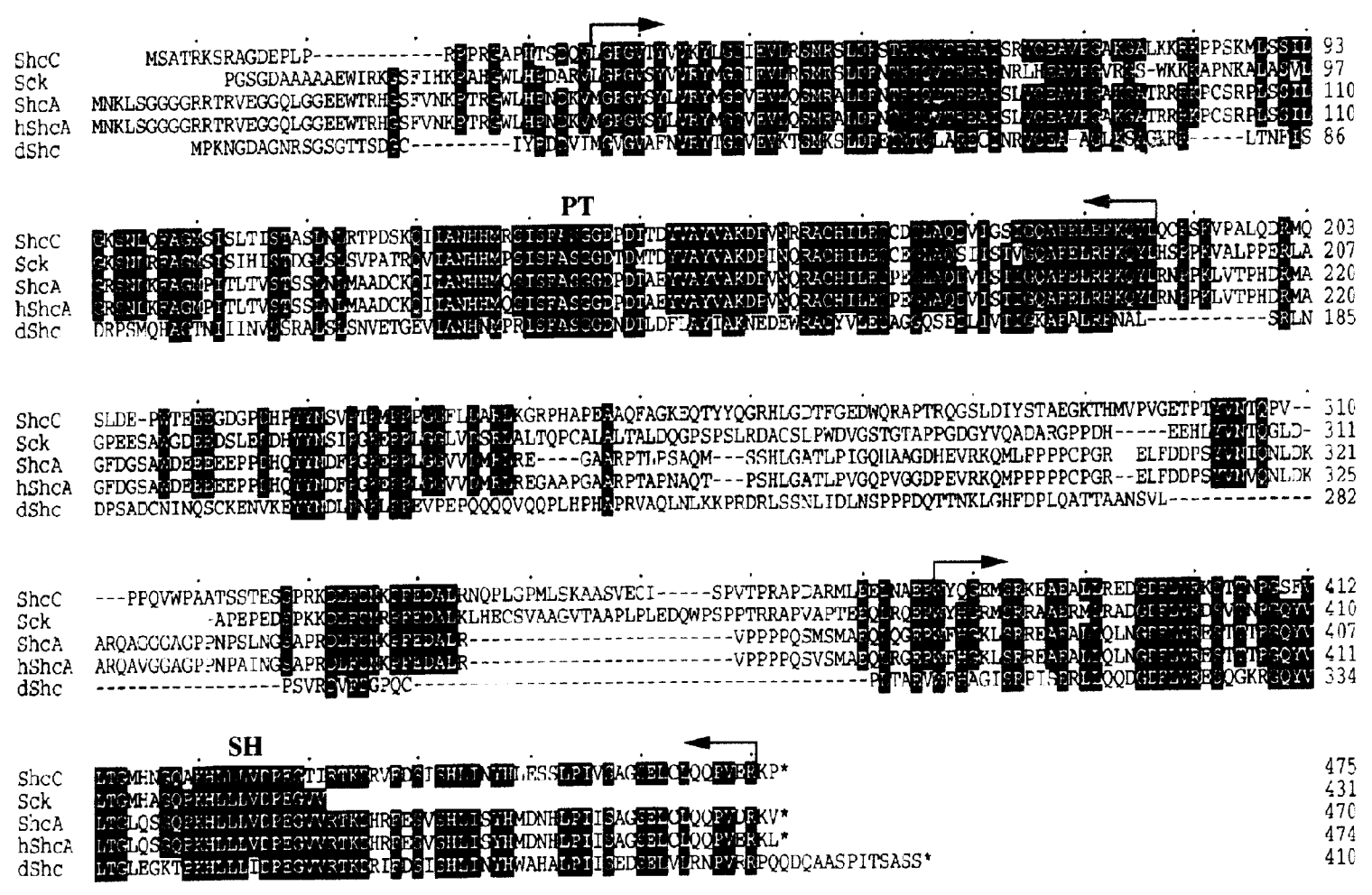

The invention includes nucleic acid molecules having substantial sequence identity or homology to the nucleic acid sequence as shown in SEQ ID NO:1 and FIG. 6, or encoding Shc proteins having substantial homology to the amino acid sequence shown in SEQ ID. NO. 2 and FIG. 7. Homology refers to sequence similarity between sequences and can be determined by comparing a position in each sequence which may be aligned for purposes of comparison (See FIG. 1 for an alignment of the amino acid sequences [SEQ ID NO:2, 5–9] of proteins of the Shc family). When a position in the compared sequence is occupied by the same nucleotide base or amino acid, then the molecules are matching or have identical positions shared by the sequences.

Isolated nucleic acid molecules encoding a protein having the activity of ShcC as described herein, and having a sequence which differs from the nucleic acid sequence shown in SEQ ID NO:1 and FIG. 6, due to degeneracy in the genetic code are also within the scope of the invention. Such nucleic acids encode functionally equivalent proteins (e.g., a protein having ShcC activity) but differ in sequence from the sequence of SEQ ID NO:1 and FIG. 6, due to degeneracy in the genetic code. As one example, DNA sequence polymorphisms within the nucleotide sequence of ShcC may result in silent mutations which do not affect the amino acid sequence. Variations in one or more nucleotides may exist among individuals within a population due to natural allelic variation. Any and all such nucleic acid variations are within the scope of the invention. DNA sequence polymorphisms may also occur which lead to changes in the amino acid sequence of ShcC. These amino acid polymorphisms are also within the scope of the present invention.

Another aspect of the invention provides a nucleic acid molecule which hybridizes under stringent conditions, preferably high stringency conditions to a nucleic acid molecule which comprises a sequence which encodes ShcC having the amino acid sequence shown in SEQ ID NO:2 and FIG. 7. Appropriate stringency conditions which promote DNA hybridization are known to those skilled in the art, or can be found in Current Protocols in Molecular Biology, John Wiley & Sons, N.Y. (1989), 6.3.1–6.3.6. For example, 6.0×sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

It will be appreciated that the invention includes nucleic acid molecules encoding truncations of ShcC, and analogs of ShcC as described herein. It will further be appreciated that variant forms of the nucleic acid molecules of the invention which arise by alternative splicing of an mRNA corresponding to a cDNA of the invention are encompassed by the invention.

An isolated nucleic acid molecule of the invention which comprises DNA can be isolated by preparing a labelled nucleic acid probe based on all or part of the nucleic acid sequence shown in SEQ ID NO:1 and FIG. 6. For example, the probe may be based on the nucleotides encoding the CH1 region which correspond to about amino acids 190 to 376 in SEQ ID NO:1 and FIG. 7; the nucleotides encoding the SH2 domain which correspond to about amino acids 377 to 472 in SEQ ID NO:1 and FIG. 7; and the nucleotides encoding the PTB domain which correspond to about amino acids 29 to 189 in SEQ ID NO:1 and FIG. 7. The labelled nucleic acid probe is used to screen an appropriate DNA library (e.g. a cDNA or genomic DNA library). For example, a cDNA library can be used to isolate a cDNA encoding a protein having ShcC activity by screening the library with the labelled probe using standard techniques. Alternatively, a genomic DNA library can be similarly screened to isolate a genomic clone encompassing a gene encoding a protein having ShcC activity. Nucleic acids isolated by screening of a cDNA or genomic DNA library can be sequenced by standard techniques.

An isolated nucleic acid molecule of the invention which is DNA can also be isolated by selectively amplifying a nucleic acid encoding ShcC using the polymerase chain reaction (PCR) methods and cDNA or genomic DNA. It is possible to design synthetic oligonucleotide primers from the nucleotide sequence shown in SEQ ID NO:1 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding ShcC into an appropriate vector which allows for transcription of the cDNA to produce an RNA molecule which encodes a protein which exhibits ShcC activity. For example, a cDNA can be cloned downstream of a bacteriophage promoter, (e.g. a T7 promoter) in a vector, cDNA can be transcribed in vitro with T7 polymerase, and the resultant RNA can be isolated by conventional techniques.

Nucleic acid molecules of the invention may be chemically synthesized using standard techniques. Methods of chemically synthesizing polydeoxynucleotides are known, including but not limited to solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a protein having ShcC activity can be accomplished by expressing the cDNA in an appropriate host cell by standard techniques, and testing the ability of the expressed protein to bind to proteins containing the consensus sequence pTyr-(hydrophobic/Glu)-(hydrophobic/Met/Tyr)-(Ile/Leu/Met) [SEQ ID NO:14], and to associate with proteins containing the consensus sequence Asn-Pro-X-pTyr [SEQ ID NO:12]. A cDNA having the biological activity of ShcC can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of a ShcC protein may be determined using computer software designed for the purpose, such as PC/Gene (IntelliGenetics Inc., Calif.). The intron-exon structure and the transcription regulatory sequences of the gene encoding a ShcC protein may be identified by using a nucleic acid molecule of the invention encoding ShcC to probe a genomic DNA clone library. Regulatory elements can be identified using standard techniques. The function of the elements can be confirmed by using these elements to express a reporter gene such as the lacZ gene which is operatively linked to the elements. These constructs may be introduced into cultured cells using conventional procedures or into non-human transgenic animal models. In addition to identifying regulatory elements in DNA, such constructs may also be used to identify nuclear proteins interacting with the elements, using techniques known in the art.

The sequence of a nucleic acid molecule of the invention may be inverted relative to its normal presentation for transcription to produce an antisense nucleic acid molecule. An antisense nucleic acid molecule may be constructed using chemical synthesis and enzymatic ligation reactions using procedures known in the art.

II. ShcC Proteins of the Invention

ShcC proteins are predominantly expressed in the adult brain. ShcC proteins are also characterized by their ability to bind through their SH2 domains to proteins containing the consensus sequence pTyr-(hydrophobic/Glu)-hydrophobic/Met/Tyr)-(Ile/Leu/Met) [SEQ ID NO:14]. Examples of proteins containing the consensus sequence pTyr-(hydrophobic/Glu)-(hydrophobic/Met/Tyr)-(Ile/Leu/Met) [SEQ ID NO:14] include EGF and PDGF. ShcC proteins also associated through their PTB domain with proteins containing the consensus sequence Asn-Pro-X-pTyr [SEQ ID NO:12] where X is any amino acid. In particular, ShcC associates in vitro with autophosphorylated receptors for nerve growth factor (NGF) and EGF.

The amino acid sequence of ShcC is shown in SEQ. ID NO. 2 or in FIG. 7. ShcC contains a number of well-characterized regions including a carboxy terminal src homology 2 (SH2) domain (amino acids 377 to 472) containing the sequence GDFLVR which is highly conserved among SH2 domains; a phosphotyrosine binding domain (amino acids 29 to 189); and a central proline-rich region (CH1) (amino acids 190 to 376) containing a Grb2 binding site (Tyr-Val-Asn-Thr), SEQ ID NO:13.

In addition to the full length ShcC amino acid sequence (SEQ. ID. NO:2), the proteins of the present invention include truncations of ShcC, and analogs, and homologs of ShcC and truncations thereof as described herein. Truncated proteins may comprise peptides of between 3 and 450 amino acid residues, ranging in size from a tripeptide to a 450 mer polypeptide. For example, a truncated protein may comprise the SH2 domain (amino acids 377 to 472); the PTB domain (amino acids 29 to 189); or the CH1 region (amino acids 190to376).

The truncated proteins may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end.

The proteins of the invention may also include analogs of ShcC as shown in SEQ. ID. NO. 2, and/or truncations thereof as described herein, which may include, but are not limited to ShcC (SEQ. ID. NO. 2), containing one or more amino acid substitutions, insertions, and/or deletions. Amino acid substitutions may be of a conserved or non-conserved nature. Conserved amino acid substitutions involve replacing one or more amino acids of the ShcC amino acid sequence with amino acids of similar charge, size, and/or hydrophobicity characteristics. When only conserved substitutions are made the resulting analog should be functionally equivalent to ShcC (SEQ. ID. NO. 2). Non-conserved substitutions involve replacing one or more amino acids of the ShcC amino acid sequence with one or more amino acids which possess dissimilar charge, size, and/or hydrophobicity characteristics. By way of example, Tyr 304 may be replaced to create an analog which does not bind to the adaptor protein Grb2.

One or more amino acid insertions may be introduced into ShcC (SEQ. ID. NO. 2). Amino acid insertions may consist of single amino acid residues or sequential amino acids ranging from 2 to 15 amino acids in length. For example, amino acid insertions may be used to destroy the PTB domain sequences so that ShcC can no longer bind proteins containing the consensus sequence Asn-Pro-X-pTyr [SEQ ID NO:12].

Deletions may consist of the removal of one or more amino acids, or discrete portions (e.g. one or more of the SH2 domain, PTB domain, and CH1 region) from the ShcC (SEQ. ID. NO. 2) sequence. The deleted amino acids may or may not be contiguous. The lower limit length of the resulting analog with a deletion mutation is about 10 amino acids, preferably 100 amino acids.

It is anticipated that if amino acids are replaced, inserted or deleted in sequences outside the carboxy terminal src homology 2 (SH2) domain and the phosphotyrosine binding (PTB) domain, and the motif corresponding to the Crb2-binding site in the central CH1 region that the resulting ShcC protein will bind to proteins containing the consensus sequence pTyr-(hydrophobic/Glu)-(hydrophobic/Met/Tyr)-(Ile/Leu/Met) [SEQ ID NO:14] and associate with proteins containing the consensus sequence Asn-Pro-X-pTyr [SEQ ID NO:12].

The proteins of the invention also include homologs of ShcC (SEQ. ID. NO. 2) and/or truncations thereof as described herein. Such ShcC homologs include proteins whose amino acid sequences are comprised of the amino acid sequences of ShcC regions from other species that hybridize under stringent hybridization conditions (see discussion of stringent hybridization conditions herein) with a probe used to obtain ShcC. These homologs will generally have the same regions which are characteristic of ShcC, namely a carboxy terminal SH2 domain, a PTB domain and a motif corresponding to the Grb2-binding site in a central CH1 region. It is anticipated that, outside of the well-characterized regions of ShcC specified herein (i.e. SH2 domain, PTB domain etc), a protein comprising an amino acid sequence which is about 40% similar, preferably 50 to 60% similar, with the amino acid sequence shown in SEQ ID NO:2 will exhibit Shc C activity.

The invention also contemplates isoforms of the protein of the invention. An isoform contains the same number and kinds of amino acids as the protein of the invention, but the isoform has a different molecular structure. The isoforms contemplated by the present invention are those having the same properties as the protein of the invention as described herein.

The present invention also includes ShcC protein conjugated with a selected protein, or a selectable marker protein (see below) to produce fusion proteins. Further, the present invention also includes activated i.e. phosphorylated ShcC proteins of the invention. Additionally, immunogenic portions of ShcC and ShcC related proteins are within the scope of the invention.

The ShcC proteins of the invention may be prepared using recombinant DNA methods. Accordingly, the nucleic acid molecules of the present invention having a sequence which encodes a ShcC protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used.

The invention therefore contemplates a recombinant expression vector of the invention containing a nucleic acid molecule of the invention, and the necessary regulatory sequences for the transcription and translation of the inserted protein-sequence. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. The necessary regulatory sequences may be supplied by the native ShcC and/or its flanking regions.

The invention further provides a recombinant expression vector comprising a DNA nucleic acid molecule of the invention cloned into the expression vector in an antisense orientation. That is, the DNA molecule is linked to a regulatory sequence in a manner which allows for expression, by transcription of the DNA molecule, of an RNA molecule which is antisense to the nucleotide sequence of SEQ ID NO:1. Regulatory sequences linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

The recombinant expression vectors may be introduced into host cells to produce a transformant host cell. "Transformant host cells" include host cells which have been transformed or transfected with a recombinant expression vector of the invention. The terms "transformed with", "transfected with", "transformation" and "transfection" encompass the introduction of nucleic acid (e.g. a vector) into a cell by one of many standard techniques. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

Alternatively, the proteins of the invention may also be expressed in non-human transgenic animals such as, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

N-terminal or C-terminal fusion proteins comprising a ShcC protein of the invention conjugated with other molecules, such as proteins may be prepared by fusing, through recombinant techniques, the N-terminal or C-terminal of a ShcC protein, and the sequence of a selected protein or selectable marker protein with a desired biological function. The resultant fusion proteins contain ShcC protein fused to the selected protein or marker protein as described herein. Examples of proteins which may be used to prepare fusion proteins include immunoglobulins, glutathione-S-transferase (GST), hemagglutinin (HA), and truncated myc. The present inventors have made GST fusion proteins containing the SH2 domain and PTB domain of ShcC (See Example 1).

Phosphorylated or activated ShcC proteins of the invention may be prepared using the method described in Reedijk et al. (The EMBO Journal 11(4):1365, 1992). For example, tyrosine phosphorylation may be induced by infecting bacteria harbouring a plasmid containing a nucleotide sequence of the invention or fragment thereof, with a λgt11 bacteriophage encoding the cytoplasmic domain of the Elk tyrosine kinase as a LacZ-Elk fusion. Bacteria containing the plasmid and bacteriophage as a lysogen are isolated. Following induction of the lysogen, the expressed peptide becomes phosphorylated by the Elk tyrosine kinase.

III. Nucleotide Probes

The nucleic acid molecules of the invention allow those sklled in the art to construct nucleotide probes for use in the detection of nucleic acid sequences in biological materials. Suitable probes include nucleic acid molecules based on nucleic acid sequences encoding at least 6 sequential amino acids from regions of the ShcC protein as shown in SEQ. ID NO:2, FIG. 2(A) and FIG. 7. For example, a probe may be based on the nucleotides encoding the SH2 domain, CH1 region, or PTB domain of ShcC. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode ShcC proteins. The nucleotide probes may also be useful in the diagnosis of disorders of the nervous system.

IV. Antibodies

ShcC proteins of the invention can be used to prepare antibodies specific for the proteins. Antibodies can be prepared which bind a distinct epitope in an unconserved region of the protein. An unconserved region of the protein is one which does not have substantial sequence homology to other proteins, for example the regions outside the SH2 and PTB domains of ShcC as described herein. A region from one of the well-characterized domains (e.g. SH2 domain) can be used to prepare an antibody to a conserved region of a ShcC protein. Antibodies having specificity for a ShcC protein may also be raised from fusion proteins created by expressing fusion proteins in bacteria as described herein.

Conventional methods can be used to prepare the antibodies. For example, by using a peptide of a ShcC protein, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, [e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a ShcC protein as described herein.

The term "antibody" includes antibody fragments which also specifically react with a protein, or peptide having the activity of ShcC. Antibodies can be fragmented using conventional techniques and the fragments screened for utility as described above. For example, F(ab')$_2$ fragments can be generated by treating antibody with pepsin. The resulting F(ab')$_2$ fragment may be treated to reduce disulfide bridges to produce Fab' fragments.

Chimeric antibody derivatives, i.e., antibody molecules that combine a non-human animal variable region and a human constant region are also within the scope of the invention. Chimeric antibody molecules include, for example, the antigen binding domain from an antibody of a mouse, rat, or other species, with human constant regions. Standard methods may be used to make chimeric antibodies containing the immunoglobulin variable region which recognizes the gene product of ShcC antigens of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a ShcC protein of the invention may be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against ShcC proteins of the invention may also be prepared by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). Alternatively, a SCID-hu mouse, for example the model developed by Genpharm, can be used to produce antibodies, or fragments thereof.

Antibodies specifically reactive with a ShcC protein, or derivatives, such as enzyme conjugates or labeled derivatives, may be used to detect ShcC proteins in various biological materials, for example they may be used in any known immunoassays which rely on the binding interaction between an antigenic determinant of a ShcC protein and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify ShcC protein in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect ShcC, to localise it to particular cells and tissues in the brain and to specific subcellular locations, and to quantitate the level of expression.

Cytochemical techniques known in the art for localizing antigens using light and electron microscopy may be used to detect a ShcC protein. Generally, an antibody of the invention may be labelled with a detectable substance and ShcC may be localised in tissues and cells based upon the presence of the detectable substance. Examples of detectable substances include various enzymes such as biotin, alkaline phosphatase, β-galactosidase, or acetylcholinesterase; fluorescent materials such as fluorescein; luminescent materials such as luminol; and, radioactive materials such as radioactive iodine $I^{125,}$ $I^{131}$ or tritium. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against ShcC. By way of example, if the antibody having specificity against ShcC is a rabbit IgG antibody, the second antibody may be goat anti-rabbit gamma-globulin labelled with a detectable substance as described herein.

Where a radioactive label is used as a detectable substance, ShcC may be localized by radioautography. The results of radioautography may be quantitated by determining the density of particles in the radioautographs by various optical methods, or by counting the grains.

V. Utility of the Nucleic Acid Molecules and Proteins of the Invention

As discussed herein, ShcC is predominantly expressed in the adult brain and is characterized by its ability to bind through its SH2 domain to phosphotyrosine-containing peptides and receptors, and associate through its PTB domain in vitro with autophosphorylated receptors for nerve growth factor (NGF) and epidermal growth factor (EGF). Therefore, ShcC has a role in regulating proliferation, differentiation, activation and metabolism of cells of the nervous system. Therefore, the above described methods for detecting nucleic acid molecules of the invention and ShcC proteins, can be used to monitor proliferation, differentiation, activation and metabolism of cells of the nervous system by detecting and localizing ShcC proteins and nucleic acid molecules encoding ShcC proteins. It would also be apparent to one skilled in the art that the above described methods may be used to study the developmental expression of ShcC and, accordingly, will provide further insight into the role of ShcC in the nervous system.

The finding that ShcC has an important role in the regulation of signalling pathways that control gene expression, cell proliferation, differentiation, activation, and metabolism in the nervous system permits the identification of substances which affect ShcC regulatory systems and which may be used in the treatment of conditions involving perturbation of signalling pathways. The term "ShcC regulatory system" refers to the interaction of a ShcC protein and or a part or activated form thereof, with proteins containing the consensus sequence pTyr-(hydrophobic/Glu)-(hydrophobic/Met/Tyr)-(Ile/Leu/Met) [SEQ ID NO:14], including EGF and PDGF; proteins containing the consensus sequence Asn-Pro-X-pTyr [SEQ ID NO:12] where X is any amino acid, including NGF and Trk; and, adaptor proteins such as Grb2 through association with particular motifs of ShcC (i.e. YYNS (aa 221 to 224 of SEQ ID NO:2) and YVNT [SEQ ID NO:13]), to form complexes thereby activating a series of regulatory pathways that control gene expression, cell division, cytoskeletal architecture and cell metabolism particularly in the nervous system. Such pathways include the Ras pathway, the pathway that regulates the breakdown of polyphosphoinositides through phospholipase C, and PI-3-kinase activated pathways.

Substances which affect a ShcC regulatory system include substances comprising or consisting of the SH2 domain, PTB domain, and/or Grb2 binding site of SchC, or comprising or consisting of one or more of the consensus sequences pTyr-(hydrophobic/Glu)-(hydrophobic/Met/Tyr)-(Ile/Leu/Met) [SEQ ID NO:14], and Asn-Pro-X-pTyr. A substance which affects a ShcC regulatory system may also be identified using the above described methods for detecting nucleic acid molecules and ShcC proteins, and by comparing the pattern and level of expression of ShcC proteins in the presence and absence of the substance.

Further, substances which affect a ShcC regulatory system can be identified based on their ability to bind to the ShcC protein or the activated ShcC protein. Therefore, the invention also provides methods for identifying substances which are capable of binding to a ShcC protein or an activated ShcC protein. In particular, the methods may be used to identify substances which are capable of binding to the SH2 and PTB domains of ShcC proteins, including proteins containing the consensus sequence pTyr-(hydrophobic/Glu)-(hydrophobic/Met/Tyr)-(Ile/Leu/Met) [SEQ ID NO:14] and proteins containing the consensus sequence Asn-Pro-X-pTyr [SEQ ID NO:12]. Substances which, bind to an activated ShcC protein such as a ShcC protein having a phosphorylated tyrosine in the Grb2-binding site may also be identified. The substances identified using the methods of the invention may be isolated, cloned and sequenced using conventional techniques.

Substances which can bind with ShcC proteins or activated ShcC proteins may be identified by reacting a ShcC protein with a substance which potentially binds to the ShcC protein or activated ShcC protein, under conditions which permit the formation of substance-ShcC protein complexes and assaying for substance-ShcC protein complexes, for free substance, or for non-complexed ShcC protein or activated ShcC protein, or for activation of ShcC protein. Conditions which permit the formation of substance-ShcC protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against ShcC protein or the substance, or labelled ShcC protein, or a labelled substance may be utilized. The antibodies, proteins, or substances may be labelled with a detectable substance as described above.

Substances which bind to a ShcC protein of the invention may be identified by assaying for activation of the ShcC protein i.e. by assaying for phosphorylation of the tyrosine residues of the protein.

ShcC protein, or the substance used in the method of the invention may be insolubilized. For example, a ShcC protein or substance may be bound to a suitable carrier such as agarose, cellulose, dextran, Sephadex, Sepharose, car-boxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized protein or substance may be prepared by reacting the material with a suitable insoluble carrier using known chemical or physical methods, for example, cyanogen bromide coupling.

The invention also contemplates a method for assaying for an agonist or antagonist of the binding of a ShcC protein or activated ShcC protein with a substance which is capable of binding with ShcC protein or activated ShcC protein. The agonist or antagonist may be an endogenous physiological substance or it may be a natural or synthetic substance. Substances which may be used in the method include proteins containing the consensus sequence pTyr-(hydrophobic/Glu)-(hydrophobic/Met/Tyr)-(Ile/Leu/Met) [SEQ ID NO:14] and proteins containing the consensus sequence Asn-Pro-X-pTyr [SEQ ID NO:12]. In particular, the substance may be a transmembrane or cytoplasmic tyrosine kinase such as EGFR, T cell receptor, TrkA, B, or C, or a portion or fusion protein thereof. EGFR, T cell receptor, TrkA, B, or C, may be activated i.e. phosphorylated, using the methods described for example by Reedijk et al. (The EMBO Journal, 11(4):1365, 1992) for producing a tyrosine phosphorylated protein. The substance may also be an adaptor protein such as Grb2, or a part of or fusion protein of Grb2. EGFR, T cell receptor, Trk receptors, Grb2, or a portion or fusion protein thereof may be prepared using conventional methods. Other substances which are capable of binding with ShcC protein or activated ShcC protein may be identified using the methods set forth herein.

In accordance with a preferred embodiment, a method is provided which comprises providing a known concentration of a Shc protein, incubating the Shc protein with a transmembrane or cytoplasmic tyrosine kinase or part thereof, and a suspected agonist or antagonist under conditions which permit the formation of complexes between the Shc protein and the transmembrane or cytoplasmic tyrosine kinase or part thereof, assaying for complexes, for free Shc, for non-complexed Shc proteins, or for activation of ShcC proteins, and comparing to a control to determine if the substance is an agonist or antagonist of the interaction of the ShcC protein and substance. Conditions which permit the formation of protein complexes and methods for assaying for complexes, for free ShcC proteins, for non-complexed ShcC proteins, or for activation of ShcC protein are described herein.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of ShcC protein with a substance which is capable of binding to the ShcC protein. Thus, the invention may be used to assay for a substance that competes for the same binding site of a ShcC protein.

The reagents suitable for applying the methods of the invention to identify substances that affect a ShcC regulatory system may be packaged into convenient kits providing the necessary materials packaged into suitable containers. The kits may also include suitable supports useful in performing the methods of the invention.

The substances identified by the methods described herein, antibodies, and antisense nucleic acid molecules of the invention may be used for modulating a ShcC regulatory system, and accordingly may be used in the treatment of conditions involving perturbation of a ShcC signalling system. In particular, the substances may be particularly useful in the treatment of neurodegenerative conditions and conditions involving trauma and injury to the nervous system, for example Alzheimer's disease, Parkinson's disease, Huntington's disease, demylinating diseases, such as multiple sclerosis, amyotrophic lateral sclerosis, bacterial and viral infections of the nervous system, deficiency diseases, such as Wernicke's disease and nutritional polyneuropathy, progressive supranuclear palsy, Shy Drager's syndrome, multistem degeneration and olivo ponto cerebellar atrophy, peripheral nerve damage, trauma and ischemia resulting from stroke. The substances may also be useful in the treatment of tumors of the nervous system, such as neuroblastomas and they may be particularly effective in reversing malignant properties of the tumors.

The substances and antibodies may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The activity of the substances, antibodies, antisense nucleic acid molecules, and compositions of the invention may be confirmed in animal experimental model systems. For example, models of peripheral nervous system damage include animals having damaged axons, such as axotomized facial neurons (Sendtner et al. Nature, 345, 440–441, 1990); models of neurodegenerative conditions include the MPTP model as described in Langston J. W. et al., Symposium of Current Concepts and Controversies in Parkinson's Disease, Montebello, Quebec, Canada, 1983 and Tatton W. G. et al., Can. J. Neurol. Sci. 1992, 19), and models of traumatic and non-traumatic peripheral nerve damage include animal stroke models such as the one described in MacMillan et al. Brain Research 151:353–368 (1978)).

The invention also provides methods for studying the function of a ShcC protein. Cells, tissues, and non-human animals lacking in shcC expression or partially lacking in shcC expression may be developed using recombinant expression vectors of the invention having specific deletion or insertion mutations in the shcC gene. For example, the PTB domain, SH2 domain, or CH1 region may be deleted. A recombinant expression vector may be used to inactivate or alter the endogenous gene by homologous recombination, and thereby create a shc C deficient cell, tissue or animal.

Null alleles may be generated in cells, such as embryonic stem cells by deletion mutation. A recombinant shcC gene may also be engineered to contain an insertion mutation which inactivates shcC Such a construct may then be introduced into a cell, such as an embryonic stem cell, by a technique such as transfection, electroporation, injection etc. Cells lacking an intact shcC gene may then be identified, for example by Southern blotting, Northern Blotting or by assaying for expression of ShcC using the methods described herein. Such cells may then be fused to embryonic stem cells to generate transgenic non-human animals deficient in shcC. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on shcC expression.

The following non-limiting examples are illustrative of the present invention:

EXAMPLE 1

The following materials and methods were utilized in the investigations outlined in Example 1:

Materials and Methods

Cell Culture and Reagents

A431 and AF6295 cells (Axl-transformed NIH/3T3 cells, provided by Dr. Edison Liu, UNC Chapel Hill) were grown in Dulbecco's modified Eagle's medium (DMEM) containing 10% fetal bovine serum, penicillin and streptomycin in the presence of 5% $CO_2$. PC12 cells (kindly provided by Dr. Patricia Maness-Tidwell, UNC Chapel Hill) were grown in DMEM containing 15% horse serum, 5% fetal bovine serum, penicillin and streptomycin in the presence of 10% $CO_2$. Epidermal growth factor (EGF) was provided by Dr. H. Shelton Earp. PY20 and EGFR antibodies were purchased from Transduction Laboratories. HRP-linked antiglutathione-S-transferase (GST) antibody was purchased from Santa Cruz Biotechnology. The ldash129 genomic library was provided by Dr. Janet Rossant, Mount Sinai Hospital. The mouse brain and NIH/3T3 cDNA libraries were purchased from Stratagene.

Cloning of ShcB

Approximately 1.4×10⁶ recombinations from a λDASH 129 genomic library were screened in duplicate with a [³²P]-labelled polymerase chain reaction (PCR) fragment corresponding to the human ShcA SH2 domain at reduced stringency (50% formamide, 5×SSC, 5×Denhardts, 0.5% SDS, 200 mg/ml salmon sperm DNA at 37° C.). Filters (Hybond, Amersham) were washed twice at room temperature in 2×SSC/0.1% SDS followed by a single 20 min. wash at 42° C. Filters were exposed for 3 days. An NIH/3T3 library (Stratagene) was screened as above with an exon fragment from the shcB genomic clone in order to isolate a partial shcB cDNA.

Cloning of ShcC

A mouse brain library (Stratagene) (approximately 1×10⁶ recombinants) was screened with a [³²P]-labelled PCR fragment corresponding to the shcB cDNA under high stringency resulting in the isolation of a second shcA-related cDNA ShcC. Further 5' sequence of ShcC was obtained by 5' RACE using 5' RACE-ready cDNA derived from mouse brain (Clonetech).

Northern Blot and Reverse Transcriptase-mediated PCR (RT-PCR) Analysis of ShcC Expression Mouse multiple tissue Northern blots were purchased form Clonetech and probed with [³²P]-labelled PCR fragments under high stringency (50% formamide/10× Denhardts/5×SSC/1% SDS/100 mg/ml salmon sperm DNA at 42° C. overnight. The filter was washed twice at 44° C. with 2×SSC/0.1% SDS 30 min. each followed by a single wash at 55° C. in 0.2×SSC/0.1% SDS for 30–40 min. RT-PCR was performed as previously described (22). Briefly, 5 μg total RNA from the indicated tissues was reverse transcribed in the presence of random hexamers using the Superscript MuMLV reverse transcriptase (BRL) in a final volume of 20 μl. A portion of this cDNA reaction was PCR amplified in the presence of ShcC primers (5'-GTCATTGGCTCCATTCGGACA [SEQ ID NO:15]; 3'-ATCCTGGCATCCGGGGCTCT [SEQ ID NO:16]) and then fractionated on a 3% NuSeive GTG agarose gel (FMC BioProducts).

Antibody Production, in vitro Binding and Western Blot Analysis

The Shc SH2 domain has been previously described (1). Glutathione-S-transferase (GST) fusion proteins of the SH2 domains of ShcB and ShcC were constructed by PCR amplification of the regions encoding mouse ShcB and ShcC SH2 domains and subcloning into the pGEX2T bacterial expression vector (Pharmacia). A fusion construct of the PTB domain of ShcC was constructed by PCR amplification of the corresponding region of ShcC as shown in FIG. 1. Fragments were subcloned into pGEX4T1. The fidelity of the inserts was confirmed by sequencing. Bacterial cultures containing the fusion constructs were grown in 2×YT media containing 100 μg/ml ampicillin and then induced with 0.1 mM isopropyl b-D-thiogalactopyranoside for 3–5 hours at 37° C. Bacteria were pelleted then lysed in phosphate buffered saline/1% Triton X-100/1% Tween 20/1 mM dithiothriotol supplemented with 10 μg/ml leupeptin and 10 μg/ml aprotinin. Antibodies were raised against fusion proteins of the SH2 domain ShcC as described for ShcA (1). In vitro binding experiments and Western blotting were performed as described in (1).

Peptide Selection by SH2 Domains

The selectivity of the isolated SH2 domains of ShcB and ShcC were determined using a degenerate peptide library screen as previously described (4, 23).

Experimental Results

Identification of Two Mouse Genes Related to shcA

During the course of screening a mouse genomic library with a human shcA probe, a genomic clone was isolated which was derived from a novel shc-like gene (shcB). Sequence analysis of the genomic shcB clone identified an exon encoding part of an SH2 domain similar to that found in human ShcA. However, several lines of evidence suggested that the protein product of this genomic clone was distinct from ShcA. In particular, the predicted sequence of the mouse ShcB SH2 domain showed only 67% identity to the mouse ShcA SH2 domain. Sequence comparison of shcB suggests that it is the mouse gene corresponding to the human shc-like gene, sck.

While pursuing the isolation of shcB cDNAs, a mouse brain cDNA library was screened with a shcB probe. Analysis of one cDNA clone isolated in this screen gave a predicted protein sequence distinct from both mouse ShcA and ShcB suggesting the presence of a third member of the shc gene family (ShcC). The ShcC clone contained an open reading frame encoding 474 amino acids with a potential initiating methionine. This sequence apparently encodes the p55 isoform of ShcC described below.

Comparison of the predicted protein sequences of mouse ShcA and ShcC (FIG. 1) indicates that these proteins are highly related (59% identity). ShcC has a 96 amino acid C-terminal sequence that shares 69% identity with the ShcA SH2 domain and possesses all the residues characteristic of an SH2 domain, including amino acids required for phosphotyrosine binding (24, 25). At its N-terminus, ShcC has a region of 163 amino acids that is closely related to the ShcA PTB domain (78% identity). The most highly conserved sequences between ShcA and ShcC are those corresponding to the ShcA SH2 and PTB domains, suggesting that ShcC might also have two distinct phosphotyrosine-recognition modules that bind activated tyrosine kinases. The central CH1 regions of ShcA and ShcC are less similar (40% identity) but contain at least three well-conserved motifs. A motif corresponding to the ShcA tyrosine phosphorylation site and Grb2-binding site (Tyr313-Val-Asn-Ile in mouse ShcA, aa 313–316 of SEQ ID NO:6) is present in ShcC and human Sck (Tyr-Val-Asn-Thr, aa 317–320 of SEQ ID NO:7). In addition, a motif with the consensus Tyr-Tyr-Asn-X-X-Pro-X-Lys-X-Pro-Pro [SEQ ID NO:17] (where X represents a variable amino acid) is present in the CH1 regions of ShcA, Sck, ShcC and Drosophila Shc. The mammalian Shc proteins have an additional conserved motif (Lys/Arg-Asp-Leu-Phe-Asp-Met-Arg/Lys-Pro-Phe-Glu-Asp-Ala-Leu-Lys/Arg, SEQ ID NO:18) in the CH1 region. Based on the precedent set by the binding of Grb2 to the Tyr317 phosphorylation site of human Shc, it is probable that the conserved motifs in the CH1 regions of the Shc family of proteins contact downstream targets. In addition, the variable sequences present in the CH1 regions may impart specificity in downstream signalling.

ShcC is Preferentially Expressed in the Brain

Figure 2B:
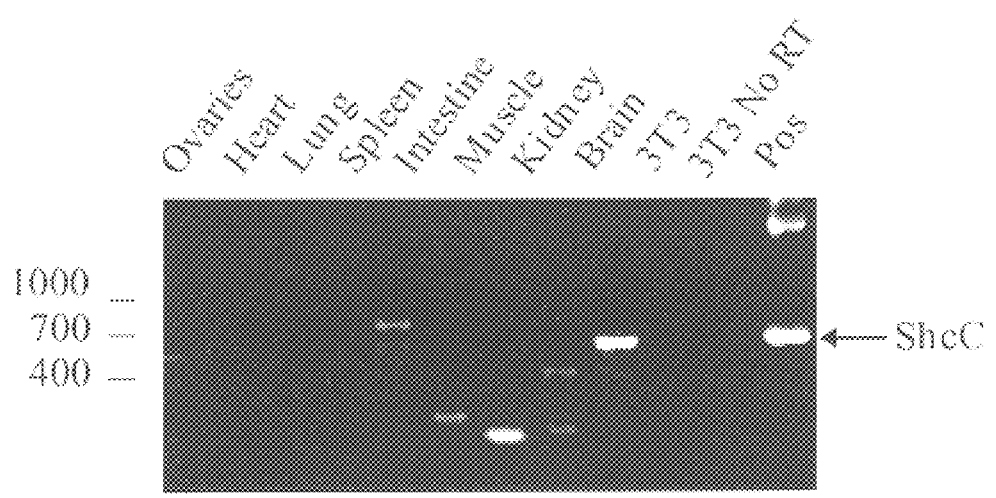
FIG. 2B shows immunoblots of a RT-PCR analysis showing ShcC RNA is specifically expressed in brain tissues.

Previous studies have determined that shcA is widely expressed. Therefore, the expression profile of ShcC was investigated. Northern blot analysis of poly-A+RNA from various mouse tissues indicated that ShcC is specifically expressed in the brain as two transcripts of approximately 10 and 9.8 kb (FIG. 2A). Similarly, reverse transcriptase-mediated PCR (RT-PCR) indicated that ShcC is only detectably expressed in the brain (FIG. 2B).

Figure 3A:
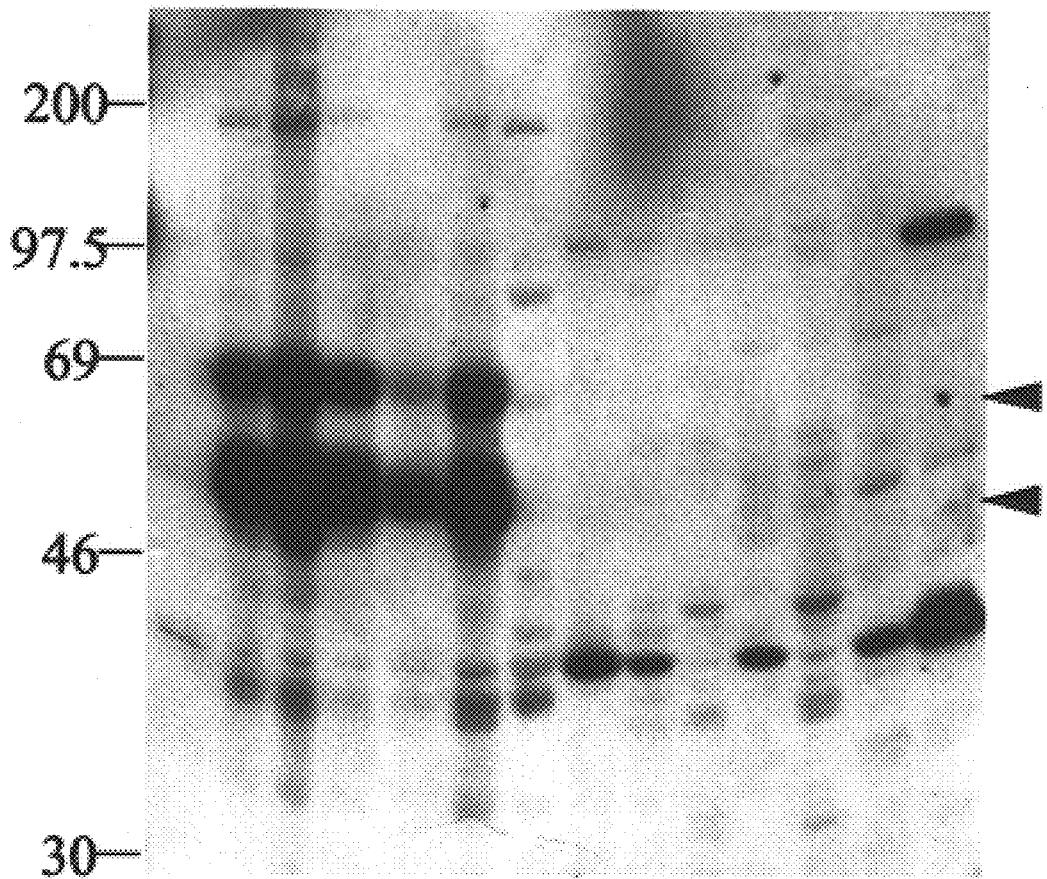
FIG. 3A shows immunoblots of the fractionation of total mouse protein from mouse tissues fractionated on SDS-PAGE and probed with affinity purified ShcC antibody.
Figure 3B:
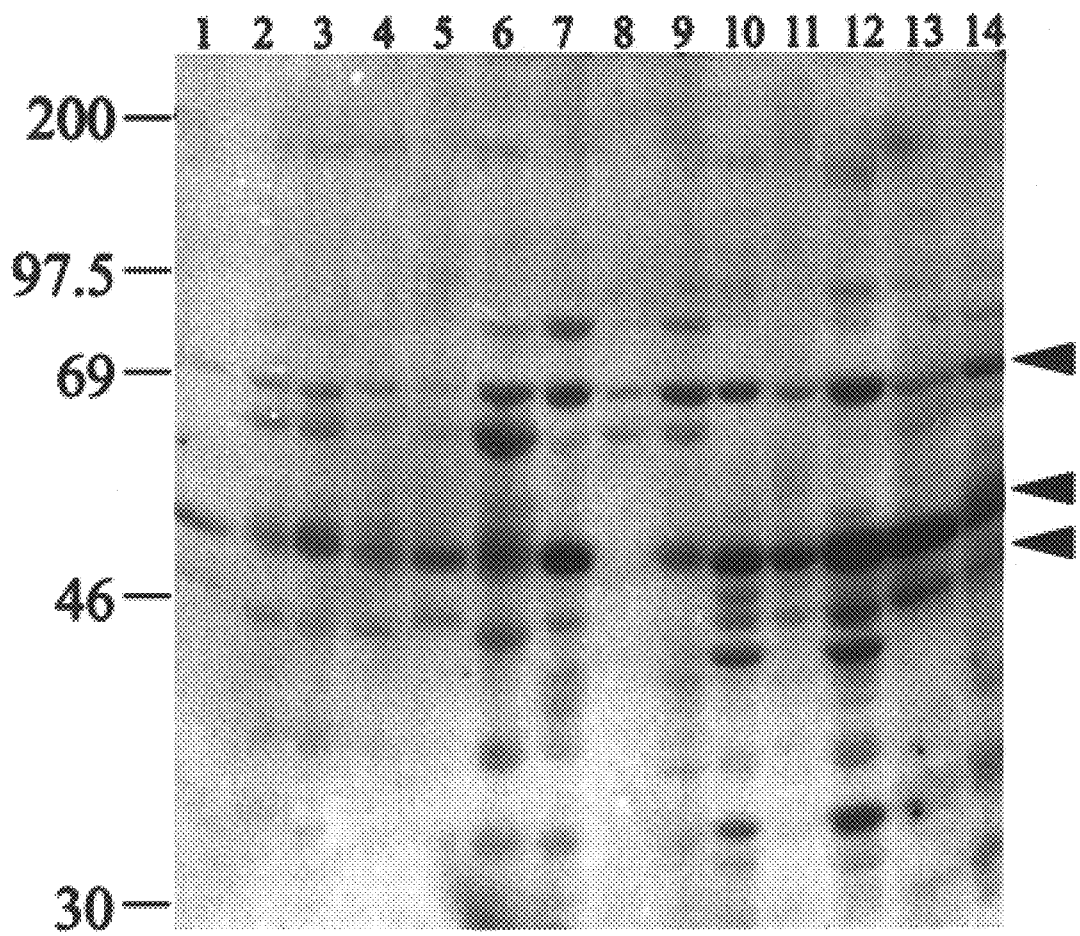
FIG. 3B is the same as FIG. 3B except purified anti-Shc antibody was used at 1–2 mg/ml.

These results suggest that the expression of ShcC is highly restricted. To investigate this point in more detail, antibodies were raised against a GST fusion protein containing the ShcC SH2 domain. Affinity-purified anti-ShcC antibodies specifically detected two major protein species of 55 kDa and 69 kDa in lysates from mouse cerebellum, cerebrum, for brain, eye and spinal cord which were absent from heart, intestine, kidney, liver, lung, pancreas, spleen and stomach (FIG. 3A). These bands were specifically competed away by incubating the antibody with fusion protein, but not with GST alone, and were not detected with pre-immune serum. In addition, a larger immunoreactive polypeptide of 100 kDa was detected in a number of cell lines of neural origin (data not shown). The 55 kDa protein recognized by the anti-ShcC antibody is apparently encoded by the open reading frame within the cloned ShcC cDNA. Since no 5' in-frame stop codons have yet been identified, it is likely that additional 5' sequences exist which may encode the 69 and 100 kDa immunoreactive proteins. Indeed, shcA encodes multiple protein isoforms (p46, p52, and p66) that differ solely in the extent of their N-terminal sequences and are all detected using antibodies directed against the ShcA SH82 domain (FIG. 3B). The ShcC antibodies did not recognize specific proteins in several tissues which are known to express ShcA indicating that these antibodies are specific and do not cross-react with ShcA polypeptides (FIG. 3). These results indicate that ShcC proteins are primarily expressed in the nervous system consistent with the expression pattern of ShcC RNA. In contrast, ShcA proteins are widely expressed but are only present at low levels in the central nervous system (FIG. 3A and FIG. 3B).

The ShcB and ShcC SH2 Domains Bind Specific Phosphopeptides and Phosphotyrosine-containing Proteins To test whether the ShcC SH2 domain binds specific phosphotyrosine-containing peptides, GST-SH2 fusion proteins were used to examine binding selectivity using a degenerate phosphopeptide library screen (4,26). The specificity of the ShcC SH2 domain was compared with that of ShcA and ShcB. As previously described, the human ShcA SH2 domain selected peptides with the consensus sequence pTyr-(hydrophobic/Glu)-X-(Ile/Leu/Met), with X indicating little or no selectivity at the +2 position. The ShcB and ShcC SH2 domains gave similar, but distinct, profiles compared to ShcA (Table 1). In contrast to ShcA, ShcB and ShcC showed a preference for hydrophobic amino acids at the +2 position. ShcB selected Met and Ile at +2, whereas ShcC selected Met and Tyr. As with ShcA, both ShcB and ShcC SH2 domains selected hydrophobic amino acids at the +1 and +3 position. However, the ShcB SH2 domain bound preferentially to Phe and Tyr at +3 which was not seen with the other Shc family members. These data suggest that the ShcA, ShcB and ShcC SH2 domains are similar in their binding specificity for phosphotyrosine-containing peptides, as anticipated from their close sequence relationship. However, there are discernable differences in their selectivity for residues at the +1 to +3 positions, suggesting that their binding to cellular phosphoproteins is not identical.

Figure 4A:
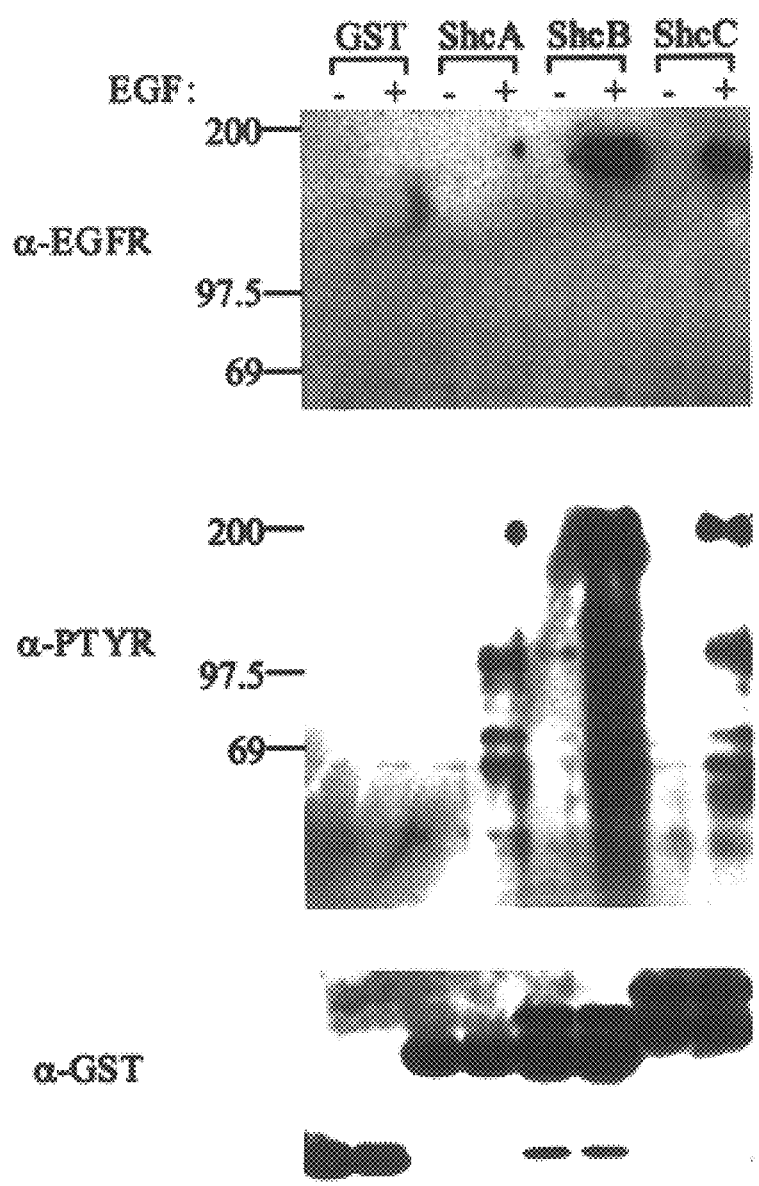
FIG. 4A shows immunoblots of binding experiments with SH2 domains of ShcB and ShcC and tyrosine phosphorylated proteins in lysates from A431 cells grown in the presence or absence of EGF.
Figure 4B:
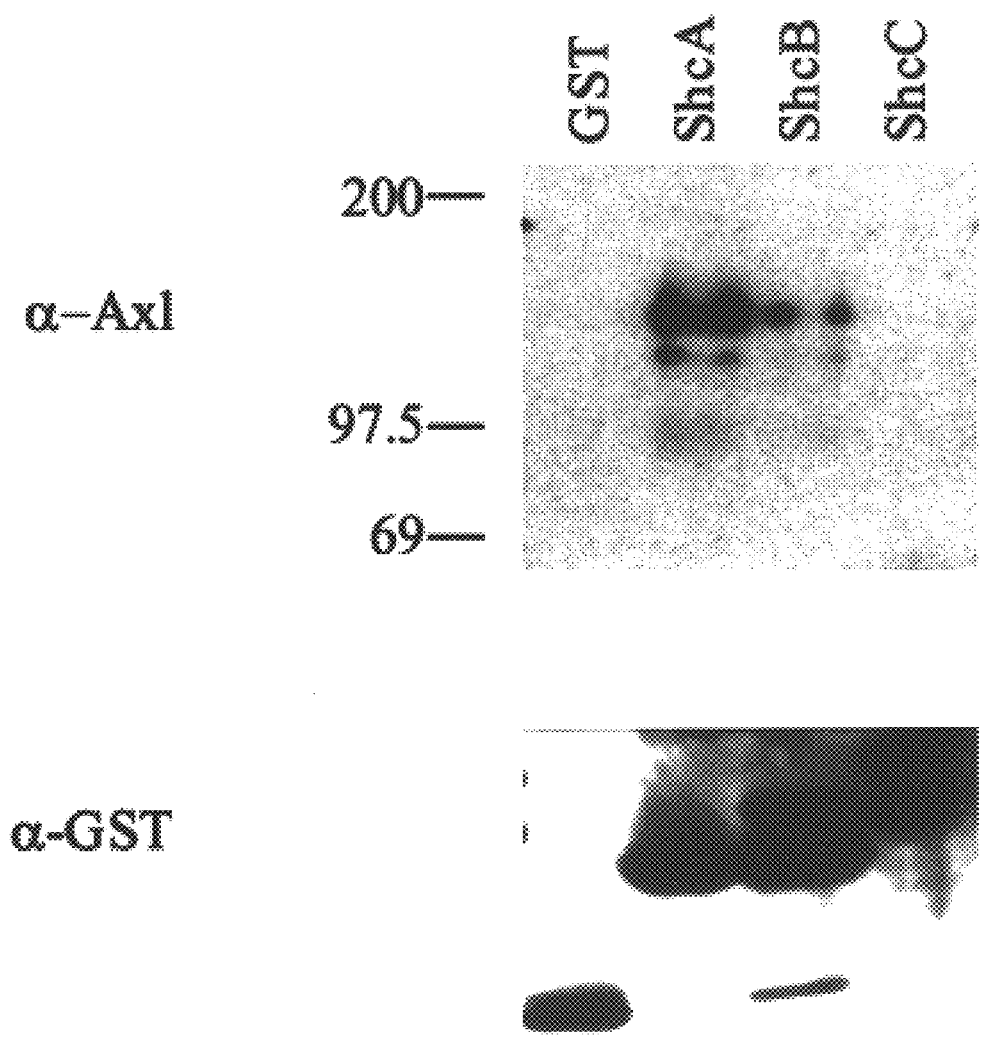
FIG. 4B shows immunoblots of binding experiments with SH2 domains of ShcB and ShcC and tyrosine phosphorylated proteins in lysates from NIH/3T3 cells transformed by the Axl tyrosine kinase receptor.

The ability of the SH2 domains of the Shc family members to bind phosphotyrosine-containing proteins in cell lysates was therefore investigated directly. The ShcA, ShcB and ShcC SH2 domains all bound specifically to the autophosphorylated EGF-receptor in EGF-stimulated cells. However the ShcB SH2 domain appeared to bind more efficiently than ShcC, which in turn was more efficient than ShcA (FIG. 4). In contrast, in lysates from NIH/3T3 cells which overexpress the Axl RTK (22), the ShcA SH2 domain bound most tightly to autophosphorylated Axl, followed by the ShcB SH2, which was more effective than ShcC SH2 (FIG. 4). These results are consistent with the data from the phosphopeptide library selection, indicating that the SH2 domains of the different Shc family members have similar binding specificities, but also display differences which may affect their relative abilities to recognize specific phosphotyrosine-containing proteins in vivo.

ShcC Has a Functional PTB Domain

ShcC has sequences related to the ShcA PTB domain. To test whether this region might function as a phosphotyrosine-binding module, the presumptive PTB domain of ShcC was expressed as a GST fusion protein, and assessed for its ability to bind to phosphotyrosine-containing proteins in lysates of EGF-stimulated cells. As shown in FIG. 4C, the ShcC PTB domain bound to the autophosphorylated EGF-receptor, and a number of other tyrosine phosphorylated proteins in lysates of EGF-stimulated cells. Comparison of phosphoproteins bound by the ShcC PTB and SH2 domains, showed that they recognized overlapping but distinct sets of proteins. These results suggest that the ShcC PTB domain is active in binding to specific phosphotyrosine-containing proteins.

Figure 5A:
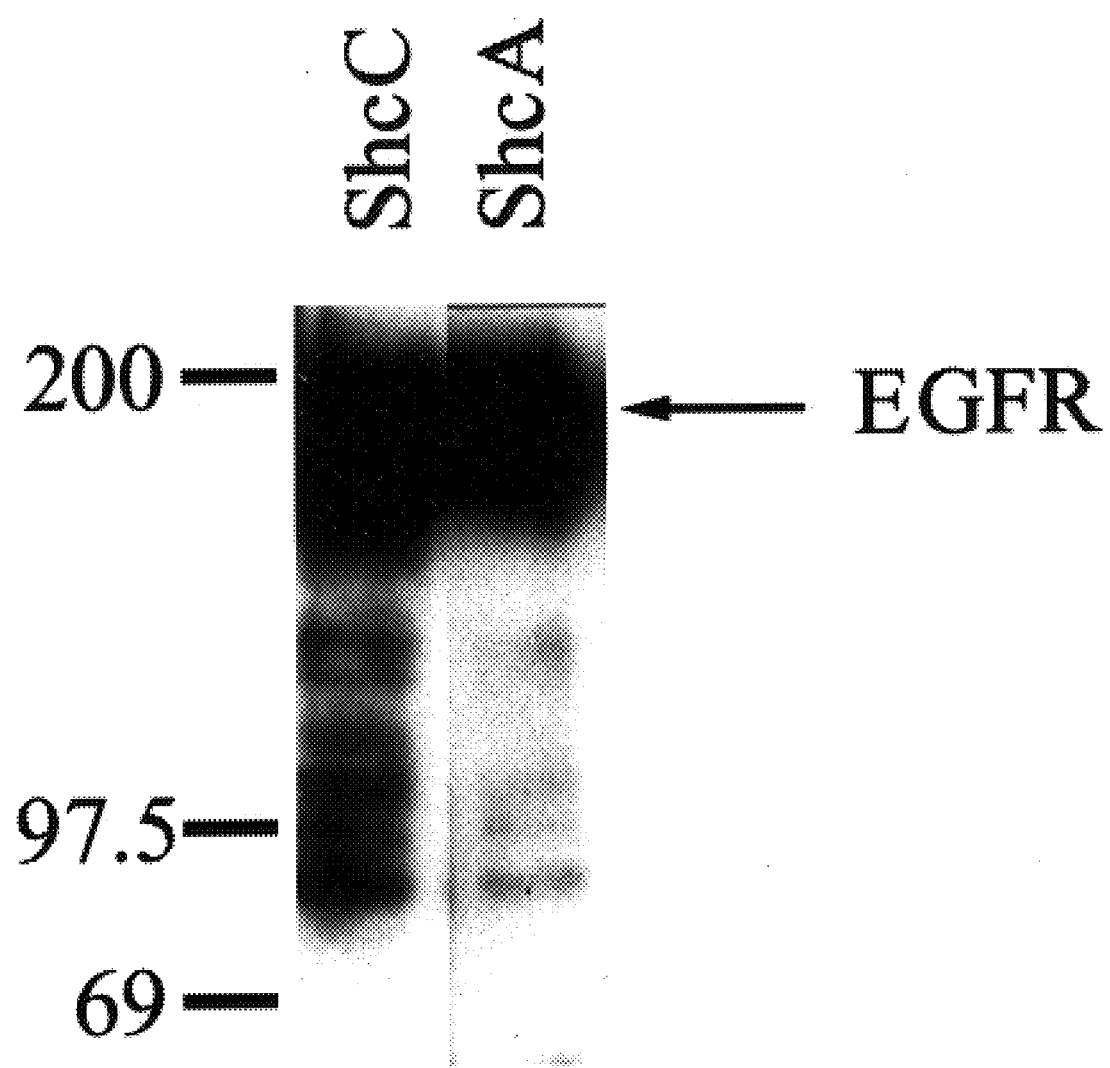
FIG. 5A shows immunoblots of binding experiments with PTB domains of ShcA and ShcC and tyrosine phosphorylated proteins in lysates from A431 cells grown in the presence or absence of EGF.
Figure 5B:
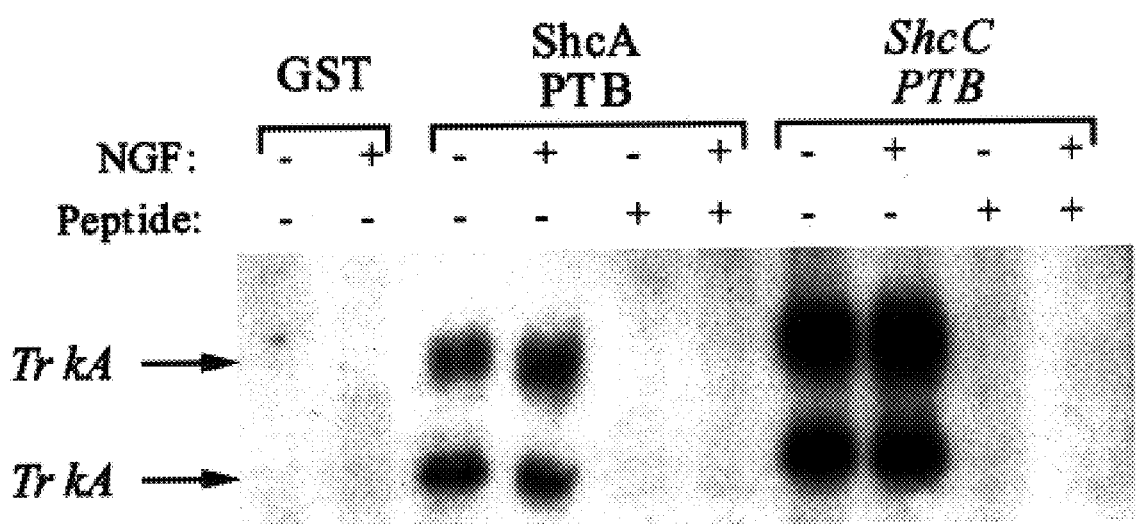
FIG. 5B shows immunoblots of binding experiments with SH2 domains of ShcB and ShcC and tyrosine phosphorylated proteins in lysates of from NIH/3T3 cells which overexpress TrkA.

Since ShcC is expressed primarily in neural derived tissues, ShcC coupling to neural specific receptor tyrosine kinases was tested. ShcA had been shown to specifically interact with the TrkA receptor (21, 29) which is expressed in neural crest-derived sensory neurons (30). This interaction occurs through the PTB domain of ShcA which binds to the motif Ile-Glu-Asn-Pro-Gln-pTyr in the juxtamembrane regions of activated TrkA. The ShcC PTB domain also bound in vitro to autophosphorylated TrkA, present in lysates of NIH3T3 cells that ectopically express TrkA (FIG. 5B). This interaction was blocked by inclusion of a phosphopeptide modeled on the Tyr-490 justamembrane autophosphorylation site of TrkA. These results demonstrate that ShcC can specifically interact with neural receptors and that the ShcC PTB domain recognized phosphorylated sequences with an Asn-Pro-X-pTyr motif.

Discussion of Experimental Results

A Shc Gene Family

Previous work has suggested that ShcA adaptor proteins play a central role in transducing signals from transmembrane and cytoplasmic tyrosine kinases (1, 16). Several biochemical attributes of ShcA apparently contribute to its ability to couple to multiple tyrosine kinases. Notably, mammalian ShcA and its Drosophila homolog are the only proteins identified thus far that contain both functional SH2 and PTB domains. The potential significance of the shcA gene is underscored by its conservation between invertebrates and mammals. Here, two additional shc-related genes have been identified some of the properties of their protein products have been analyzed. The observation that the mammalian genome encodes a family of Shc-related proteins raises the possibility that Shc polypeptides are more diverse in function than previously anticipated. Since there are multiple mammalian shc genes, the novel genes have been designated as shcB and shcC and the original shc gene as shcA.

Modular Construction of Shc Family Members

ShcA proteins have two distinct phosphotyrosine-recognition modules, the SH2 and PTB domains, that flank a central region that contains the principal ShcA tyrosine phosphorylation site. Based on the observation that Grb2 binds the Tyr317 phosphorylation site of human ShcA, it is probable that the central CH1 region of ShcA provides binding sites for downstream targets. This possibility suggests a model in which the PTB and SH2 domains couple ShcA to upstream tyrosine kinases, while the CH1 domain is an effector region that provides an output to cytoplasmic signalling proteins.

ShcA and ShcC share a common structural organization. ShcC has an amino-terminal PTB domain that is 78% identical to the ShcA PTB domain. Although the mechanisms by which the ShcA PTB domain recognizes Leu/Ile-X-Asn-Pro-X-pTyr [SEQ ID NO:10] sites is not known, an Arg residue has been identified in the ShcA PTB (Arg175 of p52shc) that is critical for binding of phosphorylated ligands and might play a role in phosphotyrosine-recognition. This Arg is conserved in ShcC (FIG. 1). These observations suggest that the PTB domains of ShcB and ShcC will bind specific phosphotyrosine sites as observed for ShcA PTB. Indeed, the ShcC PTB domain associated in vitro with the autophosphorylated EGF-receptor and with a number of additional phosphotyrosine-containing proteins in EGF-stimulated cells (FIG. 4C).

Both ShcB and ShcC have a C-terminal SH2 domain which shows similar in vitro binding specificity as compared to the ShcA SH2 domain. However, there are differences in the binding properties of the SH2 domains of the three Shc family members which suggest they may have distinct, albeit related, in vivo binding activities. Taken together, these results indicate that ShcC has functional SH2 and PTB domains and might thereby interact with a wide range of tyrosine kinases and phosphotyrosine-containing proteins.

The central effector region of the Shc family members is less well conserved, sharing only 32–40% identity. However, several short motifs are conserved in the CH1 domains of all three proteins which might provide contact sites for distinct effectors. Both ShcC and Sck have potential Grb2-binding sites (Tyr-Val-Asn-Thr, SEQ ID NO:13)) which are similar to the known Grb2 binding site of human ShcA (Tyr-Val-Asn-Val, aa 317–320 of SEQ ID NO:7) (FIG. 1). It is possible that this sequence in ShcC binds an SH2 domain other than, or in addition to Grb2. Another motif in the CH1 region, Tyr-Tyr-Asn-X-X-Pro-X-Lys-X-Pro-Pro [SEQ ID NO:17] is conserved in the three mammalian Shc family members and is also present in Drosophila Shc which lacks a Grb2-binding site. It is not known whether the Tyr residues in this motif are phosphorylated. However, this element is a strong candidate for an effector binding site. The more variable residues in the CH1 domains of Shc family members may play a structural role or may allow these presumptive adaptors to contact novel effectors.

Signalling Functions of ShcC

A striking difference between ShcC and ShcA is in their pattern of expression. ShcC RNA and protein is specifically expressed in the mouse brain. Although shcB RNA is also predominantly found in the brain, it is more widely expressed than shcC. However, both ShcB and ShcC are distinguished from ShcA, which is very broadly expressed. These data raise the possibility that the new Shc family members, especially ShcC, may play a specific role in signalling from tyrosine kinases in the nervous system. Both the TrkB and TrkC receptor tyrosine kinases, that are activated by brain-derived neurotrophic factor and neurotrophin-3 or -4/5, possess a juxtamembrane motif corresponding to the Tyr 490 PTB-binding site in TrkA, which is recognized by the ShcC PTB domain. Hence, ShcC may participate in signalling from these neurotrophin receptors, as well as other tyrosine kinases such as Pyk2 which are primarily expressed in the brain (32).

EXAMPLE 2

Figure 8A:
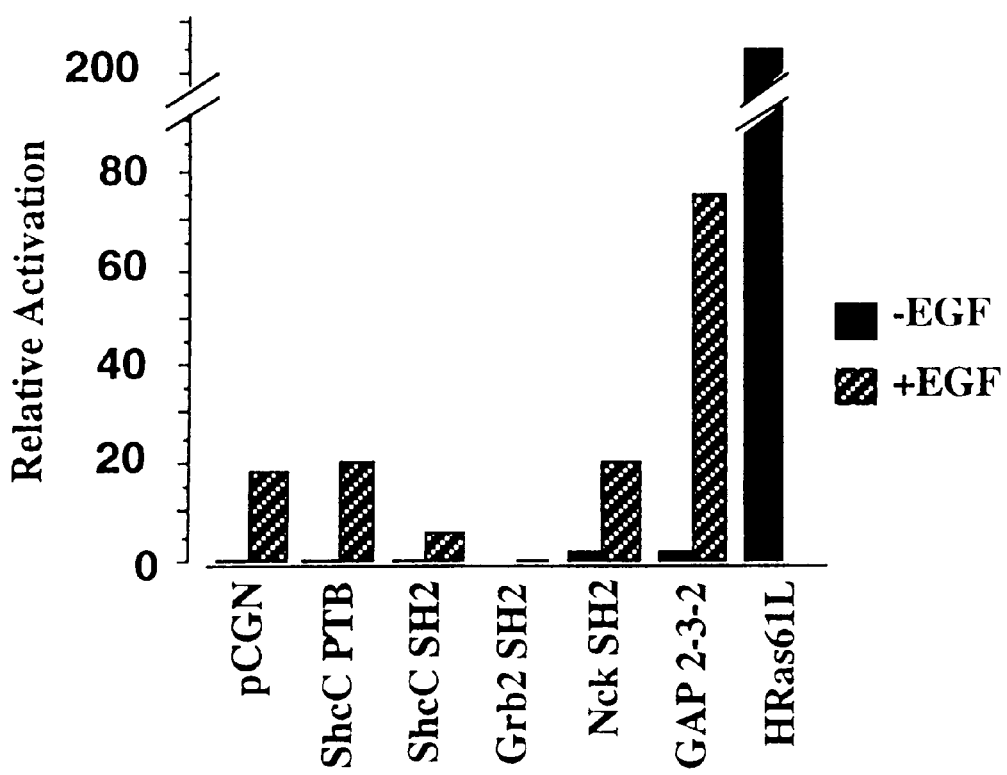
FIG. 8A is a bar graph showing the effect of dominant negatives on Gal-Elk activation by EGF in 293T cells.
Figure 8B:
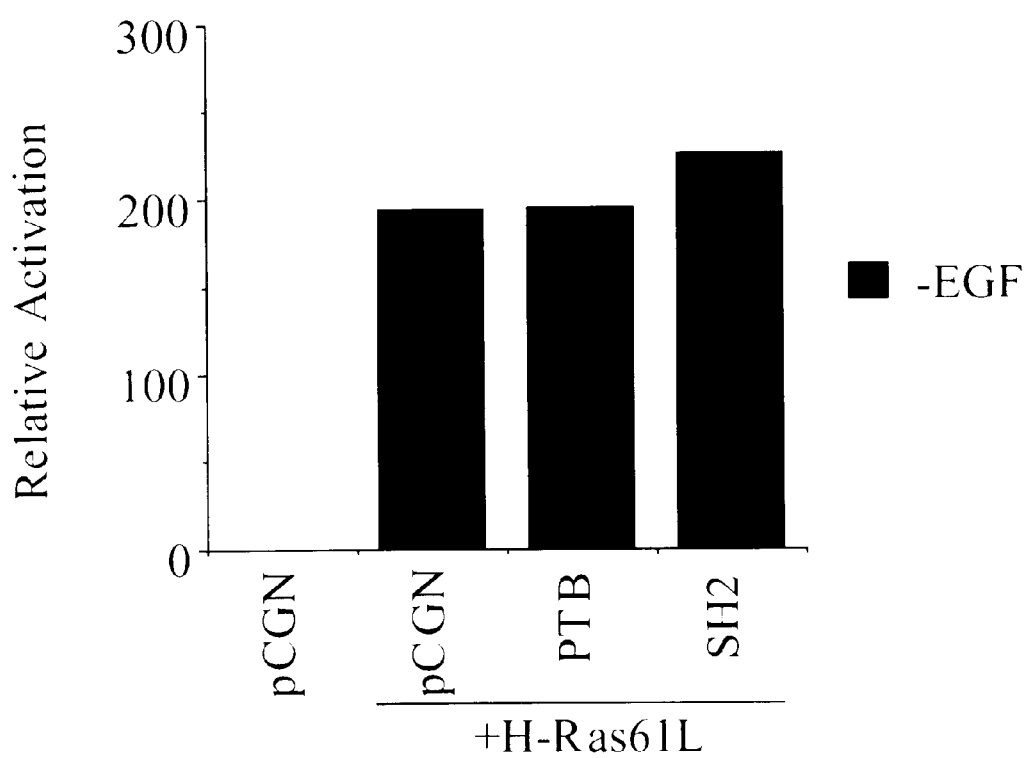
FIG. 8B is a bar graph showing the effect of dominant negatives on Gal-Elk activation by activated Hras61L.

I. Expression of the Isolated ShcC SH2 Domain But Not the PTB Domain Blocks MAPK Activation by EGF In order to assess the effect of expression of the isolated SH2 and PTB domains of ShcC, the ability of these isolated domains to block MAPK activation by the EGFR in transient transcription assays was tested. The transcription assays used were as previously described (33). MAPK activation was measured by activation of the Elk-1 transcription factor which is a substrate of MAPK. Activation of Elk-1 was determined by cotransfection of 293T cells with Gal4-Elk-1, a construct encoding a fusion protein consisting of the Gal4-DNA binding domain and the Elk-1 transcriptional activation domain (which contains the MAPK phosphorylation sites), and Gal4-Luc, which contains the luciferase gene driven by a minimal promoter containing five tandem Gal4 DNA-binding sites (35). Together, these constructs were cotransfected along with the ShcC mutants into 293T cells using calcium phosphate precipitation. Twenty-four hours after transfection, the cells were starved in medium containing 0.1% serum for 16 hrs. On the following day cells were stimulated with EGF (100 ng/ml) for 4–5 hrs or left unstimulated and then lysed. Cell lysates were then measured for luciferase activity in a luminometer (33). Expression of the ShcC SH2 domain blocked the EGF-induced MAPK activity by approximately 50%; however, the PTB domain did not appear to significantly affect the EGF-induced MAPK activity (FIG. 8A). In order to assess specificity of these constructs at blocking signaling, the effect of expression of other SH2 domains on MAPK activation by EGF was tested. The Grb2 SH2 completely inhibited EGF-induced MAPK activity. In fact the base line MAPK activity in the absence of EGF was significantly reduced as compared to vector transfected cells. As expected, expression of the SH2-SH3-SH2 region of RasGAP did not inhibit MAPK activation. In addition, the ShcC SH2 and PTB domains did not inhibit the activation of MAPK by H-Ras61L, a constitutively activated form of Ras which is independent of exchange factors and therefore refractory to the effects of Shc dominant-negative proteins (FIG. 8B). These results suggest that the isolated domains of ShcC act as dominant negative proteins and specifically inhibit EGFR signaling.

Figure 9:
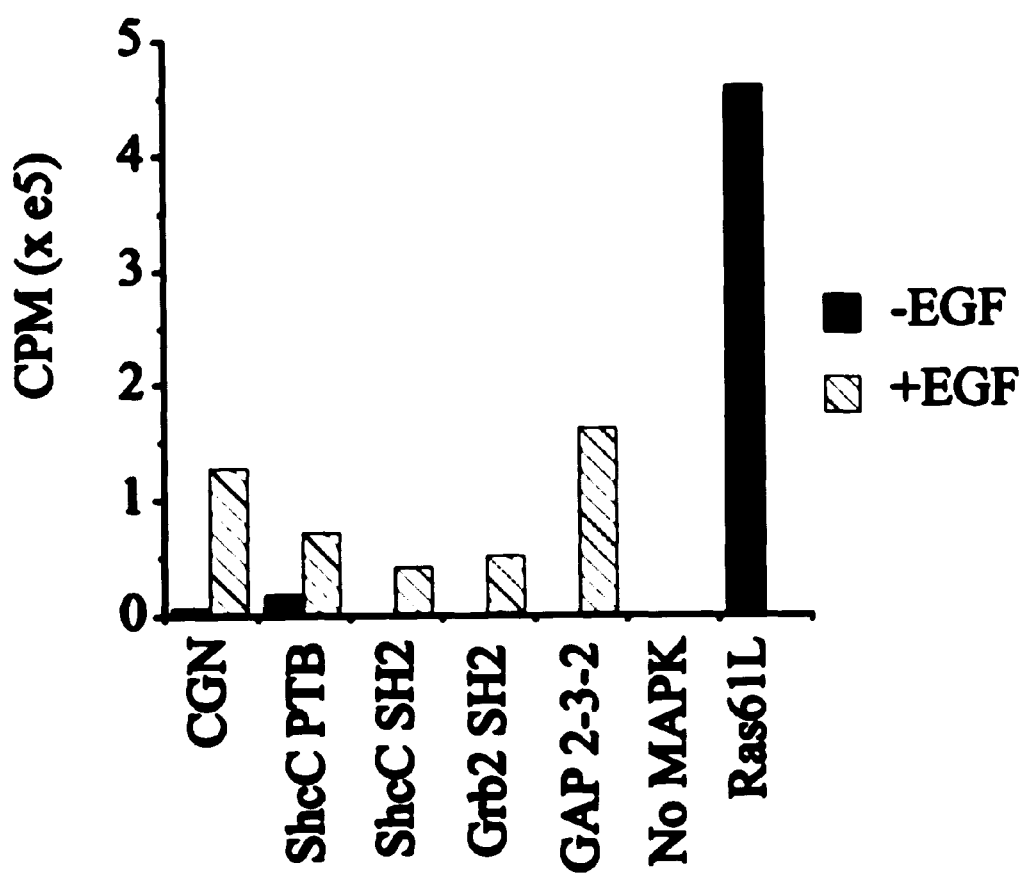
FIG. 9 is a bar graph showing the effect of ShcC dominant negative proteins on the in vitro kinase activity of HA-MapK.

To further examine the inhibition by these dominant negative proteins, their effect on the actual in vitro kinase activity of MAPK with and without EGF stimulation was tested (FIG. 9). In these experiments, the ShcC dominant negatives were cotransfected with a plasmid encoding an HA epitope-tagged MAPK. Again, 24 hrs after transfection the cells were serum starved and then stimulated the following morning with EGF (100 ng/ml) for 10 min. or left unstimulated. The lysates were clarified and the MAPK immunoprecipitated with anti-HA monoclonal antibodies. The immunoprecipitates were subjected to an in vitro kinase assay with the MAPK substrate myelin basic protein (MBP). Samples were then fractionated on SDS-PAGE, and transferred to Immobilon filters. The filters were then dried and MBP phosphorylation quantitated using a phosphorimager. As shown in FIG. 9, the SH2 domains of ShcC and Grb2 were effective inhibitors of MAPK activation by EGF. Furthermore, in contrast to the Gal-Elk assay, the PTB domain appeared to have a slight inhibitory effect on MAPK activation. In addition, the negative control of GAP 2-3-2 did not inhibit activity.

II. Expression of the ShcC SH2 and PTB Domains in EGFR-transformed NIH/3T3 Cells Blocks Transformation Overexpression of the EGFR in NIH/3T3 cells results in ligand dependent transformation (30, 46). However, a number of receptor tyrosine kinases are transforming in the absence of ligand due to their high overexpression which likely leads to constitutive dimerization and kinase activation (26, 36, 39). This finding is due to the fact that cells are initially selected for uptake of the construct expressing the RTK and then the selected cells are passaged, allowed to grow to confluence then assessed for the presence of morphologically transformed cells. This approach allows for the selection of cells overexpressing the RTK and is referred to as a secondary focus-formation assay. The advantage of a secondary focus-formation assay is that one can identify weakly transforming genes by virtue of the enrichment of cells expressing the gene. When tested in a secondary focus-formation assay, a number of RTKs including the EGFR, TrkA (NGFR), Axl and Rek were found to transform cells in the absence of their respective ligand (26, 39).

Figure 10:
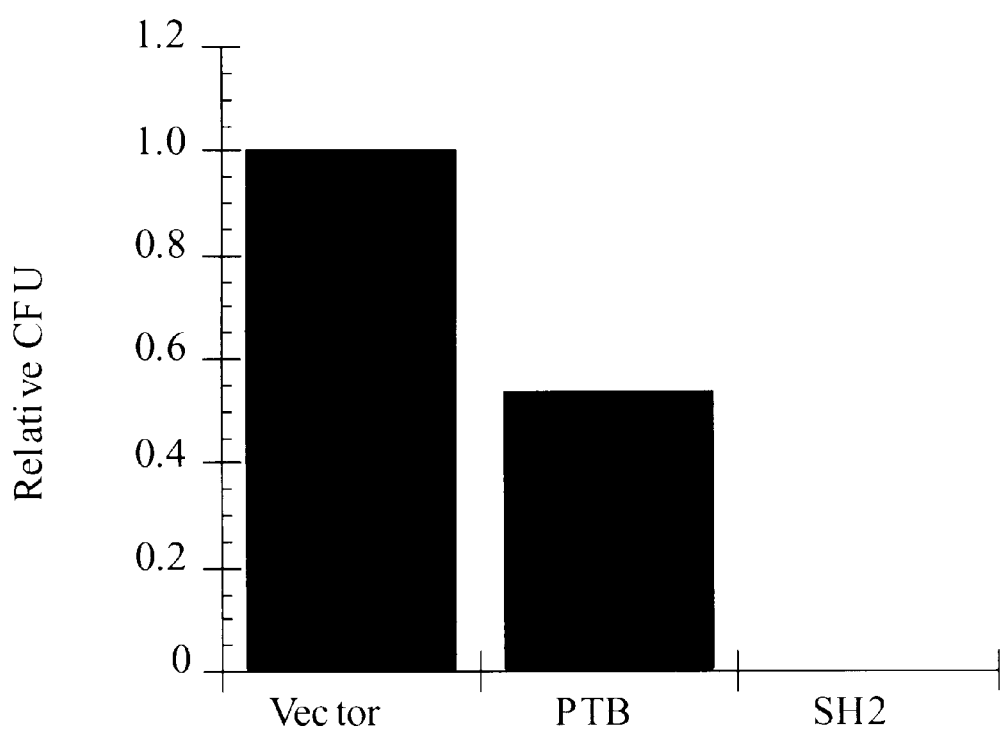
FIG. 10 is a bar graph showing quantitation of colony formation of NIH/3T3 cells transformed by overexpression of EGFR transfected with either vector, PTB, or SH2.

An EGFR-transformed cell line was established from a secondary focus-formation assay. Once EGFR-transformed foci formed, the cells were continually passaged to allow for overgrowth of the EGFR-transformed cells. These cells express high levels of activated EGFR as assessed by Western blot analysis with both anti-phosphotyrosine and anti-EGFR antibodies. Using these EGFR-transformed cells, the effect of overexpression of the ShcC PTB or SH2 domains on the transformed properties of these cells was tested. EGFR cells transfected with vector alone grew well in soft agar (FIG. 10). Expression of the ShcC PTB domain partially blocked the soft agar growth of these cells. However, expression of the SH2 domain dramatically reduced the number of soft agar colonies obtained. These results suggest that the SH2 domain is an effective inhibitor of the long term function of the EGFR, i.e. it blocked EGFR transformation. The PTB domain also inhibited transformation but did not appear to be as effective. These results suggest that the isolated domains of ShcC are able to inhibit EGFR transformation supporting the use of these domains as potential therapeutic agents.

Figure 11:
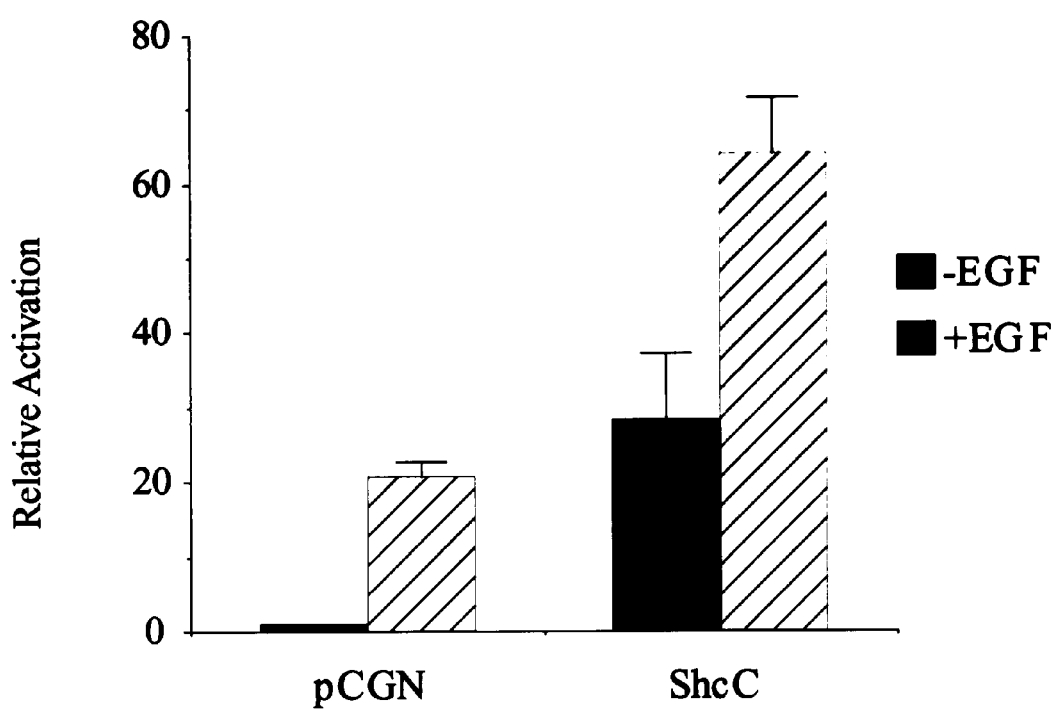
FIG. 11 is a bar graph showing MAPK activation in response to EGF treatement of 293T cells cotransfected with either pCGN-ShcC or empty vector along with the Gal-Elk reporter constructs.

III. Cells Which Express the SH2 Domain of ShcC Are Resistant to Transformation By the EGFR To further assess the ability of the isolated SH2 and PTB domains to block EGFR function, NIH/3T3 cell lines were established which overexpress either the SH2 or PTB domains of ShcC. These cells were then tested for their ability to be transformed by the wild type EGFR in a secondary focus-formation assay as described above. While vector transfected cells were transformed quite well by the EGFR, the SH2 expressing cells were transformed less efficiently. In addition, expression of the PTB domain partially inhibited EGFR transforming activity. These results suggest that the SH2 domain of ShcC can block interaction of Shc proteins with the EGFR thereby interfering with receptor signaling. Coupled with the results discussed in II above, the SH2 domain and PTB domain of ShcC appear to inhibit transformation, i.e., focus-formation, as well as revert the transformed phenotype, i.e., soft agar growth. However, the SH2 domain appeared more potent at inhibition of EGFR function suggesting that the interaction of the SH2 domain with the EGFR plays a more crucial role in linking the receptor with Shc than does the PTB domain. IV. Full Length ShcC Stimulates Gal-Elk Activation To assess the activity of full length ShcC, 293T cells were cotransfected with either pCGN-ShcC or empty vector along with the Gal-Elk reporter constructs to measure MAPK activation in response to EGF treatment. As shown in FIG. 11, expression of full length ShcC stimulates MAPK activity to the level seen with EGF stimulation of vector control cells. Furthermore, EGF treatment leads to an even greater level of MAPK activation, approximated 3 fold higher than is seen in EGF treated vector control cells. These results suggest that overexpression of ShcC can activate the MAPK pathway as has been reported for ShcA overexpression (32).

These results demonstrate that the SH2 domain of ShcC can both inhibit as well as revert some of the transformed properties resulting from overexpression of the EGFR. In addition, expression of the PTB domain has some inhibitory effects on EGFR transformation but the level of inhibition is not as substantial as with the SH2 domain. These findings suggest that the isolated domains of ShcC may function as effective therapeutic agents for inhibiting or possibly reverting the transformed phenotype of certain tumors. For example, glioblastomas have a high frequency of EGFR amplification and rearrangement suggesting an involvement of the EGFR in the progression of this tumor. Expression of the ShcC SH2 and/or PTB domains in these tumor cells may lead to effective reversion of some of the malignant properties of this tumor.

EXAMPLE 3

I. Mutations in the PTB Domain of ShcC Affect the Binding to Tyrosine Phosphorylated Proteins A panel of mutations in the ShcC PTB domain have been characterized for their effect on phosphotyrosine binding. The results of the analysis are shown in Table 1.

II. Purified GST-PTB Domain of ShcC Specifically Binds Phospholipids in vitro

Figure 12:
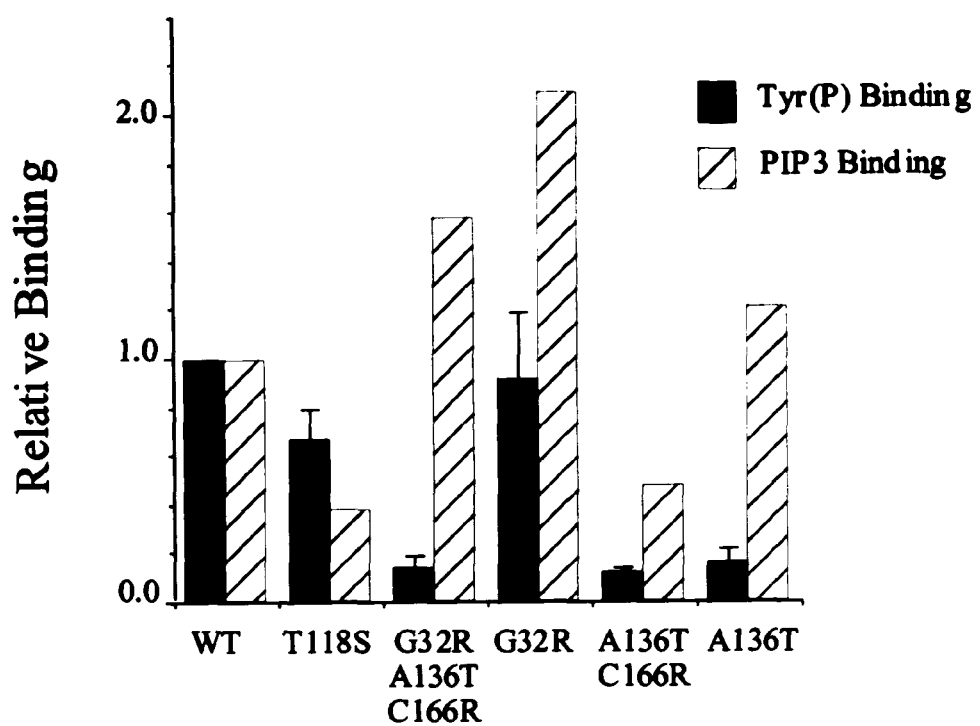
FIG. 12 is a bar graph showing phosphotyrosine versus phospholipid binding by wild type versus mutant PTB domains.

Bacterially expressed ShcC GST-PTB was tested in in vitro binding assays for binding phospholipids as previously described for SH2 domains (41). Briefly, a 200 mM mixture of crude brain phosphoinositides (Sigma) was incubated with purified PI3K in the presence of 15 mM Hepes, pH 7.0, 200 mM [$^{32}$P]ATP (1.1 mCi/mmol) and 5 mM MgCl$_2$ for 30 min at room temperature. The reaction was stopped with the addition of 10 mM EDTA and the lipids were extracted with chloroform:methanol:HCl and dried (42). The dried lipids were then resuspended in 10 mM Hepes, pH 7.0, 1 mM EDTA, sonicated then added to 20 µg of either GST or GST-PTB fusion proteins immobilized on glutathione-agarose beads (Sigma). The beads were incubated for 1 hr at room temperature then washed twice with 1 ml 30 mM Hepes, pH 7.0, 100 mM NaCl, 1 mM EDTA (HNE). Associated lipids were removed by extraction with chloroform: methanol: HCl (1:1:0.1) and resolved on thin layer chromatography using 1-propanol:2 M acetic acid (65:35 vol/vol). Radioactivity was then quantitated on a phosphorimager. The results shown in FIG. 12 represent relative amounts of PIP3 binding by wild type versus mutant PTB domains. The wild type PTB domain specifically bound PIP3. Using mutants of the ShcC PTB domain which have been characterized for their ability to bind phosphotyrosine, phosphotyrosine binding appeared to be separated from phospholipid binding. The A136T mutation greatly reduced binding to tyrosine phosphorylated proteins (as measured by binding to the activated EGFR, 47) without impairing binding to PIP3. Although less striking, the T118S mutation reduced PIP3 binding more than pTyr binding. These results suggest the existence of separate binding sites for phosphotyrosine and phospholipid. It was previously shown that the SH2 domain of PI3K also interacts with phospholipids suggesting a regulatory mechanism for PI3K activity (41). A similar mechanism can be envisioned for PTB binding to phosphoproteins. The binding to the activated EGFR as shown in FIG. 12 represents the average of three independent experiments with the standard errors marked by bars.

Figure 13:
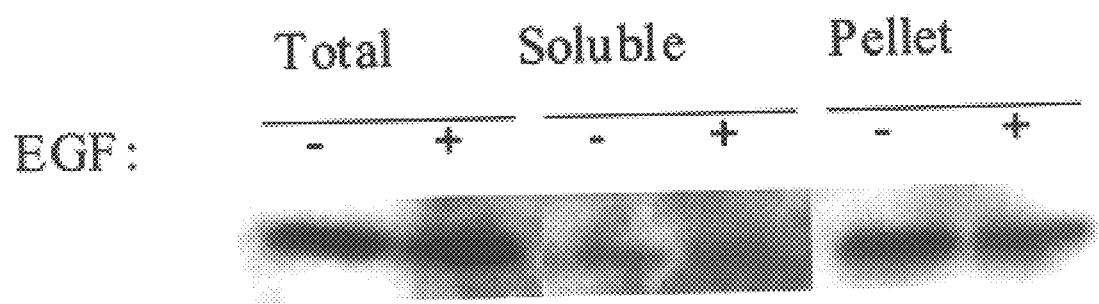
FIG. 13 are immunoblots showing membrane localization of the ShcC PTB domain.

III. HA-tagged PTB Domain of ShcC Fractionates With the Membrane Component of Cells The ability of the PTB domain to bind phosphotyrosine and phospholipid, suggested that PTB domains may direct proteins to the membrane component of cells. To test this hypothesis, the subcellular location of the isolated PTB domain was examained. The ShcC PTB domain was expressed in EGFR-transformed NIH/3T3 cells and the resulting cells were expanded, stimulated with or without EGF (100 ng/ml) for 5 min and then lysed. The insoluble debris was pelleted and the remaining sample fractionated into soluble and membrane fractions as previously described (38). After normalization for proteins content, equivalent amounts (eight micrograms) were separated on SDS-PAGE, transferred to Immobilon-P filters then Western blotted with an HA-specific monoclonal antibody. As shown in FIG. 13 the HA-PTB domain fractionated with the membrane component of cells suggesting that the PTB domain can direct membrane localization. Interestingly, treatment with EGF did not seem to affect the subcellular localization suggesting that the PTB is constitutively at the membrane. Since Shc proteins are normally cytosolic in unstimulated cells (31), this result suggests that expression of the isolated PTB domain unmasks a latent activity of the PTB domain which is normally blocked in the context of the full length protein.

Figure 14:
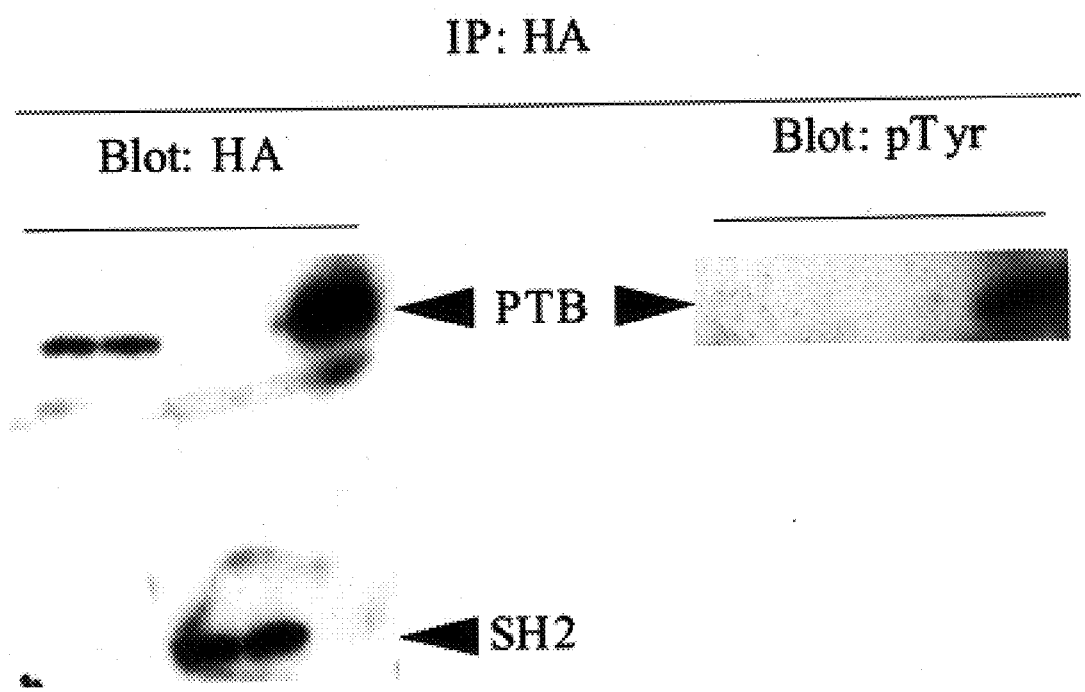
FIG. 14 are immunoblots showing that EGF treatment of PTB expressing cells resulted in a shift in the mobility of the ShcC PTB domain.
Figure 15:
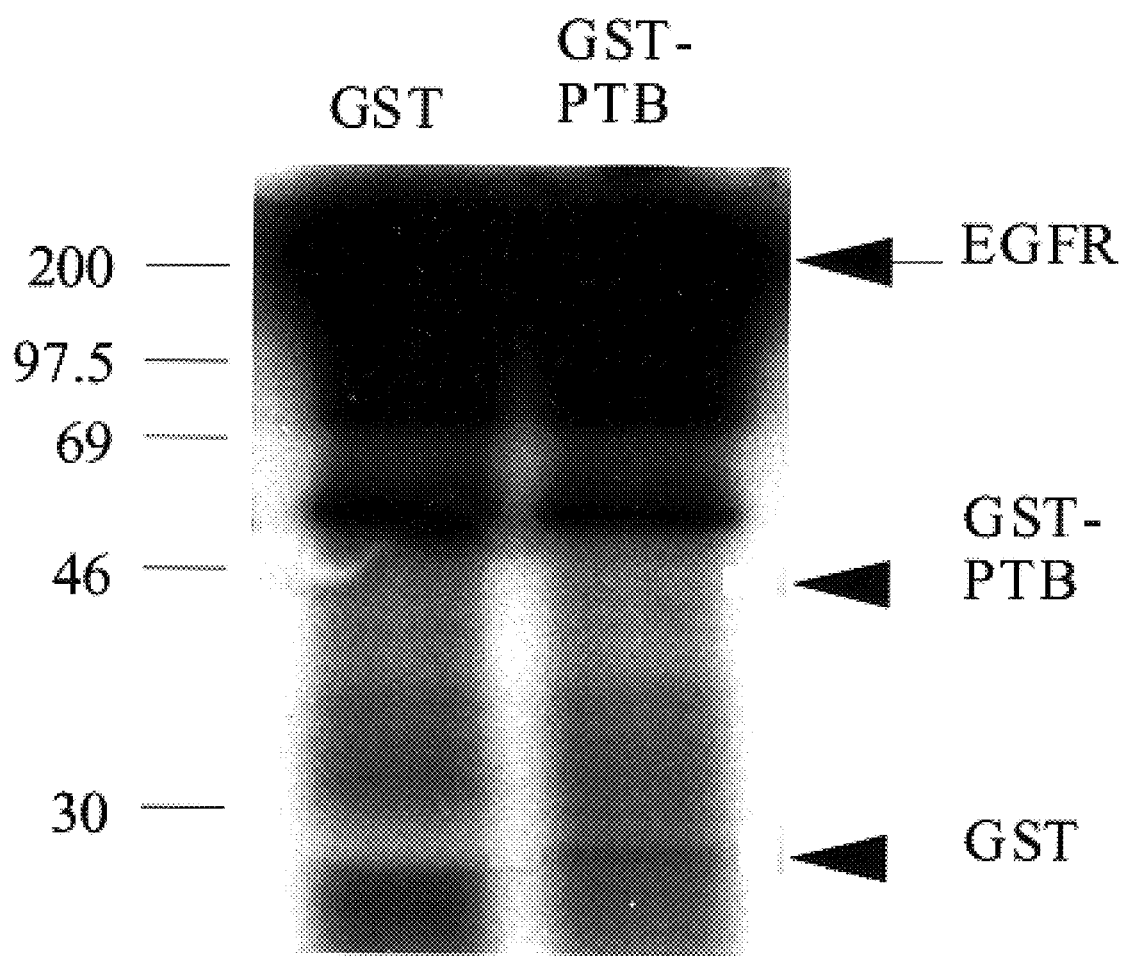
FIG. 15 is an immunoblot showing that immunoprecipitated EGFR does not phosphorylate the ShcC PTB domain in an in vitro kinase reaction.

IV. Heterologously Expressed ShcC PTB Domain Is Tyrosine Phosphorylated In Response to EGF and Constitutively Activated SrcY527F In the process of examining lysates of cells expressing either the PTB or SH2 domain of ShcC, EGF treatment of PTB expressing cells was found to result in a shift in the mobility of the PTB domain. A similar shift was detected in 293T cells transiently cotransfected with the PTB expression construct and a SrcY527F expression construct (FIG. 14). Western blot analysis with antiphosphotyrosine antibodies indicated that the slower migrating form of the PTB domain was tyrosine phosphorylated. These results are intriguing since phosphorylation of the PTB domain has not been previously described. To determine whether this phosphorylation was a direct effect of the EGFR, the ability of immunopurified EGFR to phosphorylate purified GST-PTB domain was tested. The EGFR receptor was immunoprecipitated from lysates of A431 cells stimulated with EGF for 2 min. at room temperature. A431 cells highly overexpress the endogenous EGFR and are therefore a good source of the receptor (37, 44). In vitro kinase assays were performed as previously described (34). Briefly, EGFR immunoprecipitates were washed extensively in 50 mM HEPES, pH 7.5/150 mM NaCl/10% glycerol/1% Triton X-100/1 mM EGTA/1.5 mM $MgCl_2$/100 mM sodium fluoride/10 mM sodium pyrophosphate/1 mM sodium vanadate/10 µg/ml aprotinin/10 µg/ml leupeptin and then in 20 HEPES, pH 7.5/150 mM NaCl/0.1 % Triton X-100/10% glycerol/1 mM sodium vanadate. The immunoprecipitate was split into two equivalent fractions and to one fraction was added purified GST-PTB and to the other purified GST as a negative control. The washed samples were incubated in kinase buffer (20 mM HEPES, pH 7.5/25 mM $MgCl_2$/4 mM $MnCl_2$/0.1 mM vanadate) in the presence of $\gamma[^{32}P]$-ATP for 30 min. at room temperature then fractionated on a 12% SDS-PAGE. The gel was fixed, dried and exposed to X-Ray film to visualize bands. As shown in FIG. 15, the EGFR was phosphorylated quite well; however, there was no detectable phosphorylation of the GST-PTB protein (position is marked with an arrow) suggesting that the EGFR does not directly phosphorylate the PTB domain.

In summary, the ShcC PTB domain was found to bind phospholipids in addition to tyrosine phosphorylated proteins. These two activities may involve separate regions of the PTB domain. In addition, the phosphorylation and membrane localization of the ShcC PTB domain was described.

EXAMPLE 4

Figure 16A:
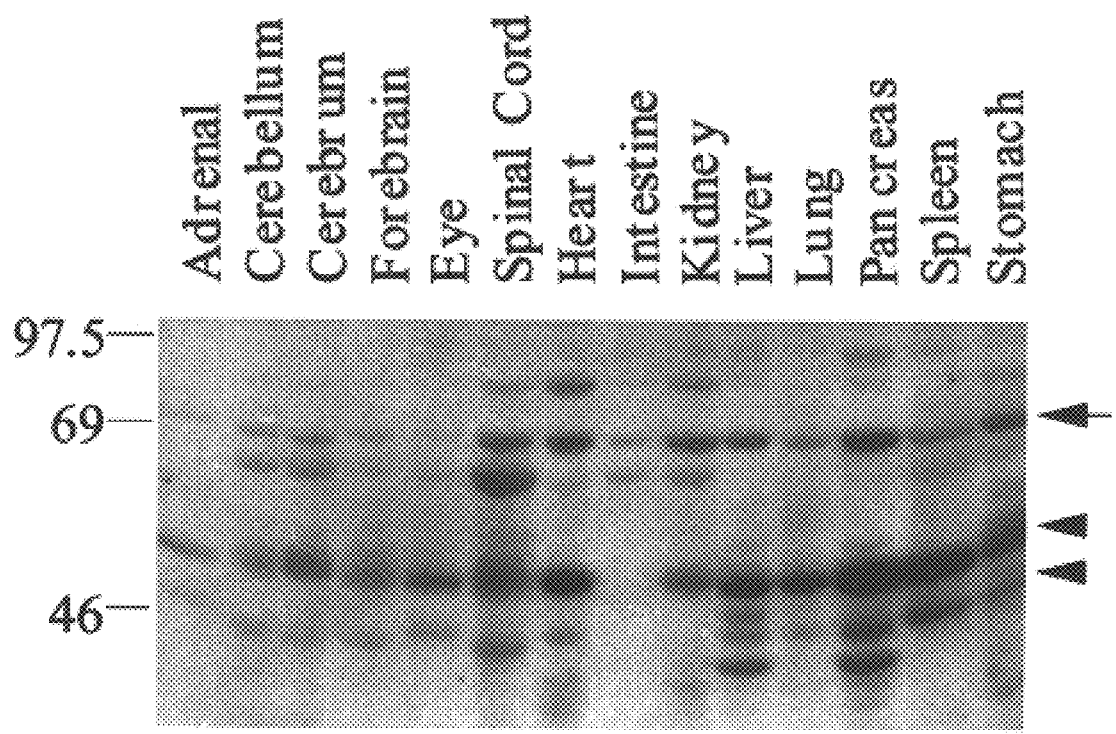
FIG. 16A is a Western blot of mouse tissues using a ShcA antibody.
Figure 16B:
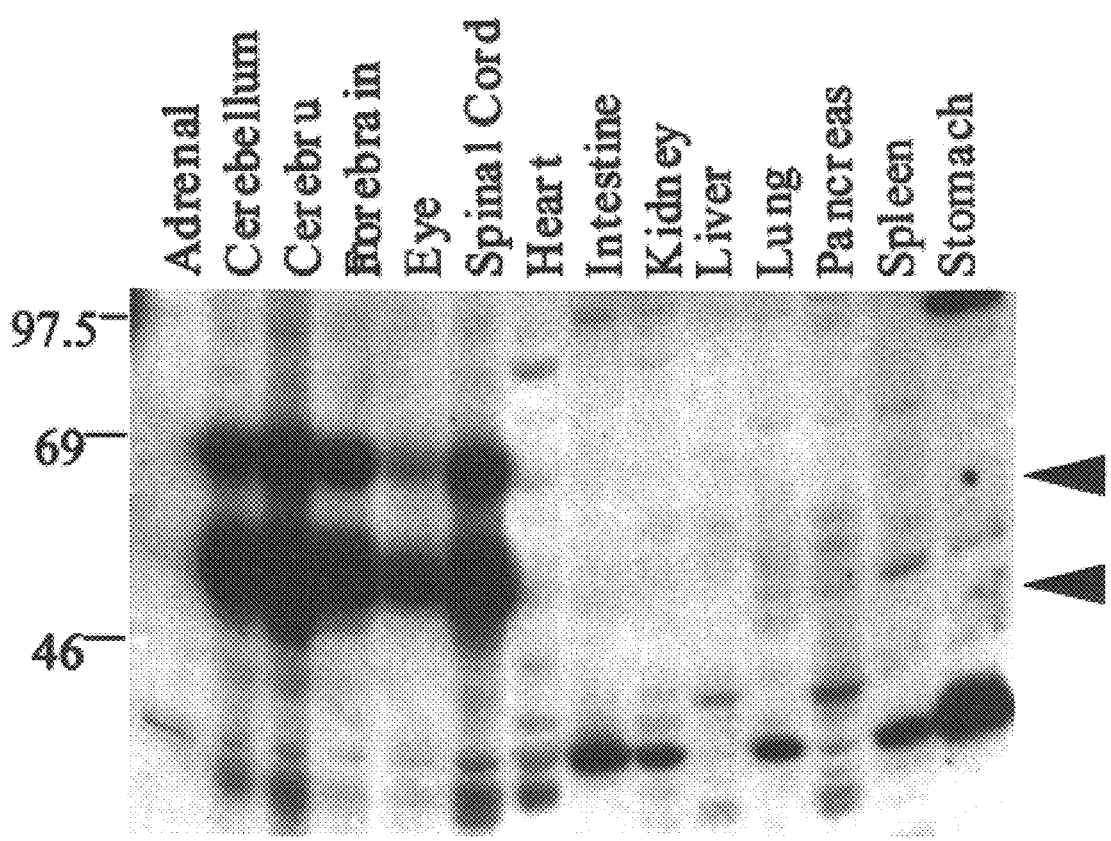
FIG. 16B is a Western blot of mouse tissues using a ShcC antibody.
Figure 16C:
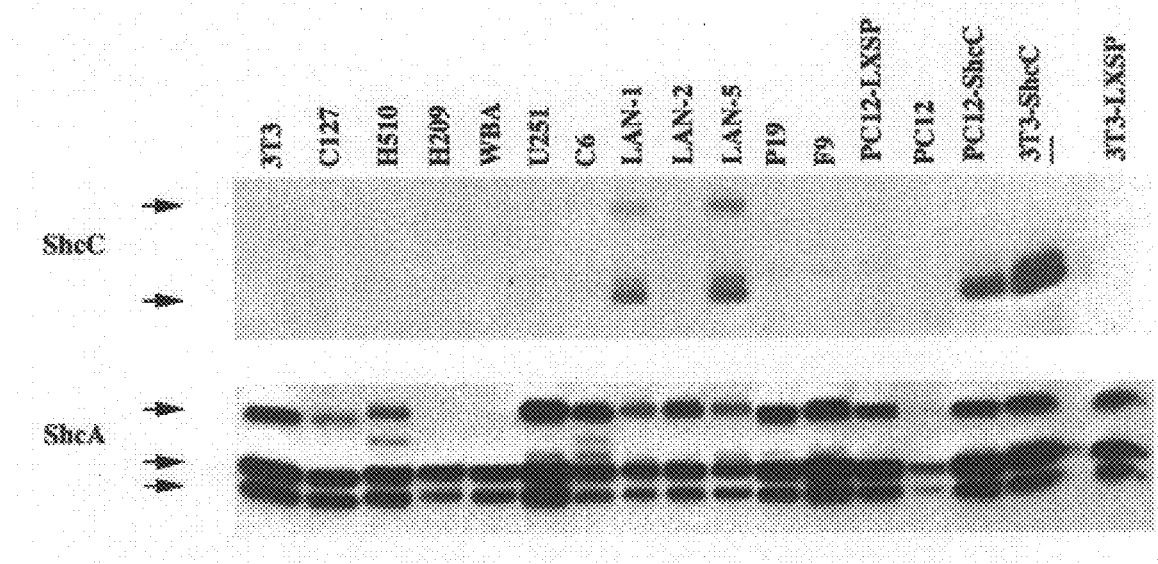
FIG. 16C is a Western blot of ShcC (top panel) and ShcA (bottom panel) protein expression in cell lines of various in cells.

ShcC Is Expressed In NB Cell Lines, the Embryonic and Adult Brain As Well As Other Embryonic Tissues ShcC is expressed only in tissues derived from the adult brain, whereas ShcA is more widely expressed (FIGS. 16A and 16B). Furthermore, Western blot analysis of lysates from cell lines of various origins indicates that endogenous ShcC expression is only detected in NB cell lines (FIG. 16C). Although full length ShcA has been reported to differentiate PC12 cells in the absence of added NGF, ShcC overexpression was not found to affect the morphology of PC12 cells. Since ShcA and ShcC have not been compared side by side, it is possible that the apparent difference in biologic activity may be due to levels of expression of the transfected gene.

Figure 17A:
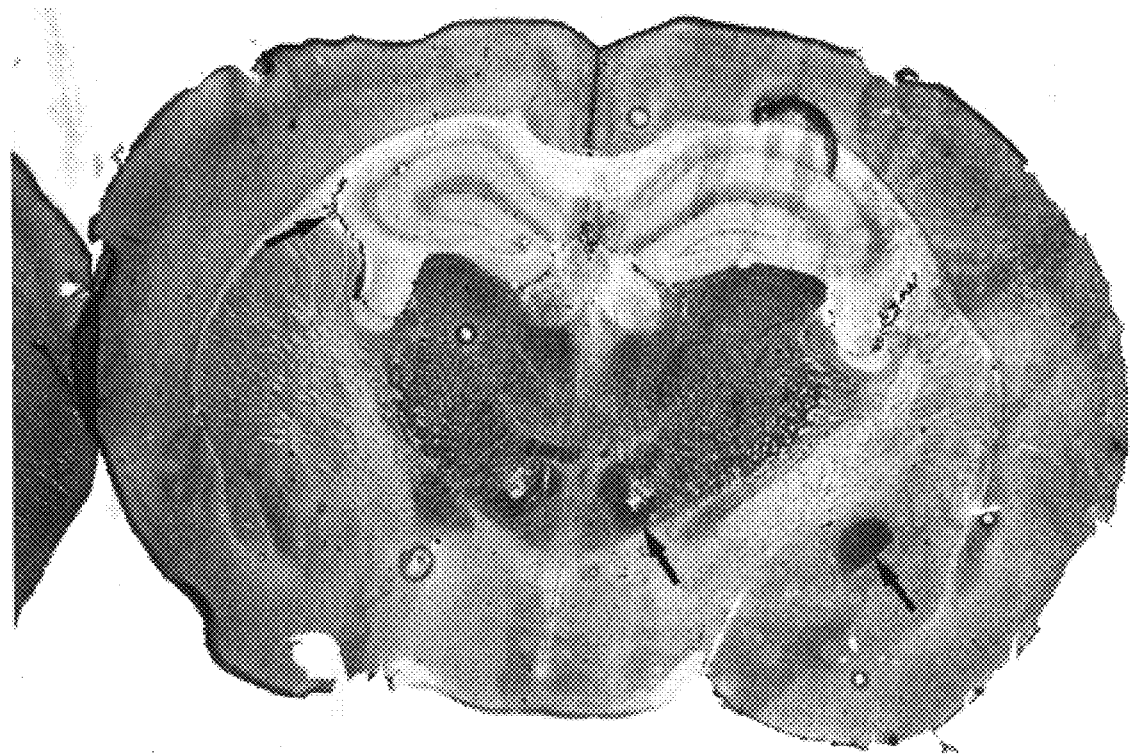
FIG. 17A shows ShcC expression in adult mouse tissues.
Figure 17B:
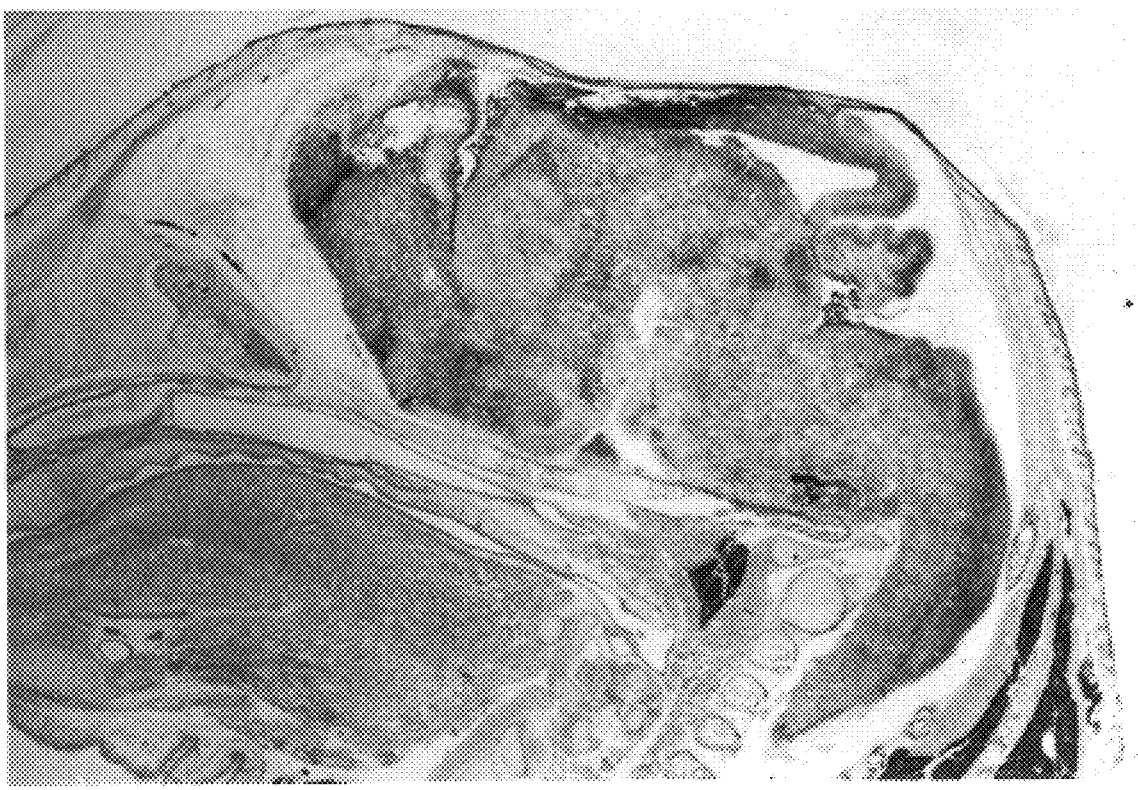
FIG. 17B shows ShcC expression in embryonic E18 CD1 mouse tissues.
Figure 18A:
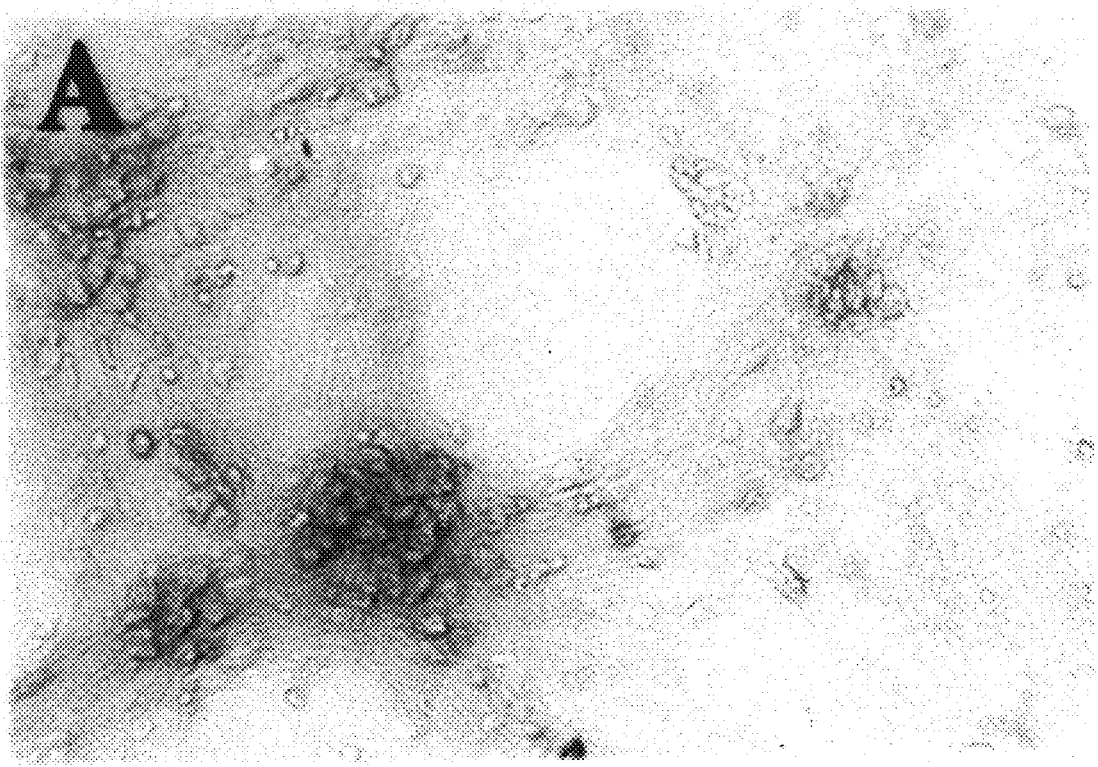
FIG. 18A shows ShcC immunostaining after 6 days in vitro.
Figure 18B:
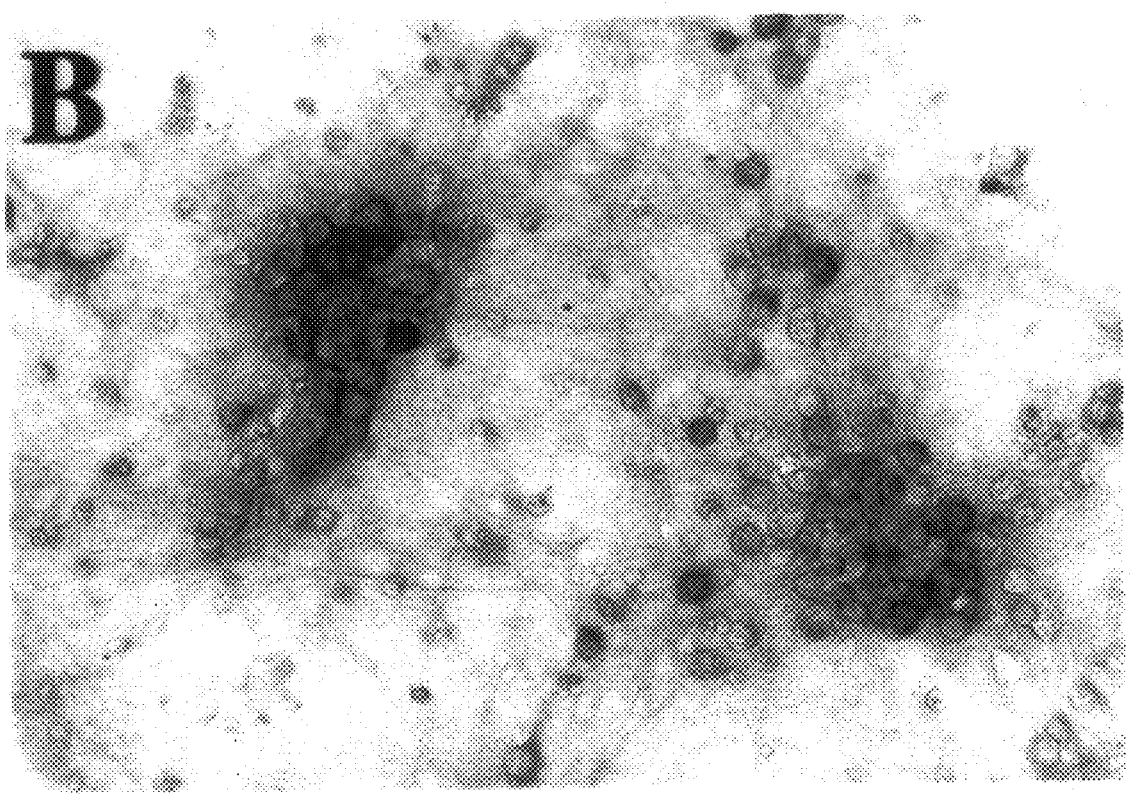
FIG. 18B shows ShcC immunostaining by 9 days in vitro.
Figure 18C:
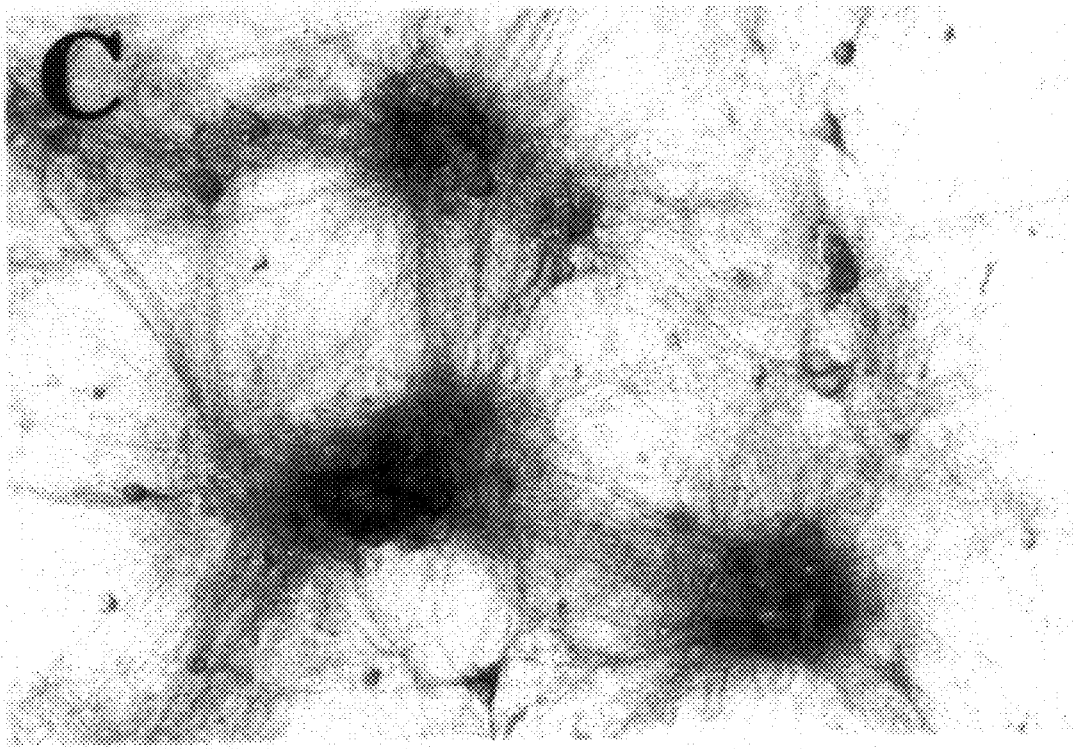
FIG. 18C shows ShcC immunostaining by 12 days in vitro.
Figure 18D:
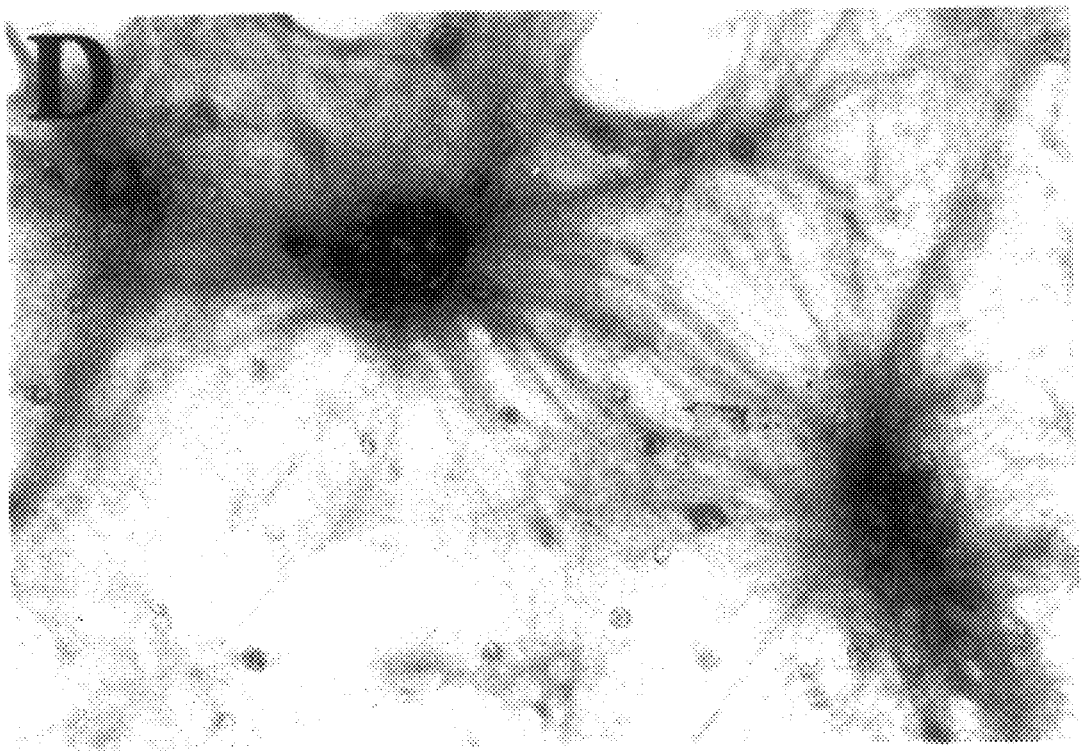
FIG. 18D shows ShcC immunostaining by 15 days in vitro.

Using tissue from frozen sections of day 18 embryonic mice as well as adult mice, the temporal and spatial patterns of ShcC expression was examined. Affinity purified antibodies to ShcC are specific to ShcC and do not cross react with ShcA on Western blot analyses (FIG. 16). Using these antibodies in immunohistochemical staining, specific expression of ShcC was detected in both the adult and embryonic (E18) brain (FIG. 17). Immunoreactivity was competed away by the inclusion of soluble antigen (GST-SH2 protein). ShcC expression was also detected in a number of additional embryonic tissues including a subset of muscles in the neck, the fetal liver and the muscles surrounding the intestines. Since ShcC expression was not detected in the adult counterparts of these tissues, these results suggest that ShcC may have a specific function in tissues other than the brain but at very restricted points during development. Abundant ShcC expression in the cerebellum and spinal cord was observed (FIG. 17).

II. ShcC Is Expressed In Primary Mouse Neuronal Cultures After Differentiation For 10 Days To determine which cells in the brain express ShcC, ShcC expression in in vitro cultures of primary neurons has been examined. An advantage of this approach is that highly enriched cultures of neurons can be isolated and used to define the cell-type expression of ShcC. However, since other cell types are also present in these cultures, the exact types of cells expressing ShcC can be determined through imunohistochemical staining of the cultures. Preliminary results indicated that ShcC expression was specifically induced in neuron-like cells after 9 days in culture on a rat astrocyte feeder layer suggesting that ShcC expression is important in the in vitro differentiation of neurons (FIG. 18). The staining was specific to the neuron-like cells as the astrocyte feeder layer was negative for ShcC staining (FIG. 18A) as were microglial cultures (data not shown).

The primary cultures were isolated by the following protocol. Briefly, Swiss Webster mouse embryos (day 16 of gestation) or Sprague-Dawley rat embryos (day 18 of gestation) were used to generate cortical and hippocampal neuronal cultures as previously described (29). Mouse/rat embryos were cooled in sterile $Ca^{2+}/Mg^{2+}$-free (CMF)

Hanks' balanced salt solution supplemented with 20 mM HEPES, 4.2 mM sodium bicarbonate, 1 mM pyruvate at pH 7.25, and 3 mg/ml bovine serum albumin (28). The dissected cortical tissue was rinsed with CMF and resuspended in 5.0 ml of 0.125% trypsin (Sigma, St. Louis, Mo.) and 0.5 mM EDTA in CMF at 37° C. The suspension was mixed by gentle pipeting and incubated in a shaking water bath for 10 min at 37° C. The trypsin was quenched with 8.0 ml of 10% fetal bovine serum in DMEM, followed by a repeat of the pipeting step. The suspension was then centrifuged at 270×g for 5.0 min, the supernatant aspirated off, and the tissue resuspended in 4.0 ml of DMEM supplemented with N2 (27). The cortical tissue was then mechanically dissociated as previously described (28) and filtered through a 40 $\mu$m sterile Falcon Cell Strainer (Becton Dickinson, Franklin Lakes, N.J.). Neurons were plated on polylysine for short-term cultures (0–7 dayes) or on confluent layers of purified rat astrocytes (40) for long-term cultures (7–30 days). The cultures were maintained at 37° C. with 5% $CO_2$ and half of the media was replaced every 3 days with fresh DMEM-N2. The ShcC immunostaining was performed, with minor modifications, as previously described (29). The cultures were fixed with fresh 4% paraformaldehyde in PBS (pH 7.2) for 20 mm, rinsed twice for 5 min with PBS, and then permeabilized with 0.2% Triton X-100 in 0.1 M Tris and 0.85% NaCl, pH 7.5 (Tris-A) for 20 min, followed by two additional washes with 0.1 M Tris, and 0.85% NaCl, pH 7.5 (Tris-buffer). The fixed cells were then incubated with 0.1 M Tris, 0.85% NaCl, and 2% BSA (Sigma, St. Louis, Mo.), pH 7.5, (Tris-B) to reduce non-specific binding in subsequent steps of the immunostaining protocol. The anti-ShcC primary antibody (0.14 $\mu$g/ml) diluted 1:100 with Tris-B, was added to the wells and incubated for one hr at 37° C. with gentle agitation. The primary antibody was aspirated off and the wells rinsed three times with Tris-buffer. The secondary antibody, biotinylated anti-rabbit IgG (ABC Elite immunoperoxidase kit, Vector Labs, Burlingame, Calif.) in Tris-B, was added and incubated for one hr at 37° C. with gentle agitation, followed by three rinses with Tris-buffer. The avidin-biotin-peroxidase complex (ABC Elite immunoperoxidase kit, Vector Labs, Burlingame, Calif.) in Tris-B was added to the wells and incubated for one hr at 37° C., followed by three rinses with Tris-buffer. The ShcC immunostaining was detected with a Vector SG peroxidase substrate kit (SG kit, Vector Labs, Burlingame, Calif.). Immunocytochemical controls without primary antibody or with control rabbit IgG were uniformly negative. The mouse/rat astrocyte and microglia cultures failed to produce any detectable immunostaining even at twice the concentration of anti-ShcC antibody used for immunostaining of the neuronal cultures.

The restricted expression of ShcC in tissues of the brain indicates a role for ShcC in neural specific signaling and development. This is also supported by results from immunohistochemical staining of embryonic mouse brains; the finding that ShcC is expressed in NB cell lines but not other brain derived tumor lines; and the observation that ShcC expression is induced in in vitro neuron cultures during neuronal differentiation.

Having illustrated and described the principles of the invention in a preferred embodiment, it should be appreciated to those skilled in the art that the invention can be modified in arrangement and detail without departure from such principles. In particular, it will be appreciated that the description above relating to embodiments of the invention for ShcC proteins and nucleic acids encoding same are applicable to and can be carried out with the Shc B protein of the invention, and nucleic acids encoding same. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

Below full citations are set out for the references referred to in the specification and detailed legends for the figures are provided.

The application contains sequence listings which form part of the application.

TABLE 1

Summary of mutations in the ShcC PTB domain

| Mutation | Location of Mutation[1] | Relative Binding |
|---|---|---|
| Wild Type | — | 1.0 |
| T118S | Loop 5 ($\beta2'$-$\beta3$) | 0.81 ± 0.13 |
| E63G | $\alpha2$ | 0.087 ± 0.037 |
| M130I | Loop 7 ($\beta4$-$\beta5$) | 1.0 ± 0.31 |
| S132V | Loop 7 ($\beta4$-$\beta5$) | |
| G32R | Loop 1 ($\alpha1$-$\beta1$) | 0.14 ± 0.044 |
| A136T | $\beta5$ | |
| C166R | Loop 10 ($\beta7$-$\alpha3$) | |
| G32R | Loop 1 ($\alpha1$-$\beta1$) | 0.93 ± .28 |
| A136T | $\beta5$ | 0.12 ± 0.021 |
| C166R | Loop 10 ($\beta7$-$\alpha3$) | |
| A136T | $\beta5$ | 0.16 ± 0.061 |
| T58A | $\alpha2$ | 1.2 ± 0.20 |
| G30R | $\alpha1$ | 1.0 ± 0.12 |
| H128Q | Loop 7 ($\beta4$-$\beta5$) | |
| G139E | Loop 8 ($\beta5$-$\beta6$) | 0.073 ± 0.0067 |
| D140N | Loop 8 ($\beta5$-$\beta6$) | |
| T111I | $\beta3$ | 1.2 ± 0.35 |
| S86C | Loop 3 ($\alpha2$-$\beta2$) | 1.2 ± 0.10 |
| V36M | $\beta1$ | 1.0 ± 0.23 |

[1]The nomenclature used corresponds to that used in Zhou, et. al. (1995) Nature 378, 584.
[2]The relative binding affinities for these mutants were determined in independent binding experiments with the wild-type, G32R, A136T, A136T/C166R and G32R/A136T/C166R mutant PTB domains only.

Full Citations for References Referred to in the Specification

1. Pelicci, G., Lanfrancone, L., Grignani, F., McGlade, J., Cavallo, F., Forni, G., Nicoletti, I., Grignani, F., Pawson, T. & Pelicci, à. G. (1992) Cell 70, 93–104.
2. Blaikie, P., Immanuel, D., Wu, J., Li, N., Yajnik, V. & Margolis, B. (1994) J Biol Chem 269,32031–4.
3. Kavanaugh, W. M. & Williams, L. T. (1994) Science 266, 1862–5.
4. Songyang, Z., Shoelson, S. E., McGlade, J., Olivier, J. P., Pawson, T., Bustelo, X. R., Barbacid, M., Sabe, H., Hanafusa, H., Yi, T., Ren, R., Baltimore, D., Ratnofsky, S., R. A., F. & Cantley, L. C. (1994) Mol. Cell. Biol. 14, 2777–2785.
5. Batzer, A. G., Rotin, D., Urena, J. M., Skolnick, E. Y. & Schlessinger, J. (1994) Mol. Cell. Biol. 14, 5192–5201.
6. Yokote, K., Mori, S., Hansen, K., McGlade, J., Pawson, T., Heldin, C. H. & Claesson, W. L. (1994) J Biol Chem 269, 15337–43.
7. Kavanaugh, W. M., Turck, C. W. & Williams, L. T. (1995) Science 268,1177–1179.
8. van der Geer, P., Wiley, S., Lai, V. K.-M., Olivier, J. P., Gish, G. D., Stephens, T., Kaplan, D., Shoelson, S. & Pawson, T. (1995) Curr Biol 5, 404–412.
9. Pawson, T. (1995) Nature 373, 573–579.

10. Burns, L. A., Karnitz, L. M., Sutor, S. L. & Abraham, R. T. (1993) J Biol Chem 268, 17659–61.
11. Cutler, R. L., Liu, L., Damen, J. E. & Krystal, G. (1993) J Biol Chem 268,21463–5.
12. Damen, J. E., Liu, L., Cutler, R. L. & Krystal, G. (1993) Blood 82, 2296–303.
13. Lanfrancone, L., Pelicci, G., Brizzi, M. F., Arouica, M. G., Casciari, C., Giuli, S., Pegoraro, L., Pawson, T. & Pelicci, P. G. (1995) Oncogene 10, 907–17.
14. Ravichandran, K. S., Lee, K. K., Songyang, Z., Cantley, L., Burn, P. & Burakoff, S. J. (1993) Science 262, 902–905.
15. Crowe, A. J., McGlade, J., Pawson, T. & Hayman, M. J. (1994) Oncogene 9, 537–44.
16. McGlade, J., Cheng, A., Pelicci, G., Pelicci, P. G. & Pawson, T. (1992) Proc. Natl. Acad. Sci. USA 89, 8869–8873.
17. Salcini, A. E., McGlade, J., Pelicci, G., Nicoletti, I., Pawson, T. & Pelicci, P. G. (1994) Oncogene 9, 2827–36.
18. Rozakis, A. M., McGlade, J., Mbamalu, G., Pelicci, G., Daly, R., Li, W., Batzer, A., Thomas, S., Brugge, J., Pelicci, P. G. & et, al. (1992) Nature 360, 689–92.
19. Obermeier, A., Lammers, R., Wiesmuller, K. H., Jung, G., Schlessinger, J. & Ullrich, A. (1993) J. Biol. Chem. 268, 22963–22966.
20. Stephens, R. M., Loeb, D. M., Copeland, T. D., Pawson, T., Greene, L. A. & Kaplan, D. R. (1994) Neuron 12, 691–705.
21. Lai, K.-M. V., Olivier, J. P., Gish, G., Henkemeyer, M., McGlade, J. & Pawson, T. (1995) Mol Cell Biol in press,
22. O'Bryan, J. P., Frye, R. A., Cogswell, P. C., Neubauer, A., Kitch, B., Prokop, C., R. Espinosa, I., Beau, M. M. L., Earp, H. S. & Liu, E. T. (1991) Mol. Cell. Biol. 11, 5016–5031.
23. Songyang, Z., Shoelson, S. E., Chaudhuri, M., Gish, G., Pawson, T., Haser, W., King, F., Roberts, T., Ratnofsky, S., Lechleider, R. J., Neel, B. G., Birge, R. B., Fajardo, J. E., Chou, M. M., Hanafusa, H., Schaffhausen, B. & Cantley, L. C. (1993) Cell 72, 767–778.
24. Marengere, L. E. & Pawson, T. (1992) J Biol Chem 267, 22779–86.
25. Waksman, G., Shoelson, S. E., Pant, N., Cowburn, D. & Kuriyan, J. (1993) Cell 72, 779–790.
26. Biscardi, J. S., F. Denhey, G. F. Buehler, D. A. Chesnutt, S. C. Baragona, J. P. O'Bryan, C. J. Der, D. W. Fults, and P. F. Maness. 1996. Rek, a gene expressed in retina and brain, encodes a novel receptor tyrosine kinase of the Axl/Tyro3 family. J Biol Chem 271:29049–59.
27. Bottenstein, J. E., and G. H. Sato. 1979. Growth of a rat neuroblastoma cell line in serum-free supplemented medium. Proc Natl Acad Sci USA 76:514–7.
28. Brewer, G., and C. W. Cotman. 1989. Survival and growth of hippocampal neurons in defined medium at low density: advantages of a sandwich culture technique or low oxygen. Brain Res 494:65–74.
29 Cribbs, D. H., V. M. Kreng, A. J. Anderson, and C. W. Cotman. 1996. Crosslinking of membrane glycoproteins by Concanavalin A induces apoptosis in cortical neurons. Neuroscience 75:173–85.
30. Di Fiore, P. P., J. H. Pierce, T. P. Fleming, R. Hazan, A. Ullrich, C. R. King, J. Schlessinger, S. A. Aaronson, and H. N. Antoniades. 1987. Overexpression of the human EGF receptor confers and EGF-dependent transformed phenotype to NIH/3T3 cells. Cell 51:1063–1070.
31. Di Guglielmo, G. M., P. C. Baass, W. J. Ou, B. I. Posner, and J. J. Bergeron. 1994. Compartmentalization of SHC, GRB2 and mSOS, and hyperphosphorylation of Raf-1 by EGF but not insulin in liver parenchyma. Embo J 13:4269–77.
32. Giorgetti, S., P. G. Pelicci, G. Pelicci, and O. E. Van. 1994. Involvement of Src-homology/collagen (SHC) proteins in signaling through the insulin receptor and the insulin-like-growth-factor-I-receptor. Eur J Biochem 223:195–202.
33. Hauser, C. A., J. K. Westwick, and L. A. Quilliam. 1995. Ras-mediated transcription activation: analysis by transient cotransfection assays. Meth Enzymol 255:412–26.
34. Henkemeyer, M., L. E. M. Marengere, J. McGlade, J. P. Olivier, R. A. Conlon, D. P. Holmyard, K. Letwin, and T. Pawson. 1994. Immunolocalization of the Nuk receptor tyrosine kinase suggests roles in segmental patterning of the brain and axonogenesis. Oncogene 9:1001–14.
35. Marais, R., J. Wynne, and R. Treisman. 1993. The SRF accessory proteins Elk-1 contains a growth factor-regulated transcriptional activation domain. Cell 73:381–93.
36. Maru, Y., H. Hirai, and F. Takaku. 1990. Overexpression confers an oncogenic potential upon the eph gene. Oncogene 5:445–447.
37. Merlino, G. T., S. Ishii, J. Whang-Peng, T. Knutsen, Y.-H. Xu, A. J. L. Clark, R. H. Stratton, R. K. Wilson, D. P. Ma, B. A. Roe, J. H. Hunts, N. Shimizu, and I. Pastan. 1985. Structure and localization of genes encoding aberrant and normal epidermal growth factor receptor RNAs from A431 human carcinoma cells. Mol. Cell. Biol. 5:1722–1734.
38. O'Bryan, J. P., Y.-W. Fridell, R. Koski, B. Varnum, and E. T. Liu. 1995. The transforming receptor tyrosine kinase, Axl, is post-translationally regulated by proteolytic cleavage. J Biol Chem 270:551–7.
39. O'Bryan, J. P., R. A. Frye, P. C. Cogswell, A. Neubauer, B. Kitch, C. Prokop, I. R. Espinosa, M. M. L. Beau, H. S. Earp, and E. T. Liu. 1991. axl, a transforming gene isolated from primary human myeloid cells, encodes a novel receptor tyrosine kinase. Mol. Cell. Biol. 11:5016–5031.
40. Pike, C. J., C. B. J., R. Monzavi, and C. W. Cotman. 1994. Beta-amyloid-induced changes in cultured astrocytes parallel reactive astrocytosis associated with senile plaques in Alzheimer's disease. Neuroscience 63:517–31.
41. Rameh, L. E., C.-S. Chen, and L. C. Cantley. 1995. Phosphatidylinositol (3, 4, 5)P3 interacts with SH2 domains and modulates PI 3-kinase associaton with tyrosine-phosphorylated proteins. Cell 83:821–830.
42. Serunian, L. A., K. R. Auger, and L. C. Cantley. 1991. Identification and quantification of novel polyphosphoinositides produced in response to platelet-derived growth factor stimulation. Meth Enzymol 198:78–87.
43. Tanaka, M., and W. Herr. 1990. Differential transcriptional activation by Oct-1 and Oct-2: independent activation domains induce Oct-2 phosphorylation. Cell 60:375–86.
44. Ullrich, A., L. Coussens, J. S. Hayflick, T. J. Dull, A. Gray, A. W. Tam, J. Lee, Y. Tarden, T. A. Liberman, J. Schlessinger, J. Downward, E. L. V. Mayes, N. Whittle, M. D. Waterfield, and P. E. Seeberg. 1984. Human epidermal growth factor receptor cDNA sequence and aberrant expression of the amplified gene in A431 epidermoid carcinoma cells. Nature 309:418–425.
45. van der Geer, P., S. Wiley, G. Gish, V. K.-M. Lai, R. Stephens, M. White, D. Kaplan, and T. Pawson. 1996. Identification of residues that control specific binding of the Shc phosphotyrosine binding domain to phosphotyrosine sites. Proc. Natl. Acad. Sci. USA 93:963–968.
46. Velu, T. J., L. Beguinot, W. C. Vass, M. C. Willingham, G. T. Merlino, I. Pastan, and D. R. Lowy. 1987. Epidermal growth factor-dependent transformation by a human EGF receptor proto-oncogene. Science 238:1408–1410.

47. Yajnik, V., P. Blaikie, P. Bork, and B. Margolis. 1996. Identification of residues within the SHC phosphotyrosine binding/phosphotyrosine interaction domain crucial for phosphopeptide interaction. J. Biol. Chem. 271:1813–1816.

48. Zhou, M.-M., K. Ravichandran, E. T. Olejniczak., A. M. Petros., R. P. Meadows, J. E. Harlan, W. S. Wade, S. J. Burakoff, and S. W. Fesik. 1995. Structure and ligand recognition of the phosphotyrosine binding domain of Shc. Nature 378:584–592.

DETAILED FIGURE LEGENDS FOR FIGS. 1 TO 5, 8 TO 18

FIG. 1

Alignment of the Shc family of proteins. ShcA [SEQ ID NO:7] and ShcC [SEQ ID NO:2] represent the predicted peptide sequences of the respective mouse genes. dShc represents the predicted sequence of the Drosophila Shc gene. [SEQ ID NO:9] (21). The predicted peptide sequence [SEQ ID NO:6] of the partial human sck cDNA is shown (3). hShcA [SEQ ID NO:8] represents the predicted peptide sequence of the humanshcA gene (pelicci). Sequences were aligned using the Pileup program of GCG software analysis package. The results of this comparison were imported into the Maligned multiple sequence alignment program. Amino acids which are identical in at least 4 of 5 sequences are shown in reverse type. Boundaries of the SH2 and PTB domains are marked with arrows.

FIG. 2A

ShcC RNA is specifically expressed in brain tissues. Northern analysis. Filters were hybridized, washed under stringent conditions then exposed at −70° C. with an intensifying screen for 48 hrs for shcB or overnight for ShcC. Arrow mark the position of the two ShcC transcripts. Lanes are as follows: 1. Heart; 2. Brain; 3. Spleen; 4. Lung; 5. Liver; 6. Skeletal muscle; 7. Kidney; and, 8. Testis.

FIG. 2B

ShcC RNA is specifically expressed in brain tissues. RT-PCR analysis. PCR products were fractionated on an agarose gel and stained with ethidium bromide to visualize bands. Molecular weight markers (in base pairs) are shown to the left.

FIG. 3A

ShcC proteins are specifically expressed in brain derived tissues. Fifty micrograms of total protein from each of the indicated mouse tissues, except for adrenal and eye which only had 25 mg, was fractionated on 10% SDS-PAGE, transfered to filters and probed with affinity purified ShcC antibody (1 mg/ml in TBST/3% non-fat dry milk). Lanes are as follows: 1. adrenal; 2. cerebellum; 3. cerebrum; 4. forebrain; 5. eye; 6. spinal cord; 7. heart; 8. intestine; 9. kidney; 10. liver; 11. lung; 12. pancreas; 13. spleen and 14. stomach.

FIG. 3B

ShcC proteins are specifically expressed in brain derived tissues. Same as in FIG. 3A except Protein-A Sepharose purified anti-Shc antibody was used at 1–2 mg/ml. Lanes are as follows: 1. adrenal; 2. cerebellum; 3. cerebrum; 4. forebrain; 5. eye; 6. spinal cord; 7. heart; 8. intestine; 9. kidney; 10. liver; 11. lung; 12. pancreas; 13. spleen and 14. stomach.

FIG. 4A

SH2 domains of ShcB and ShcC bind tyrosine phosphorylated proteins. A431 cells were grown in the presence or absence of EGF (100 ng/ml) for 1 min then lysed in cold PLC-LB. Equal amounts of fusion proteins were mixed with equivalent amounts of lysate, spun down washed, fractionated on 10% SDS-PAGE then probed with the indicated antibodies. Anti-GST is shown to confirm that equal amounts of fusion proteins were used in the mixes.

FIG. 4B

Shc family members bind differentially to tyrosine phosphorylated proteins. Binding experiments were performed as in FIG. 4A except with lysates of NIH/3T3 cells transformed by the Axl tyrosine kinase receptor.

FIG. 5A

The PTB domains of ShcC and ShcA bind to activated growth factor receptors. In vitro binding experiments were performed as described for FIG. 4A. Equivalent amounts of lysate from EGF-stimulated A431 cells were incubated with 10 μg of either ShcA or ShcC GST-PTB fusion proteins. Bound proteins weree fractionated on SDS-PAGE then transferred to Immobilon which was probed with anti-phosphotyrosine antibody. No binding was seen with GST alone (data not shown).

FIG. 5B

The PTB domains of ShcC and ShcA bind to activated growth factor receptors. In vitro binding experiments were performed as in FIG. 5A using lysates from NIH/3T3 cells which overexpress TrkA (23). Lysates from cells treated with, +, or without, −, NGF (100 ng/ml) were incubated with the indicated GST-PTB fusion protein either in the presence, +, or absence, −, of competing phosphopeptide. The filter was probed with anti-phosphotyrosine antibody. Anti-TrkA antibody was also used to confirm that the tyrosine phosphorylated pp140 and pp110 proteins were the TrkA mature form and precursor (data not shown). TrkA is tyrosine phosphorylated in these cells even prior to NGF stimulation, possibly owing to the high receptor density.

FIGS. 8A and 8B

Effect of dominant negatives on Gal-Elk activation by EGF in 293T cells. 8A. The various dominant negative constructs were tested for their effect on Gal-Elk activation. 8B. To ensure that these constructs were specific, their effect on activation of Gal-Elk by activated Hras61L, which should be refractory to the effects of these protein, was tested.

FIG. 9

Effect of ShcC dominant negative proteins on the in vitro kinase activity of HA-MAPK. The counts from untransfected controls were subtracted as background.

FIG. 10

Inhibition of soft agar growth. NIH/3T3 cells transformed by overexpression of the EGFR were transfected with either vector, PTB or SH2 selected. Stable cell lines were plated in soft agar assays ($10^4$ cells per well). Quantitation of colony formation. After 34 weeks the colonies were stained with MTT (thiazol blue) and counted.

FIG. 11

ShcC activation of MAPK. Gal-Elk activation by EGF was measured as described in Example 2. Cells were cotransfected with the reporter constructs along with either empty vector or the ShcC full-length cDNA. Cells were then starved and then treated with or without EGF (100 ng/ml) for 4–5 hours at 37° C. Samples were processed as described in Example 2.

FIG. 12

Mutations in the PTB domain differentially affect phosphotyrosine versus phospholipid binding. The values for binding were normalized to wild type after subtraction of background, i.e. GST.

FIG. 13

Membrane localization of the ShcC PTB domain. EGFR transformed cells expressing the ShcC PTB domain were fractionated into membrane and cytosolic fractions following growth factor stimulation. Equivalent amounts of protein were loaded in each lane. The blot was probed with a monoclonal HA antibody which recognizes the HA epitope tag on the $NH_2$-terminus of the PTB.

FIG. 14

The ShcC PTB domain is tyrosine phosphorylated in Src527F expressing 293T cells. 293T cells were transfected with either the HA epitope-tagged PTB domain (lanes 1, 2, 5) or HA epitope-tagged SH2 domain (lanes 3 & 4). The cells in lane 5 were cotransfected with activated Src527F. Samples were immunoprecipitated with HA monoclonal antibody (Babco) and then Western blotted with the indicated antibodies.

FIG. 15

Immunoprecipitated EGFR does not phosphorylate the ShcC PTB domain in an in vitro kinase reaction. The EGFR was immunopurified and then incubated with either purified GST or GST-PTB domain. The samples were then subjected to an in vitro kinase reaction and analyzed as described in Example 3. The location of the GST and GST-PTB proteins are marked with arrows to the right of the gel.

FIGS. 16A, 16B, 16C

Shc family members are differentially expressed. 16A. Western blot analysis of mouse tissues using a ShcA antibody. 16B. Same as 16A except blot was probed with ShcC antibody. 16C. Analysis of ShcC (top panel) and ShcA (bottom panel) protein expression in cell lines.

FIGS. 17A, 17B

ShcC expression in adult and embryonic mouse tissues. Frozen sections of either adult (17A) or embryonic E18 (17B) CD1 mouse tissues were stained with affinity purified ShcC antibody. As indicated by arrows in the sections, many regions of the adult and embryonic brain are positive for ShcC expression. Furthermore, additional embryonic tissues, such as the neck muscles and muscles surrounding the intestine (not shown), are also positive for ShcC expression. 17A. Transverse section of the adult brain. 17B. Sagittal section of the embryonic brain.

FIGS. 18A, 18B, 18C, 18D

Immunostaining indicates that there is an increase in the expression of ShcC as the cortical neurons differentiate in vitro. Mouse cortical neurons were cultured on a monolayer of rat astrocytes and observed at different times for the level of ShcC expression by immunocytochemistry. Even after 6 days in vitro, very little ShcC immunostaining is apparent (18A) but by 9 days prominent staining is seen in the soma (18B). At later time points, 12 days (18C) and 15 days (18D), robust staining is seen in the soma of most of the neurons in the culture. The neurites (fibrous processes) also contain significant levels of ShcC immunostaining at the later time points (18C & 18D). The mouse/rat astrocyte and microglia cultures failed to produce any detectable immunostaining even at twice the concentration of anti-ShcC antibody used for immunostaining of the neuronal cultures.

We claim:

1. An isolated nucleic acid molecule which comprises:

(i) a nucleic acid sequence encoding a protein having the amino acid sequence shown in SEQ ID NO:2 or FIG. 7;

(ii) nucleic acid sequences complementary to (i); or (iii) a nucleic acid capable of hybridizing under high stringency salt and temperature conditions to a nucleic acid of (i), wherein said high stringency salt and temperature conditions are selected from the group consisting of:

(a) 0.2×sodium chloride/sodium citrate (SSC) at 50° C. to 65° C.;

(b) 2.0×SSC at 44° C. to 50° C; and (c) 60×SCC at 45° C.

2. An isolated nucleic acid molecule as claimed in claim 1 which comprises:

(i) a nucleic acid sequence as shown in SEQ ID NO:2 or FIG. 6, wherein T can also be U;

(ii) nucleic acid sequences complementary to (i);

(iii) a nucleic acid capable of hybridizing under high stringency salt and temperature conditions to a nucleic acid of (i), wherein said high stringency salt and temperature conditions are selected from the group consisting of:

(a) 0.2×sodium chloride/sodium citrate (SSC) at 50° C. to 65° C.;

(b) 2.0×SSC at 44° C. to 50° C.; and (c) 6.0×SSC at 45° C.; or (iv) a nucleic acid molecule different from any of the nucleic acids of (i) to (iii) in codon sequences due to the degeneracy of the genetic code.

3. An isolated nucleic acid molecule as claimed in claim 1, encoding amino acids 190 to 376, amino acids 377 to 472, or amino acids 29 to 189 in SEQ ID NO:2.

4. A vector comprising a nucleic acid molecule as claimed in claim 1 and the necessary elements for the transcription and translation of the inserted coding sequence.

5. A host cell containing a vector as claimed in claim 4.

6. A method for preparing a ShcC protein comprising (a) transferring a vector as claimed in claim 4 into a host cell; (b) selecting transformed host cells from untransformed host cells; (c) culturing a selected transformed host cell under conditions which allow expression of the ShcC protein; and (d) isolating the ShcC protein.

7. A vector comprising a nucleic acid molecule as claimed in claim 2 and the necessary elements for the transcription and translation of the inserted coding sequence.

8. A vector comprising a nucleic acid molecule as claimed in claim 3 and the necessary elements for the transcription and translation of the inserted coding sequence.

9. A host cell containing a vector as claimed in claim 8.

10. A method for preparing a ShcC protein comprising (a) transferring a vector as claimed in claim 8 into a host cell; (b) selecting transformed host cells from untransformed host cells; (c) culturing a selected transformed host cell under conditions which allow expression of the ShcC protein; and (d) isolating the ShcC protein.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1535 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 4..1425

(xi) SEQUENCE DESCRIPTION: SEQ ID NO:1:

```
GTG ATG AGT GCC ACC AGG AAG AGC CGG GCC GGC GAC GAG CCA CTG CCC         48
    Met Ser Ala Thr Arg Lys Ser Arg Ala Gly Asp Glu Pro Leu Pro
    1               5                  10                  15

AGG CCC CCT CGG GGC GCG CCG CAC ACC AGC GAT CAG GTG CTG GGG CCG         96
Arg Pro Pro Arg Gly Ala Pro His Thr Ser Asp Gln Val Leu Gly Pro
                20                  25                  30

GGA GTC ACC TAT GTG GTC AAG TAC TTG GGC TGC ATC GAA GTT CTG CGC        144
Gly Val Thr Tyr Val Val Lys Tyr Leu Gly Cys Ile Glu Val Leu Arg
            35                  40                  45

TCA ATG AGG TCT CTT GAC TTC AGT ACA AGA ACT CAG GTT ACC AGG GAA        192
Ser Met Arg Ser Leu Asp Phe Ser Thr Arg Thr Gln Val Thr Arg Glu
```

-continued

```
              50                    55                    60
GCC ATC AGC CGT GTC TGC GAA CGT GTG CCA GGT GCC AAA GGA GCC CTC      240
Ala Ile Ser Arg Val Cys Glu Arg Val Pro Gly Ala Lys Gly Ala Leu
         65                    70                    75

AAG AAG AGA AAG CCG CCG AGT AAG ATG CTG TCC AGC ATC CTG GGG AAG      288
Lys Lys Arg Lys Pro Pro Ser Lys Met Leu Ser Ser Ile Leu Gly Lys
 80                    85                    90                    95

AGC AAC CTC CAG TTC GCA GGG ATG AGC ATC TCC CTG ACC ATC TCC ACC      336
Ser Asn Leu Gln Phe Ala Gly Met Ser Ile Ser Leu Thr Ile Ser Thr
                 100                   105                   110

GCC AGC CTG AAT CTG CGC ACT CCT GAC TCC AAA CAG ATC ATA GCG AAC      384
Ala Ser Leu Asn Leu Arg Thr Pro Asp Ser Lys Gln Ile Ile Ala Asn
             115                   120                   125

CAT CAT ATG CGG TCT ATC TCT TTT GCC TCA GGG GGA GAC CCG GAC ACA      432
His His Met Arg Ser Ile Ser Phe Ala Ser Gly Gly Asp Pro Asp Thr
         130                   135                   140

ACG GAC TAT GTT GCC TAT GTC GCT AAG GAC CCT GTC AAT CGC AGA GCT      480
Thr Asp Tyr Val Ala Tyr Val Ala Lys Asp Pro Val Asn Arg Arg Ala
 145                   150                   155

TGC CAC ATT CTG GAA TGC TGT GAC GGG CTA GCC CAA GAT GTC ATT GGC      528
Cys His Ile Leu Glu Cys Cys Asp Gly Leu Ala Gln Asp Val Ile Gly
160                   165                   170                   175

TCC ATC GGA CAA GCC TTT GAA CTC CGG TTC AAA CAG TAT TTG CAG TGC      576
Ser Ile Gly Gln Ala Phe Glu Leu Arg Phe Lys Gln Tyr Leu Gln Cys
                 180                   185                   190

CCT TCC AAG GTT CCT GCC CTC CAG GAC CGA ATG CAG AGT CTG GAT GAG      624
Pro Ser Lys Val Pro Ala Leu Gln Asp Arg Met Gln Ser Leu Asp Glu
             195                   200                   205

CCA TGG ACT GAA GAA GAG GGA GAT GGC CCT GAT CAC CCA TAC TAC AAC      672
Pro Trp Thr Glu Glu Glu Gly Asp Gly Pro Asp His Pro Tyr Tyr Asn
         210                   215                   220

AGC GTT CCC ACC AAG ATG CCT CCC CCA GGG GGG TTT CTG GAT GCT CGA      720
Ser Val Pro Thr Lys Met Pro Pro Pro Gly Gly Phe Leu Asp Ala Arg
 225                   230                   235

TTG AAA GGC AGA CCC CAC GCT CCT GAG GCA GCC CAG TTT GCA GGA AAA      768
Leu Lys Gly Arg Pro His Ala Pro Glu Ala Ala Gln Phe Ala Gly Lys
240                   245                   250                   255

GAG CAA ACT TAT TAC CAG GGA AGA CAC TTA GGA GAT ACA TTT GGT GAA      816
Glu Gln Thr Tyr Tyr Gln Gly Arg His Leu Gly Asp Thr Phe Gly Glu
                 260                   265                   270

GAC TGG CAG CGA GCA CCC ACC AGG CAA GGC TCC TTG GAC ATC TAT AGC      864
Asp Trp Gln Arg Ala Pro Thr Arg Gln Gly Ser Leu Asp Ile Tyr Ser
             275                   280                   285

ACA GCA GAA GGG AAA ACT CAC ATG GTT CCT GTA GGA GAA ACA CCA ACC      912
Thr Ala Glu Gly Lys Thr His Met Val Pro Val Gly Glu Thr Pro Thr
         290                   295                   300

TAT GTC AAC ACC CAG CCA GTC CCA CCA CAG GTG TGG CCA GCA GCA ACC      960
Tyr Val Asn Thr Gln Pro Val Pro Pro Gln Val Trp Pro Ala Ala Thr
 305                   310                   315

AGC AGC ACT GAG AGC AGC CCA CGG AAG GAC CTC TTT GAC ATG AAG CCC     1008
Ser Ser Thr Glu Ser Ser Pro Arg Lys Asp Leu Phe Asp Met Lys Pro
320                   325                   330                   335

TTT GAA GAT GCC CTG AGA AAC CAG CCC CTG GGC CCC ATG TTG AGC AAA     1056
Phe Glu Asp Ala Leu Arg Asn Gln Pro Leu Gly Pro Met Leu Ser Lys
                 340                   345                   350

GCC GCG TCT GTG GAG TGC ATC AGC CCG GTC ACA CCC AGA GCC CCG GAT     1104
Ala Ala Ser Val Glu Cys Ile Ser Pro Val Thr Pro Arg Ala Pro Asp
             355                   360                   365

GCC AGG ATG CTG GAG GAG CTT AAC GCT GAG CCC TGG TAC CAA GGA GAG     1152
```

-continued

```
Ala Arg Met Leu Glu Glu Leu Asn Ala Glu Pro Trp Tyr Gln Gly Glu
            370                 375                 380

ATG AGC AGG AAG GAG GCA GAG GCC CTG CTA CGG GAA GAT GGA GAC TTC       1200
Met Ser Arg Lys Glu Ala Glu Ala Leu Leu Arg Glu Asp Gly Asp Phe
385                 390                 395

CTA GTG AGG AAG AGT ACC ACC AAC CCC GGC TCC TTT GTC CTC ACA GGC       1248
Leu Val Arg Lys Ser Thr Thr Asn Pro Gly Ser Phe Val Leu Thr Gly
400                 405                 410                 415

ATG CAC AAT GGG CAG GCC AAG CAC CTG CTG CTG GTG GAC CCG GAA GGC       1296
Met His Asn Gly Gln Ala Lys His Leu Leu Leu Val Asp Pro Glu Gly
            420                 425                 430

ACG ATC CGG ACG AAG GAC AGG GTC TTT GAC AGC ATC AGC CAC CTC ATC       1344
Thr Ile Arg Thr Lys Asp Arg Val Phe Asp Ser Ile Ser His Leu Ile
            435                 440                 445

AAT TAC CAC CTC GAG AGC AGC CTG CCC ATT GTC TCT GCC GGG AGT GAG       1392
Asn Tyr His Leu Glu Ser Ser Leu Pro Ile Val Ser Ala Gly Ser Glu
            450                 455                 460

CTT TGT CTC CAG CAA CCA GTG GAG AGG AAA CCC TGAGCTTGCC CAGCGCCCCA     1445
Leu Cys Leu Gln Gln Pro Val Glu Arg Lys Pro
465                 470

GCCCCCATAC CTTATGCCAG GTCAGGAAGA CTGGCTCTGC GGCTCTCAGC CTATGGAAAT    1505

GGGGCACTGT CTGTGGCCAT CACATTAAAG                                     1535

(2) INFORMATION FOR SEQ ID NO:2:

(i) SEQUENCE CHARACTERISTICS:
        (A) LENGTH: 474 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ala Thr Arg Lys Ser Arg Ala Gly Asp Glu Pro Leu Pro Arg
1               5                   10                  15

Pro Pro Arg Gly Ala Pro His Thr Ser Asp Gln Val Leu Gly Pro Gly
                20                  25                  30

Val Thr Tyr Val Val Lys Tyr Leu Gly Cys Ile Glu Val Leu Arg Ser
            35                  40                  45

Met Arg Ser Leu Asp Phe Ser Thr Arg Thr Gln Val Thr Arg Glu Ala
        50                  55                  60

Ile Ser Arg Val Cys Glu Arg Val Pro Gly Ala Lys Gly Ala Leu Lys
65                  70                  75                  80

Lys Arg Lys Pro Pro Ser Lys Met Leu Ser Ile Leu Gly Lys Ser
                85                  90                  95

Asn Leu Gln Phe Ala Gly Met Ser Ile Ser Leu Thr Ile Ser Thr Ala
                100                 105                 110

Ser Leu Asn Leu Arg Thr Pro Asp Ser Lys Gln Ile Ile Ala Asn His
            115                 120                 125

His Met Arg Ser Ile Ser Phe Ala Ser Gly Gly Asp Pro Asp Thr Thr
        130                 135                 140

Asp Tyr Val Ala Tyr Val Ala Lys Asp Pro Val Asn Arg Arg Ala Cys
145                 150                 155                 160

His Ile Leu Glu Cys Cys Asp Gly Leu Ala Gln Asp Val Ile Gly Ser
                165                 170                 175

Ile Gly Gln Ala Phe Glu Leu Arg Phe Lys Gln Tyr Leu Gln Cys Pro
            180                 185                 190
```

```
Ser Lys Val Pro Ala Leu Gln Asp Arg Met Gln Ser Leu Asp Glu Pro
        195                 200                 205

Trp Thr Glu Glu Glu Gly Asp Gly Pro Asp His Pro Tyr Tyr Asn Ser
    210                 215                 220

Val Pro Thr Lys Met Pro Pro Gly Gly Phe Leu Asp Ala Arg Leu
225                 230                 235                 240

Lys Gly Arg Pro His Ala Pro Glu Ala Ala Gln Phe Ala Gly Lys Glu
                245                 250                 255

Gln Thr Tyr Tyr Gln Gly Arg His Leu Gly Asp Thr Phe Gly Glu Asp
                260                 265                 270

Trp Gln Arg Ala Pro Thr Arg Gln Gly Ser Leu Asp Ile Tyr Ser Thr
    275                 280                 285

Ala Glu Gly Lys Thr His Met Val Pro Val Gly Glu Thr Pro Thr Tyr
    290                 295                 300

Val Asn Thr Gln Pro Val Pro Pro Gln Val Trp Pro Ala Ala Thr Ser
305                 310                 315                 320

Ser Thr Glu Ser Ser Pro Arg Lys Asp Leu Phe Asp Met Lys Pro Phe
                325                 330                 335

Glu Asp Ala Leu Arg Asn Gln Pro Leu Gly Pro Met Leu Ser Lys Ala
                340                 345                 350

Ala Ser Val Glu Cys Ile Ser Pro Val Thr Pro Arg Ala Pro Asp Ala
    355                 360                 365

Arg Met Leu Glu Glu Leu Asn Ala Glu Pro Trp Tyr Gln Gly Glu Met
    370                 375                 380

Ser Arg Lys Glu Ala Glu Ala Leu Leu Arg Glu Asp Gly Asp Phe Leu
385                 390                 395                 400

Val Arg Lys Ser Thr Thr Asn Pro Gly Ser Phe Val Leu Thr Gly Met
                405                 410                 415

His Asn Gly Gln Ala Lys His Leu Leu Leu Val Asp Pro Glu Gly Thr
                420                 425                 430

Ile Arg Thr Lys Asp Arg Val Phe Asp Ser Ile Ser His Leu Ile Asn
    435                 440                 445

Tyr His Leu Glu Ser Ser Leu Pro Ile Val Ser Ala Gly Ser Glu Leu
    450                 455                 460

Cys Leu Gln Gln Pro Val Glu Arg Lys Pro
465                 470

(2) INFORMATION FOR SEQ ID NO:3:

(i) SEQUENCE CHARACTERISTICS:
        (A) LENGTH: 1662 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat_peptide
        (B) LOCATION: 1

(ix) FEATURE:
        (A) NAME/KEY: CDS
        (B) LOCATION: join(1..1470, 1474..1479, 1483..1656)

(xi) SEQUENCE DESCRIPTION: SEQ ID NO:3:

CGC TGC CGG GGC TCG GGG ACG CGG GGC GCG CGG GTG ACT CCG GAT GTC      48
Arg Cys Arg Gly Ser Gly Thr Arg Gly Ala Arg Val Thr Pro Asp Val
1               5                   10                  15
```

-continued

| | |
|---|---|
| GCT GAC GAG TGG GTG CGC AAG GGC GGC TTC ATT CAC AAG CCG GCG CAC<br>Ala Asp Glu Trp Val Arg Lys Gly Gly Phe Ile His Lys Pro Ala His<br>20 25 30 | 96 |
| GGC TGG TTG CAT CCC GAT GCC AGG GTC CTG GGG CCC GGG GTC TCT TAC<br>Gly Trp Leu His Pro Asp Ala Arg Val Leu Gly Pro Gly Val Ser Tyr<br>35 40 45 | 144 |
| ATC GTT CGG TAC ATG GGC TGC ATT GAG GTG CTT CGA TCC ATG CGC TCC<br>Ile Val Arg Tyr Met Gly Cys Ile Glu Val Leu Arg Ser Met Arg Ser<br>50 55 60 | 192 |
| CTG GAT TTC AAC ACC CGA ACA CAG GTG ACG AGG GAA GCC ATC AAT CGG<br>Leu Asp Phe Asn Thr Arg Thr Gln Val Thr Arg Glu Ala Ile Asn Arg<br>65 70 75 80 | 240 |
| CTC CAT GAG GCT GTG CCC GGT GTC CGG GGC TCC TGG AAG AAG AAG GCC<br>Leu His Glu Ala Val Pro Gly Val Arg Gly Ser Trp Lys Lys Lys Ala<br>85 90 95 | 288 |
| CCC AAC AAG GCT CTG GCC TCC ATC TTG GGG AAA AGC AAC CTG CGC TTC<br>Pro Asn Lys Ala Leu Ala Ser Ile Leu Gly Lys Ser Asn Leu Arg Phe<br>100 105 110 | 336 |
| GCC GGC ATG AGC ATC TCA GTC AAC ATC TCC GTG GAC GGC CTT AAC TTG<br>Ala Gly Met Ser Ile Ser Val Asn Ile Ser Val Asp Gly Leu Asn Leu<br>115 120 125 | 384 |
| TCT GTT CCC GCC ACC CGC CAG ATC ATC GCC AAC CAT CAT ATG CAG TCT<br>Ser Val Pro Ala Thr Arg Gln Ile Ile Ala Asn His His Met Gln Ser<br>130 135 140 | 432 |
| ATT TCC TTC GCC TCG GGT GGT GAC ACG GAC ATG ACT GAT TAC GTG GCC<br>Ile Ser Phe Ala Ser Gly Gly Asp Thr Asp Met Thr Asp Tyr Val Ala<br>145 150 155 160 | 480 |
| TAT GTG GCC AAG GAC CCC ATC AAC CAG AGA GCC TGC CAC ATC TTG GAA<br>Tyr Val Ala Lys Asp Pro Ile Asn Gln Arg Ala Cys His Ile Leu Glu<br>165 170 175 | 528 |
| TGC TGT GAA GGT CTT GCC CAG AGC GTC ATC AGC ACC GTA GGG CAA GCC<br>Cys Cys Glu Gly Leu Ala Gln Ser Val Ile Ser Thr Val Gly Gln Ala<br>180 185 190 | 576 |
| TTT GAG CTG CGC TTC AAG CAA TAC CTG CAC AGT CCG CCC AAG GCG GTA<br>Phe Glu Leu Arg Phe Lys Gln Tyr Leu His Ser Pro Pro Lys Ala Val<br>195 200 205 | 624 |
| GTG CCC CCT GAA AGG CTG ACT GGG CTG GAG GAG TTG GCC TGG GGA GAT<br>Val Pro Pro Glu Arg Leu Thr Gly Leu Glu Glu Leu Ala Trp Gly Asp<br>210 215 220 | 672 |
| GAT GAC GCT GCT GCA GAC CAC AAT TAC TAC AAC AGC ATT CCG GGA AAG<br>Asp Asp Ala Ala Ala Asp His Asn Tyr Tyr Asn Ser Ile Pro Gly Lys<br>225 230 235 240 | 720 |
| GAG CCA CCC CTG GGC GGG CTG GTG GAC TCC AGA CTG GCT GTC ACA CAG<br>Glu Pro Pro Leu Gly Gly Leu Val Asp Ser Arg Leu Ala Val Thr Gln<br>245 250 255 | 768 |
| CCC TGT GCG CTG GCG ACA CTC GGG GGC CTT GGA CAG GGA ATG ACA CCA<br>Pro Cys Ala Leu Ala Thr Leu Gly Gly Leu Gly Gln Gly Met Thr Pro<br>260 265 270 | 816 |
| GTA TGG AGA GAT GCC CGT GGC TTG CCT TGG GAC ATG GGC CCC TCT GGA<br>Val Trp Arg Asp Ala Arg Gly Leu Pro Trp Asp Met Gly Pro Ser Gly<br>275 280 285 | 864 |
| GCA GCC CCA CCG GGG GAT GGC TAC GTG CAG GCA GAT GCC CGA GGG CCA<br>Ala Ala Pro Pro Gly Asp Gly Tyr Val Gln Ala Asp Ala Arg Gly Pro<br>290 295 300 | 912 |
| CAT GAC TAC GAG GAG CAC CTG TAT GTC AAT ACC CAG GGC CTG GAT GCT<br>His Asp Tyr Glu Glu His Leu Tyr Val Asn Thr Gln Gly Leu Asp Ala<br>305 310 315 320 | 960 |
| GTG GAG CTT GAG GAC ACC GCC GAG GCA CCT CTG CAG TTT GAG GAC AGC<br>Val Glu Leu Glu Asp Thr Ala Glu Ala Pro Leu Gln Phe Glu Asp Ser<br>325 330 335 | 1008 |

```
CCC AAG AAG GAC CTG TTT GAC ATG CGA CCC TTT GAA GAT GCC CTG AAG      1056
Pro Lys Lys Asp Leu Phe Asp Met Arg Pro Phe Glu Asp Ala Leu Lys
            340                 345                 350

TTG CAC GCG TGC TCA GTG GCA GCC GGC ATC ACT GCA GCC TCA CCC CCT      1104
Leu His Ala Cys Ser Val Ala Ala Gly Ile Thr Ala Ala Ser Pro Pro
            355                 360                 365

CTG GAA GAC CAG TGG CCC AGT CCC CCT ACC CGC AGG GCC CCC ATT GCA      1152
Leu Glu Asp Gln Trp Pro Ser Pro Pro Thr Arg Arg Ala Pro Ile Ala
        370                 375                 380

CCC ACA GAG GAG CAA TTG AGG CAG GAG CCC TGG TAC CAC GGA CGA ATG      1200
Pro Thr Glu Glu Gln Leu Arg Gln Glu Pro Trp Tyr His Gly Arg Met
385                 390                 395                 400

AGC CGT CGG GCT GCA GAG AAG CTG CTT CGG GCC GAT GGG GAC TTC CTT      1248
Ser Arg Arg Ala Ala Glu Lys Leu Leu Arg Ala Asp Gly Asp Phe Leu
                405                 410                 415

GTG AGA GAC AGC GTC ACC AAC CCG GGG CAG TAT GTC CTC ACG GGC ATG      1296
Val Arg Asp Ser Val Thr Asn Pro Gly Gln Tyr Val Leu Thr Gly Met
            420                 425                 430

CAT GCG GGG CAG CCC AAG CAC CTG CTG CTG GTG GAC CCC GAG GGT GTG      1344
His Ala Gly Gln Pro Lys His Leu Leu Leu Val Asp Pro Glu Gly Val
            435                 440                 445

GTG CGG ACG AAA GAT GTG TTG TTT GAG AGC ATC AGC CAC CTC ATA GAC      1392
Val Arg Thr Lys Asp Val Leu Phe Glu Ser Ile Ser His Leu Ile Asp
450                 455                 460

TAT CAC CTG AAG AAT GGG CTG CCT ATC GTG GCT GCT GAG AGC GAG CTG      1440
Tyr His Leu Lys Asn Gly Leu Pro Ile Val Ala Ala Glu Ser Glu Leu
465                 470                 475                 480

CAT CTG CGG GGA GTG GTC TCT CGG GAG CCA TGA GCC AGG TGA CAG TCC      1488
His Leu Arg Gly Val Val Ser Arg Glu Pro     Ala Arg     Gln Ser
                485                 490

TCA CCC CAA CTT CTA CCC CTA GAT GCC CTT GCT GAG GCC TTT CTC TCA      1536
Ser Pro Gln Leu Leu Pro Leu Asp Ala Leu Ala Glu Ala Phe Leu Ser
495                 500                 505                 510

GAT CCT GAA GCC ACG AGA ACC AGA ATG GTT ACC ACC TCT CCT TCC ACA      1584
Asp Pro Glu Ala Thr Arg Thr Arg Met Val Thr Thr Ser Pro Ser Thr
                515                 520                 525

CGA GCC CTC GGG AAG CCG CCT TTC CCA GCT GTG CTC GCT CAG CTG GGG      1632
Arg Ala Leu Gly Lys Pro Pro Phe Pro Ala Val Leu Ala Gln Leu Gly
            530                 535                 540

GGG CCC GGT ACC CAA TTC GCC CTA TAGTGA                               1662
Gly Pro Gly Thr Gln Phe Ala Leu
            545                 550

(2) INFORMATION FOR SEQ ID NO:4:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:4:

Arg Cys Arg Gly Ser Gly Thr Arg Gly Ala Arg Val Thr Pro Asp Val
1               5                   10                  15

Ala Asp Glu Trp Val Arg Lys Gly Phe Ile His Lys Pro Ala His
            20                  25                  30

Gly Trp Leu His Pro Asp Ala Arg Val Leu Gly Pro Gly Val Ser Tyr
        35                  40                  45

Ile Val Arg Tyr Met Gly Cys Ile Glu Val Leu Arg Ser Met Arg Ser
```

-continued

```
             50                  55                  60
Leu Asp Phe Asn Thr Arg Thr Gln Val Thr Arg Glu Ala Ile Asn Arg
 65                  70                  75                  80
Leu His Glu Ala Val Pro Gly Val Arg Gly Ser Trp Lys Lys Lys Ala
                 85                  90                  95
Pro Asn Lys Ala Leu Ala Ser Ile Leu Gly Lys Ser Asn Leu Arg Phe
                100                 105                 110
Ala Gly Met Ser Ile Ser Val Asn Ile Ser Val Asp Gly Leu Asn Leu
                115                 120                 125
Ser Val Pro Ala Thr Arg Gln Ile Ile Ala Asn His Met Gln Ser
                130                 135                 140
Ile Ser Phe Ala Ser Gly Gly Asp Thr Asp Met Thr Asp Tyr Val Ala
145                 150                 155                 160
Tyr Val Ala Lys Asp Pro Ile Asn Gln Arg Ala Cys His Ile Leu Glu
                165                 170                 175
Cys Cys Glu Gly Leu Ala Gln Ser Val Ile Ser Thr Val Gly Gln Ala
                180                 185                 190
Phe Glu Leu Arg Phe Lys Gln Tyr Leu His Ser Pro Lys Ala Val
                195                 200                 205
Val Pro Pro Glu Arg Leu Thr Gly Leu Glu Glu Leu Ala Trp Gly Asp
210                 215                 220
Asp Asp Ala Ala Asp His Asn Tyr Tyr Asn Ser Ile Pro Gly Lys
225                 230                 235                 240
Glu Pro Pro Leu Gly Gly Leu Val Asp Ser Arg Leu Ala Val Thr Gln
                245                 250                 255
Pro Cys Ala Leu Ala Thr Leu Gly Gly Leu Gly Gln Gly Met Thr Pro
                260                 265                 270
Val Trp Arg Asp Ala Arg Gly Leu Pro Trp Asp Met Gly Pro Ser Gly
                275                 280                 285
Ala Ala Pro Pro Gly Asp Gly Tyr Val Gln Ala Asp Ala Arg Gly Pro
                290                 295                 300
His Asp Tyr Glu Glu His Leu Tyr Val Asn Thr Gln Gly Leu Asp Ala
305                 310                 315                 320
Val Glu Leu Glu Asp Thr Ala Glu Ala Pro Leu Gln Phe Glu Asp Ser
                325                 330                 335
Pro Lys Lys Asp Leu Phe Asp Met Arg Pro Phe Glu Asp Ala Leu Lys
                340                 345                 350
Leu His Ala Cys Ser Val Ala Ala Gly Ile Thr Ala Ala Ser Pro Pro
                355                 360                 365
Leu Glu Asp Gln Trp Pro Ser Pro Pro Thr Arg Arg Ala Pro Ile Ala
                370                 375                 380
Pro Thr Glu Glu Gln Leu Arg Gln Glu Pro Trp Tyr His Gly Arg Met
385                 390                 395                 400
Ser Arg Arg Ala Ala Glu Lys Leu Leu Arg Ala Asp Gly Asp Phe Leu
                405                 410                 415
Val Arg Asp Ser Val Thr Asn Pro Gly Gln Tyr Val Leu Thr Gly Met
                420                 425                 430
His Ala Gly Gln Pro Lys His Leu Leu Leu Val Asp Pro Glu Gly Val
                435                 440                 445
Val Arg Thr Lys Asp Val Leu Phe Glu Ser Ile Ser His Leu Ile Asp
                450                 455                 460
Tyr His Leu Lys Asn Gly Leu Pro Ile Val Ala Ala Glu Ser Glu Leu
465                 470                 475                 480
```

```
His Leu Arg Gly Val Val Ser Arg Glu Pro Ala Arg Gln Ser Ser Pro
                485                 490                 495

Gln Leu Leu Pro Leu Asp Ala Leu Ala Glu Ala Phe Leu Ser Asp Pro
            500                 505                 510

Glu Ala Thr Arg Thr Arg Met Val Thr Thr Ser Pro Ser Thr Arg Ala
            515                 520                 525

Leu Gly Lys Pro Pro Phe Pro Ala Val Leu Ala Gln Leu Gly Gly Pro
            530                 535                 540

Gly Thr Gln Phe Ala Leu
545                 550

(2) INFORMATION FOR SEQ ID NO:5:

(i) SEQUENCE CHARACTERISTICS:
        (A) LENGTH: 431 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:5:

Pro Gly Ser Gly Asp Ala Ala Ala Ala Glu Trp Ile Arg Lys Gly
1               5                   10                  15

Ser Phe Ile His Lys Pro Ala His Gly Trp Leu His Pro Asp Ala Arg
            20                  25                  30

Val Leu Gly Pro Gly Val Ser Tyr Val Val Arg Tyr Met Gly Cys Ile
            35                  40                  45

Glu Val Leu Arg Ser Met Arg Ser Leu Asp Phe Asn Thr Arg Thr Gln
50                  55                  60

Val Thr Arg Glu Ala Ile Asn Arg Leu His Glu Ala Val Pro Gly Val
65                  70                  75                  80

Arg Gly Ser Trp Lys Lys Lys Ala Pro Asn Lys Ala Leu Ala Ser Val
            85                  90                  95

Leu Gly Lys Ser Asn Leu Arg Phe Ala Gly Met Ser Ile Ser Ile His
            100                 105                 110

Ile Ser Thr Asp Gly Leu Ser Leu Ser Val Pro Ala Thr Arg Gln Val
            115                 120                 125

Ile Ala Asn His His Met Pro Ser Ile Ser Phe Ala Ser Gly Gly Asp
130                 135                 140

Thr Asp Met Thr Asp Tyr Val Ala Tyr Val Ala Lys Asp Pro Ile Asn
145                 150                 155                 160

Gln Arg Ala Cys His Ile Leu Glu Cys Cys Glu Gly Leu Ala Gln Ser
            165                 170                 175

Ile Ile Ser Thr Val Gly Gln Ala Phe Glu Leu Arg Phe Lys Gln Tyr
            180                 185                 190

Leu His Ser Pro Pro Lys Val Ala Leu Pro Pro Glu Arg Leu Ala Gly
            195                 200                 205

Pro Glu Glu Ser Ala Trp Gly Asp Glu Glu Asp Ser Leu Glu Asp Asp
            210                 215                 220

His Tyr Tyr Asn Ser Ile Pro Gly Lys Glu Pro Pro Leu Gly Gly Leu
225                 230                 235                 240

Val Asp Ser Arg Leu Ala Leu Thr Gln Pro Cys Ala Leu Ala Leu Thr
                245                 250                 255

Ala Leu Asp Gln Gly Pro Ser Pro Ser Leu Arg Asp Ala Cys Ser Leu
            260                 265                 270
```

```
Pro Trp Asp Val Gly Ser Thr Gly Thr Ala Pro Gly Asp Gly Tyr
        275                 280                 285

Val Gln Ala Asp Ala Arg Gly Pro Pro Asp His Glu Glu His Leu Tyr
    290                 295                 300

Val Asn Thr Gln Gly Leu Asp Ala Pro Glu Pro Glu Asp Ser Pro Lys
305                 310                 315                 320

Lys Asp Leu Phe Asp Met Arg Pro Glu Glu Asp Ala Leu Lys Leu His
                325                 330                 335

Glu Cys Ser Val Ala Ala Gly Val Thr Ala Ala Pro Leu Pro Leu Glu
                340                 345                 350

Asp Gln Trp Pro Ser Pro Pro Thr Arg Arg Ala Pro Val Ala Pro Thr
                355                 360                 365

Glu Glu Gln Leu Arg Gln Glu Pro Trp Tyr His Gly Arg Met Ser Arg
    370                 375                 380

Arg Ala Ala Glu Arg Met Leu Arg Ala Asp Gly Asp Phe Leu Val Arg
385                 390                 395                 400

Asp Ser Val Thr Asn Pro Gly Gln Tyr Val Leu Thr Gly Met His Ala
                405                 410                 415

Gly Gln Pro Lys His Leu Leu Leu Val Asp Pro Glu Gly Val Val
                420                 425                 430

(2) INFORMATION FOR SEQ ID NO:6:

(i) SEQUENCE CHARACTERISTICS:
        (A) LENGTH: 469 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:6:

Met Asn Lys Leu Ser Gly Gly Gly Arg Arg Thr Arg Val Glu Gly
1               5                   10                  15

Gly Gln Leu Gly Gly Glu Glu Trp Thr Arg His Gly Ser Phe Val Asn
            20                  25                  30

Lys Pro Thr Arg Gly Trp Leu His Pro Asn Asp Lys Val Met Gly Pro
            35                  40                  45

Gly Val Ser Tyr Leu Val Arg Tyr Met Gly Cys Val Glu Val Leu Gln
    50                  55                  60

Ser Met Arg Ala Leu Asp Phe Asn Thr Arg Thr Gln Val Thr Arg Glu
65                  70                  75                  80

Ala Ile Ser Leu Val Cys Glu Ala Val Pro Gly Ala Lys Gly Ala Thr
                85                  90                  95

Arg Arg Arg Lys Pro Cys Ser Arg Pro Leu Ser Ser Ile Leu Gly Arg
                100                 105                 110

Ser Asn Leu Lys Phe Ala Gly Met Pro Ile Thr Leu Thr Val Ser Thr
            115                 120                 125

Ser Ser Leu Asn Leu Met Ala Ala Asp Cys Lys Gln Ile Ile Ala Asn
130                 135                 140

His His Met Gln Ser Ile Ser Phe Ala Ser Gly Gly Asp Pro Asp Thr
145                 150                 155                 160

Ala Glu Tyr Val Ala Tyr Val Ala Lys Asp Pro Val Asn Gln Arg Ala
                165                 170                 175

Cys His Ile Leu Glu Cys Pro Glu Gly Leu Ala Gln Asp Val Ile Ser
                180                 185                 190
```

```
Thr Ile Gly Gln Ala Phe Glu Leu Arg Phe Lys Gln Tyr Leu Arg Asn
            195                 200                 205

Pro Pro Lys Leu Val Thr Pro His Asp Arg Met Ala Gly Phe Asp Gly
210                 215                 220

Ser Ala Trp Asp Glu Glu Glu Glu Pro Pro Asp His Gln Tyr Tyr
225                 230                 235                 240

Asn Asp Phe Pro Gly Lys Glu Pro Pro Leu Gly Gly Val Val Asp Met
            245                 250                 255

Arg Leu Arg Glu Gly Ala Ala Arg Pro Thr Leu Pro Ser Ala Gln Met
            260                 265                 270

Ser Ser His Leu Gly Ala Thr Leu Pro Ile Gly Gln His Ala Ala Gly
            275                 280                 285

Asp His Glu Val Arg Lys Gln Met Leu Pro Pro Pro Cys Pro Gly
290                 295                 300

Arg Glu Leu Phe Asp Asp Pro Ser Tyr Val Asn Ile Gln Asn Leu Asp
305                 310                 315                 320

Lys Ala Arg Gln Ala Gly Gly Ala Gly Pro Pro Asn Pro Ser Leu
            325                 330                 335

Asn Gly Ser Ala Pro Arg Asp Leu Phe Asp Met Lys Pro Phe Glu Asp
            340                 345                 350

Ala Leu Arg Val Pro Pro Pro Gln Ser Met Ser Met Ala Glu Gln
            355                 360                 365

Leu Gln Gly Glu Pro Trp Phe His Gly Lys Leu Ser Arg Arg Glu Ala
            370                 375                 380

Glu Ala Leu Leu Gln Leu Asn Gly Asp Phe Leu Val Arg Glu Ser Thr
385                 390                 395                 400

Thr Thr Pro Gly Gln Tyr Val Leu Thr Gly Leu Gln Ser Gly Gln Pro
            405                 410                 415

Lys His Leu Leu Leu Val Asp Pro Glu Gly Val Val Arg Thr Lys Asp
            420                 425                 430

His Arg Phe Glu Ser Val Ser His Leu Ile Ser Tyr His Met Asp Asn
            435                 440                 445

His Leu Pro Ile Ile Ser Ala Gly Ser Glu Leu Cys Leu Gln Gln Pro
            450                 455                 460

Val Asp Arg Lys Val
465

(2) INFORMATION FOR SEQ ID NO:7:

(i) SEQUENCE CHARACTERISTICS:
        (A) LENGTH: 473 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:7:

Met Asn Lys Leu Ser Gly Gly Gly Arg Arg Thr Arg Val Glu Gly
1               5                   10                  15

Gly Gln Leu Gly Gly Glu Glu Trp Thr Arg His Gly Ser Phe Val Asn
            20                  25                  30

Lys Pro Thr Arg Gly Trp Leu His Pro Asn Asp Lys Val Met Gly Pro
            35                  40                  45

Gly Val Ser Tyr Leu Val Arg Tyr Met Gly Cys Val Glu Val Leu Gln
            50                  55                  60
```

-continued

```
Ser Met Arg Ala Leu Asp Phe Asn Thr Arg Thr Gln Val Thr Arg Glu
 65                  70                  75                  80

Ala Ile Ser Leu Val Cys Glu Ala Val Pro Gly Ala Lys Gly Ala Thr
                 85                  90                  95

Arg Arg Arg Lys Pro Cys Ser Arg Pro Leu Ser Ser Ile Leu Gly Arg
            100                 105                 110

Ser Asn Leu Lys Phe Ala Gly Met Pro Ile Thr Leu Thr Val Ser Thr
        115                 120                 125

Ser Ser Leu Asn Leu Met Ala Ala Asp Cys Lys Gln Ile Ile Ala Asn
130                 135                 140

His His Met Gln Ser Ile Ser Phe Ala Ser Gly Gly Asp Pro Asp Thr
145                 150                 155                 160

Ala Glu Tyr Val Ala Tyr Val Ala Lys Asp Pro Val Asn Gln Arg Ala
                165                 170                 175

Cys His Ile Leu Glu Cys Pro Glu Gly Leu Ala Gln Asp Val Ile Ser
            180                 185                 190

Thr Ile Gly Gln Ala Phe Glu Leu Arg Phe Lys Gln Tyr Leu Arg Asn
        195                 200                 205

Pro Pro Lys Leu Val Thr Pro His Asp Arg Met Ala Gly Phe Asp Gly
210                 215                 220

Ser Ala Trp Asp Glu Glu Glu Glu Pro Pro Asp His Gln Tyr Tyr
225                 230                 235                 240

Asn Asp Phe Pro Gly Lys Glu Pro Leu Gly Gly Val Val Asp Met
                245                 250                 255

Arg Leu Arg Glu Gly Ala Ala Pro Gly Ala Ala Arg Pro Thr Ala Pro
            260                 265                 270

Asn Ala Gln Thr Pro Ser His Leu Gly Ala Thr Leu Pro Val Gly Gln
        275                 280                 285

Pro Val Gly Gly Asp Pro Glu Val Arg Lys Gln Met Pro Pro Pro Pro
290                 295                 300

Pro Cys Pro Gly Arg Glu Leu Phe Asp Asp Pro Ser Tyr Val Asn Val
305                 310                 315                 320

Gln Asn Leu Asp Lys Ala Arg Gln Ala Val Gly Gly Ala Gly Pro Pro
                325                 330                 335

Asn Pro Ala Ile Asn Gly Ser Ala Pro Arg Asp Leu Phe Asp Met Lys
            340                 345                 350

Pro Phe Glu Asp Ala Leu Arg Val Pro Pro Pro Gln Ser Val Ser
        355                 360                 365

Met Ala Glu Gln Leu Arg Gly Glu Pro Trp Phe His Gly Lys Leu Ser
370                 375                 380

Arg Arg Glu Ala Glu Ala Leu Leu Gln Leu Asn Gly Asp Phe Leu Val
385                 390                 395                 400

Arg Glu Ser Thr Thr Thr Pro Gly Gln Tyr Val Leu Thr Gly Leu Gln
                405                 410                 415

Ser Gly Gln Pro Lys His Leu Leu Leu Val Asp Pro Glu Gly Val Val
            420                 425                 430

Arg Thr Lys Asp His Arg Phe Glu Ser Val Ser His Leu Ile Ser Tyr
        435                 440                 445

His Met Asp Asn His Leu Pro Ile Ile Ser Ala Gly Ser Glu Leu Cys
450                 455                 460

Leu Gln Gln Pro Val Glu Arg Lys Leu
465                 470
```

(2) INFORMATION FOR SEQ ID NO:8:

(i) SEQUENCE CHARACTERISTICS:
        (A) LENGTH: 409 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:8:

```
Met Pro Lys Asn Gly Asp Ala Gly Asn Arg Ser Gly Ser Gly Thr Thr
  1               5                  10                  15

Ser Asp Gly Cys Ile Tyr Pro Asp Asp Val Ile Met Gly Val Gly Val
                 20                  25                  30

Ala Phe Asn Val Arg Tyr Thr Gly Cys Val Glu Val Lys Thr Ser Met
             35                  40                  45

Lys Ser Leu Asp Phe Glu Thr Arg Thr Gln Leu Ala Arg Glu Cys Ile
 50                  55                  60

Asn Arg Val Cys Glu Ala Ala Gly Leu Lys Ser Ala Gly Lys Arg Arg
 65                  70                  75                  80

Leu Thr Asn Phe Ile Ser Asp Arg Pro Ser Met Gln His Ala Gly Thr
                 85                  90                  95

Asn Ile Ile Ile Asn Val Ser Ser Arg Ala Leu Ser Leu Ser Asn Val
                100                 105                 110

Glu Thr Gly Glu Val Ile Ala Asn His Asn Met Pro Arg Ile Ser Phe
            115                 120                 125

Ala Ser Gly Gly Asp Asn Asp Thr Leu Asp Phe Leu Ala Tyr Ile Ala
130                 135                 140

Lys Asn Glu Asp Glu Trp Arg Ala Cys Tyr Val Leu Glu Cys Ala Gly
145                 150                 155                 160

Gly Gln Ser Glu Asp Leu Ile Val Thr Ile Gly Lys Ala Phe Ala Leu
                165                 170                 175

Arg Phe Asn Ala Leu Ser Arg Leu Asn Asp Pro Ser Ala Asp Cys Asn
            180                 185                 190

Ile Asn Gln Ser Cys Lys Glu Asn Val Lys Glu Tyr Tyr Asn Asp Leu
            195                 200                 205

Pro Asn Lys Leu Pro Pro Glu Val Pro Glu Pro Gln Gln Gln Gln Val
210                 215                 220

Gln Gln Pro Leu His Pro His Ala Pro Arg Val Ala Gln Leu Asn Leu
225                 230                 235                 240

Lys Lys Pro Arg Asp Arg Leu Ser Ser Asn Leu Ile Asp Leu Asn Ser
                245                 250                 255

Pro Pro Pro Asp Gln Thr Thr Asn Lys Leu Gly His Phe Asp Pro Leu
            260                 265                 270

Gln Ala Thr Thr Ala Ala Asn Ser Val Leu Pro Ser Val Arg Asp Val
            275                 280                 285

Phe Asp Gly Pro Gln Cys Pro Leu Thr Ala Glu Val Trp Phe His Ala
290                 295                 300

Gly Ile Ser Arg Pro Ile Ser Glu Arg Leu Leu Gln Gln Asp Gly Asp
305                 310                 315                 320

Glu Leu Val Arg Glu Ser Gln Gly Lys Arg Gly Gln Tyr Val Leu Thr
                325                 330                 335

Gly Leu Glu Gly Lys Thr Pro Lys His Leu Leu Leu Ile Asp Pro Glu
            340                 345                 350
```

```
Gly Val Val Arg Thr Lys Asp Arg Ile Phe Asp Ser Ile Ser His Leu
        355                 360                 365
Ile Asn Tyr His Trp Ala His Ala Leu Pro Ile Ile Ser Glu Asp Ser
        370                 375                 380
Glu Leu Val Leu Arg Asn Pro Val Arg Arg Pro Gln Gln Asp Gln Ala
385             390                 395                 400
Ala Ser Pro Ile Thr Ser Ala Ser Ser
                405
```

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "phosphotyrosine site"

(ix) FEATURE:
        (A) NAME/KEY: Modified-site
        (B) LOCATION: 2
        (D) OTHER INFORMATION: /note= "can be substituted with a
            hydrophobic amino acid"

(ix) FEATURE:
        (A) NAME/KEY: Modified-site
        (B) LOCATION: 4
        (D) OTHER INFORMATION: /note= "can be substituted with a
            Leu or Met"

(xi) SEQUENCE DESCRIPTION: SEQ ID NO:9:

```
Tyr Glu Xaa Ile
1
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "can be substituted with
            Ile"

(ix) FEATURE:
        (A) NAME/KEY: Modified-site
        (B) LOCATION: 6
        (D) OTHER INFORMATION: /note= "phosphotyrosine site"

(xi) SEQUENCE DESCRIPTION: SEQ ID NO:10:

```
Leu Xaa Asn Pro Xaa Tyr
1               5
```

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS:

(D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /note= "phosphotyrosine site"

(ix) FEATURE:
            (A) NAME/KEY: Modified-site
            (B) LOCATION: 2
            (D) OTHER INFORMATION: /note= "can be substituted with a
                hydrophobic amino acid"

(ix) FEATURE:
            (A) NAME/KEY: Modified-site
            (B) LOCATION: 3
            (D) OTHER INFORMATION: /note= "can be hydrophobic/Met/Tyr
                or hydrophobic/Met/Ile"

(ix) FEATURE:
            (A) NAME/KEY: Modified-site
            (B) LOCATION: 4
            (D) OTHER INFORMATION: /note= "can be Ile/Leu/Met or
                Phe/Tyr"

(xi) SEQUENCE DESCRIPTION: SEQ ID NO:11:

Tyr Glu Xaa Xaa
1

(2) INFORMATION FOR SEQ ID NO:12:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 4
            (D) OTHER INFORMATION: /note= "phosphotyrosine site"

(xi) SEQUENCE DESCRIPTION: SEQ ID NO:12:

Asn Pro Xaa Tyr
1

(2) INFORMATION FOR SEQ ID NO:13:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:13:

Tyr Val Asn Thr
1

(2) INFORMATION FOR SEQ ID NO:14:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide

```
    (ix) FEATURE:
         (A) NAME/KEY: Modified-site
         (B) LOCATION: 1
         (D) OTHER INFORMATION: /note= "phosphotyrosine site"

(ix) FEATURE:
         (A) NAME/KEY: Modified-site
         (B) LOCATION: 2
         (D) OTHER INFORMATION: /note= "can be substituted with a
             hydrophobic amino acid"

(ix) FEATURE:
         (A) NAME/KEY: Modified-site
         (B) LOCATION: 3
         (D) OTHER INFORMATION: /note= "can be hydrophobic/Met/Tyr"

(ix) FEATURE:
         (A) NAME/KEY: Modified-site
         (B) LOCATION: 4
         (D) OTHER INFORMATION: /note= "can be substituted with a
             Leu or Met"

(xi) SEQUENCE DESCRIPTION: SEQ ID NO:14:

Tyr Glu Xaa Ile
1

(2) INFORMATION FOR SEQ ID NO:15:

(i) SEQUENCE CHARACTERISTICS:
         (A) LENGTH: 21 base pairs
         (B) TYPE: nucleic acid
         (C) STRANDEDNESS: single
         (D) TOPOLOGY: unknown (ii) MOLECULE TYPE: other nucleic acid
         (A) DESCRIPTION: /desc = "primer"

(xi) SEQUENCE DESCRIPTION: SEQ ID NO:15:

GTCATTGGCT CCATTCGGAC A                                              21

(2) INFORMATION FOR SEQ ID NO:16:

(i) SEQUENCE CHARACTERISTICS:
         (A) LENGTH: 20 base pairs
         (B) TYPE: nucleic acid
         (C) STRANDEDNESS: single
         (D) TOPOLOGY: unknown (ii) MOLECULE TYPE: other nucleic acid
         (A) DESCRIPTION: /desc = "primer"

(xi) SEQUENCE DESCRIPTION: SEQ ID NO:16:

ATCCTGGCAT CCGGGGCTCT                                                20

(2) INFORMATION FOR SEQ ID NO:17:

(i) SEQUENCE CHARACTERISTICS:
         (A) LENGTH: 11 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:17:

Tyr Tyr Asn Xaa Xaa Pro Xaa Lys Xaa Pro Pro
1               5                   10

(2) INFORMATION FOR SEQ ID NO:18:
```

```
    (i) SEQUENCE CHARACTERISTICS:
        (A) LENGTH: 14 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "can be substituted with an
            Arg"

(ix) FEATURE:
        (A) NAME/KEY: Modified-site
        (B) LOCATION: 7
        (D) OTHER INFORMATION: /note= "can be substituted with a
            Lys"

(ix) FEATURE:
        (A) NAME/KEY: Modified-site
        (B) LOCATION: 14
        (D) OTHER INFORMATION: /note= "can be substituted with an
            Arg"

(xi) SEQUENCE DESCRIPTION: SEQ ID NO:18:

Lys Asp Leu Phe Asp Met Arg Pro Phe Glu Asp Ala Leu Lys
1               5                   10
```